(12) United States Patent
Ji et al.

(10) Patent No.: US 12,180,294 B2
(45) Date of Patent: Dec. 31, 2024

(54) DIMERIC ANTIGEN RECEPTORS

(71) Applicant: Sorrento Therapeutics, Inc., San Diego, CA (US)

(72) Inventors: Henry Hongjun Ji, Rancho Santa Fe, CA (US); Wenzhong Guo, San Diego, CA (US); Yanliang Zhang, San Diego, CA (US); Gunnar F. Kaufmann, San Diego, CA (US); Bei Bei Ding, San Diego, CA (US)

(73) Assignee: Vivasor, Inc., San Diego, CA (US)

( * ) Notice: Subject to any disclaimer, the term of this patent is extended or adjusted under 35 U.S.C. 154(b) by 1154 days.

(21) Appl. No.: 17/013,359

(22) Filed: Sep. 4, 2020

(65) Prior Publication Data

US 2020/0399393 A1 Dec. 24, 2020

Related U.S. Application Data

(63) Continuation of application No. PCT/US2019/021681, filed on Mar. 11, 2019.

(60) Provisional application No. 62/640,775, filed on Mar. 9, 2018.

(51) Int. Cl.
| | |
|---|---|
| *C07K 16/28* | (2006.01) |
| *A61K 35/17* | (2015.01) |
| *A61K 38/00* | (2006.01) |
| *A61K 39/00* | (2006.01) |
| *A61P 35/00* | (2006.01) |
| *C07K 14/705* | (2006.01) |
| *C07K 14/725* | (2006.01) |
| *C12N 5/0783* | (2010.01) |

(52) U.S. Cl.
CPC .......... *C07K 16/2896* (2013.01); *A61K 35/17* (2013.01); *A61P 35/00* (2018.01); *C07K 14/7051* (2013.01); *C07K 14/70517* (2013.01); *C07K 14/70521* (2013.01); *C07K 14/70578* (2013.01); *C12N 5/0636* (2013.01); *A61K 38/00* (2013.01); *A61K 2039/505* (2013.01); *A61K 2039/5156* (2013.01); *A61K 2039/5158* (2013.01); *A61K 2039/572* (2013.01); *C07K 2317/51* (2013.01); *C07K 2317/515* (2013.01); *C07K 2317/53* (2013.01); *C07K 2317/73* (2013.01); *C07K 2317/76* (2013.01); *C07K 2319/02* (2013.01); *C07K 2319/03* (2013.01); *C07K 2319/30* (2013.01); *C07K 2319/33* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 11,116,834 B2 * | 9/2021 | Williams | ........... C07K 14/7051 |
| 2003/0124129 A1 | 7/2003 | Oliner | |
| 2014/0234348 A1 | 8/2014 | Scholler et al. | |
| 2016/0297888 A1 | 10/2016 | Zhou et al. | |
| 2017/0112878 A1 | 4/2017 | Kaufmann et al. | |
| 2019/0135937 A1 | 5/2019 | Zhang et al. | |

FOREIGN PATENT DOCUMENTS

| | | |
|---|---|---|
| WO | 2016168493 A1 | 10/2016 |
| WO | 2016187158 A1 † | 11/2016 |
| WO | 2017070608 A1 | 4/2017 |
| WO | 2017165464 A1 | 9/2017 |
| WO | 2019087151 A1 | 5/2019 |
| WO | 2019122060 A1 | 6/2019 |
| WO | 2019192972 A1 | 10/2019 |
| WO | 2019192973 A1 | 10/2019 |

OTHER PUBLICATIONS

Van de Donk, Niels WCJ, et al. "Monoclonal antibodies targeting CD 38 in hematological malignancies and beyond." Immunological reviews 270.1 (2016): 95-112. (Year: 2016).*
Nolan et al., Bypassing Immunization: Optimized Design of "Designer T cells" against Carcinoembryonic Antigen (CEA)-expressing Tumors, and Lack of Suppression by Soluble CEA, Clinical Cancer Research, 5: 3928-3941 (1999).
Szymczak et al., Correction of multi-gene deficiency in vivo using a single 'self-cleaving' 2A peptide-based retroviral vector, Nature Biotechnology, 22(5): 589-594 (2004).
Anonymous, Communication Pursuant to Rule 114(2) EPC (Third Party Observation) in EP Application No. 19764893.4, mailed Oct. 20, 2022 (3 pages).
Drent et al., "A Rational Strategy for Reducing On-Target Off-Tumor Effects of CD38-Chimeric Antigen Receptors by Affinity Optimization," Molecular Therapy, 25(8): 1946-1958 (2017).
Extended European Search Report received in European Patent Application No. 19764893.4, mailed Feb. 11, 2022, 4 pages.
Gao et al., "Blocking CD38-driven fratricide among T cells enables effective antitumor activity by CD38-specific chimeric antigen receptor T cells," Journal of Genetics and Genomics, 46(8): 367-377 (2019).
Beecham et al., "Coupling CD28 Co-Stimulation to Immunoglobulin T-Cell Receptor Molecules: The Dynamics of T-Cell Proliferation and Death," J. Immunother. 23(6): 631-642, 2000.
Emtage et al., "Second-Generation Anti-Carcinoembryonic Antigen Designer T Cells Resist Activation-Induced Cell Death, Proliferate on Tumor Contact, Secrete Cytokines, and Exhibit Superior Antitumor Activity In vivo: A Preclinical Evaluation," Clin. Cancer Res. 14(24): 8112-8122, 2008.

(Continued)

*Primary Examiner* — Robert J Yamasaki
(74) *Attorney, Agent, or Firm* — McNeill PLLC

(57) ABSTRACT

The present disclosure provides dimeric antigen receptors (DAR) constructs comprising a heavy chain binding region on one polypeptide chain and a light chain binding region on a separate polypeptide chain. The two polypeptide chains that make up the dimeric antigen receptors can dimerize to form an antigen binding domain. The dimeric antigen receptors have antibody-like properties as they bind specifically to a target antigen. The dimeric antigen receptors can be used for directed cell therapy.

10 Claims, 38 Drawing Sheets

Specification includes a Sequence Listing.

(56) References Cited

OTHER PUBLICATIONS

Eshhar et al., "Specific activation and targeting of cytotoxic lymphocytes through chimeric single chains consisting of antibody-binding domains and the y or C subunits of the immunoglobulin and T-cell receptors," Proc. Natl. Acad. Sci. U S A 90(2): 720-724, 1993.

Faitschuk et al. "A dual chain chimeric antigen receptor (CAR) in the native antibody format for targeting immune cells towards cancer cells without the need of an scFv" Gene Ther. Oct. 2016 Vol, 23 No. 10, pp. 718-726, especially, whole document.

Finney et al., "Chimeric Receptors Providing Both Primary and Costimulatory Signaling in T Cells from a Single Gene Product," J. Immunol. 161(6): 2791-2797, 1998.

Geiger et al., "The TCR ζ-Chain Immunoreceptor Tyrosine-Based Activation Motifs Are Sufficient for the Activation and Differentiation of Primary T Lymphocytes," J. Immunol. 162(10): 5931-5939, 1999.

Gerstmayer et al., "Costimulation of T cell proliferation by a chimeric B7-2 antibody fusion protein specifically targeted to cells expressing the erbB2 proto-oncogene," J. Immunol. 158(10): 4584-4590, 1997.

Haynes et al., "Redirecting Mouse CTL Against Colon Carcinoma: Superior Signaling Efficacy of Single-Chain Variable Domain Chimeras Containing TCR-z vs FceRI-g1," J. Immunol. 166(1): 182-187, 2001.

Hombach et al., "T-Cell Activation by Recombinant Receptors: CD28 Costimulation Is Required for Interleukin 2 Secretion and Receptor-mediated T-Cell Proliferation but Does Not Affect Receptor-mediated Target Cell Lysis," Cancer Res. 61(5): 1976-1982, 2001.

Hombach et al., "Tumor-Specific T Cell Activation by Recombinant Immunoreceptors: CD3 Signaling and CD28 Costimulation Are Simultaneously Required for Efficient IL-2 Secretion and Can Be Integrated Into One Combined CD28/CD3 Signaling Receptor Molecule," J. Immunol. 167(11): 6123-6131, 2001.

International Search Report corresponding to International Patent Application No. PCT/US2019/021681, mailed Jul. 25, 2019, 13 pages.

Junghans et al., "Phase I Trial of Anti-PSMA Designer CAR-T Cells in Prostate Cancer: Possible Role for Interacting Interleukin 2-T Cell Pharmacodynamics as a Determinant of Clinical Response," 2016, The Prostate, 76(14): 1257-1270.

Katz et al., "Phase I Hepatic Immunotherapy for Metastases Study of Intra-Arterial Chimeric Antigen Receptor-Modified T-cell Therapy for CEA Liver Metastases," Clin. Cancer Res. 21(14): 3149-3159, 2015.

Kong et al., "Suppression of Human Glioma Xenografts with Second-Generation IL 13R-Specific Chimeric Antigen Receptor-Modified T Cells," Clin. Cancer Res. 18(21): 5949-5960, 2012.

Lo, Ma et al., "Anti-GD3 Chimeric sFv-CD28/T-Cell Receptor Designer T Cells for Treatment of Metastatic Melanoma and Other Neuroectodermal Tumors," Clin. Cancer Res. 16(10): 2769-2780, 2010.

Ma et al., "Advanced Generation Anti-Prostate Specific Membrane Antigen Designer T Cells for Prostate Cancer Immunotherapy," Prostate 74(3): 286-296, 2014.

Ma et al., "Anti-Prostate Specific Membrane Antigen Designer TCells for Prostate Cancer Therapy," Prostate 61(1): 12-25, 2004.

Ma et al., "Carcinoembryonic antigen-immunoglobulin Fc fusion protein (CEA-Fc) for identification and activation of anti-CEA immunoglobulin-T-cell receptor-modified T cells, representative of a new class of Ig fusion proteins," Cancer Gene Ther. 11(4): 297-306, 2004.

Maher et al., "Human T-lymphocyte cytotoxicity and proliferation directed by a single chimeric TCRζ/CD28 receptor," Nat. Biotechnol. 20(1): 70-75, 2002.

\* cited by examiner
† cited by third party

CD38-A2 DAR (2nd gen) amino acid sequences

Anti-CD38: heavy chain variable region: SEQ ID NO:1
QVQLVESGGGLVKPGGSLRLSCAASGFTFSDDYMSWIRQAPGKGLEWVASVSNGRPTT
YYADSVRGRFTISRDNAKNSLYLQMNSLRAEDTAVYYCAREDWGGEFTDWGRGTLVT
VSS

Anti-CD38: heavy chain constant: SEQ ID NO:2
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHT

Anti-CD38: light chain variable: SEQ ID NO:3
QSVLTQPPSASGTSGQRVTISCSGSSSNIGINFVYWYQHLPGTAPKLLIYKNNQRPSGVPD
RFSGSKSGNSASLAISGLRSEDEADYYCAAWDDSLSGYVFGSGTKVTVL

Anti-CD38: light chain constant: SEQ ID NO:4
GQPKAAPSVTLFPPSSEELQANKATLVCLISDFYPGAVTVAWKADSSPVKAGVETTTPS
KQSNNKYAASSYLSLTPEQWKSHRSYSCQVTHEGSTVEKTVAPTECS

CD28 hinge (short): SEQ ID NO:5
KIEVMYPPPYLDNEKSNGTIIHVKGKHLCPSPLFPGPSKP

CD28: transmembrane: SEQ ID NO:6
FWVLVVVGGVLACYSLLVTVAFIIFWV

4-1BB signaling region: SEQ ID NO:7
KRGRKKLLYIFKQPFMRPVQTTQEEDGCSCRFPEEEEGGCEL

CD28 signaling region: SEQ ID NO:8
RSKRSRLLHSDYMNMTPRRPGPTRKHYQPYAPPRDFAAYRS

CD3zeta signaling region: SEQ ID NO:9
RVKFSRSADAPAYQQGQNQLYNELNLGRREEYDVLDKRRGRDPEMGGKPRRKNPQEG
LYNELQKDKMAEAYSEIGMKGERRRGKGHDGLYQGLSTATKDTYDALHMQALPPR

Heavy chain leader sequence: SEQ ID NO:10
MEWSWVFLFFLSVTTGVHS

Light chain leader sequence: SEQ ID NO:11
MSVPTQVLGLLLLWLTDARC

T2A cleavage region: SEQ ID NO:12
GSGEGRGSLLTCGDVEENPGP

FIG. 35A

Anti-CD38: first polypeptide (V2a): SEQ ID NO:13

MEWSWVFLFFLSVTTGVHSQVQLVESGGGLVKPGGSLRLSCAASGFTFSDDYMSWIRQ
APGKGLEWVASVSNGRPTTYYADSVRGRFTISRDNAKNSLYLQMNSLRAEDTAVYYCA
REDWGGEFTDWGRGTLVTVSSASTKGPSVFPLAPSSKSTSGGTAALGCLVKDYFPEPVT
VSWNSGALTSGVHTFPAVLQSSGLYSLSSVVTVPSSSLGTQTYICNVNHKPSNTKVDKR
VEPKSCDKTHTKIEVMYPPPYLDNEKSNGTIIHVKGKHLCPSPLFPGPSKPFWVLVVGG
VLACYSLLVTVAFIIFWVKRGRKKLLYIFKQPFMRPVQTTQEEDGCSCRFPEEEEGGCEL
RVKFSRSADAPAYQQGQNQLYNELNLGRREEYDVLDKRRGRDPEMGGKPRRKNPQEG
LYNELQKDKMAEAYSEIGMKGERRRGKGHDGLYQGLSTATKDTYDALHMQALPPR

Anti-CD38: second polypeptide (V2a): SEQ ID NO:14

MSVPTQVLGLLLLWLTDARCQSVLTQPPSASGTSGQRVTISCSGSSSNIGINFVYWYQHL
PGTAPKLLIYKNNQRPSGVPDRFSGSKSGNSASLAISGLRSEDEADYYCAAWDDSLSGY
VFGSGTKVTVLGQPKAAPSVTLFPPSSEELQANKATLVCLISDFYPGAVTVAWKADSSP
VKAGVETTTPSKQSNNKYAASSYLSLTPEQWKSHRSYSCXVTHEGSTVEKTVAPTECS

Anti-CD38 2nd-gen DAR (V2a) precursor: SEQ ID NO:15

MEWSWVFLFFLSVTTGVHSQVQLVESGGGLVKPGGSLRLSCAASGFTFSDDYMSWIRQ
APGKGLEWVASVSNGRPTTYYADSVRGRFTISRDNAKNSLYLQMNSLRAEDTAVYYCA
REDWGGEFTDWGRGTLVTVSSASTKGPSVFPLAPSSKSTSGGTAALGCLVKDYFPEPVT
VSWNSGALTSGVHTFPAVLQSSGLYSLSSVVTVPSSSLGTQTYICNVNHKPSNTKVDKR
VEPKSCDKTHTKIEVMYPPPYLDNEKSNGTIIHVKGKHLCPSPLFPGPSKPFWVLVVGG
VLACYSLLVTVAFIIFWVKRGRKKLLYIFKQPFMRPVQTTQEEDGCSCRFPEEEEGGCEL
RVKFSRSADAPAYQQGQNQLYNELNLGRREEYDVLDKRRGRDPEMGGKPRRKNPQEG
LYNELQKDKMAEAYSEIGMKGERRRGKGHDGLYQGLSTATKDTYDALHMQALPPRGS
GEGRGSLLTCGDVEENPGPMSVPTQVLGLLLLWLTDARCQSVLTQPPSASGTSGQRVTI
SCSGSSSNIGINFVYWYQHLPGTAPKLLIYKNNQRPSGVPDRFSGSKSGNSASLAISGLRS
EDEADYYCAAWDDSLSGYVFGSGTKVTVLGQPKAAPSVTLFPPSSEELQANKATLVCLI
SDFYPGAVTVAWKADSSPVKAGVETTTPSKQSNNKYAASSYLSLTPEQWKSHRSYSCX
VTHEGSTVEKTVAPTECS

FIG. 35B

Anti-CD38: first polypeptide (V3): SEQ ID NO:16

MEWSWVFLFFLSVTTGVHSQVQLVESGGGLVKPGGSLRLSCAASGFTFSDDYMSWIRQ
APGKGLEWVASVSNGRPTTYYADSVRGRFTISRDNAKNSLYLQMNSLRAEDTAVYYCA
REDWGGEFTDWGRGTLVTVSSASTKGPSVFPLAPSSKSTSGGTAALGCLVKDYFPEPVT
VSWNSGALTSGVHTFPAVLQSSGLYSLSSVVTVPSSSLGTQTYICNVNHKPSNTKVDKR
VEPKSCDKTHTKIEVMYPPPYLDNEKSNGTIIHVKGKHLCPSPLFPGPSKPFWVLVVVGG
VLACYSLLVTVAFIIFWVKRGRKKLLYIFKQPFMRPVQTTQEEDGCSCRFPEEEEGGCEL
RVKFSRSADKGERRRGKGHDGLYQGLSTATKDTYDALHMQALPPR

Anti-CD38: second polypeptide (V3): SEQ ID NO:17

MSVPTQVLGLLLLWLTDARCQSVLTQPPSASGTSGQRVTISCSGSSSNIGINFVYWYQHL
PGTAPKLLIYKNNQRPSGVPDRFSGSKSGNSASLAISGLRSEDEADYYCAAWDDSLSGY
VFGSGTKVTVLGQPKAAPSVTLFPPSSEELQANKATLVCLISDFYPGAVTVAWKADSSP
VKAGVETTTPSKQSNNKYAASSYLSLTPEQWKSHRSYSCXVTHEGSTVEKTVAPTECS

Anti-CD38 2<sup>nd</sup> gen DAR (V3) precursor: SEQ ID NO:18

MEWSWVFLFFLSVTTGVHSQVQLVESGGGLVKPGGSLRLSCAASGFTFSDDYMSWIRQ
APGKGLEWVASVSNGRPTTYYADSVRGRFTISRDNAKNSLYLQMNSLRAEDTAVYYCA
REDWGGEFTDWGRGTLVTVSSASTKGPSVFPLAPSSKSTSGGTAALGCLVKDYFPEPVT
VSWNSGALTSGVHTFPAVLQSSGLYSLSSVVTVPSSSLGTQTYICNVNHKPSNTKVDKR
VEPKSCDKTHTKIEVMYPPPYLDNEKSNGTIIHVKGKHLCPSPLFPGPSKPFWVLVVVGG
VLACYSLLVTVAFIIFWVKRGRKKLLYIFKQPFMRPVQTTQEEDGCSCRFPEEEEGGCEL
RVKFSRSADKGERRRGKGHDGLYQGLSTATKDTYDALHMQALPPRGSGEGRGSLLTCG
DVEENPGPMSVPTQVLGLLLLWLTDARCQSVLTQPPSASGTSGQRVTISCSGSSSNIGINF
VYWYQHLPGTAPKLLIYKNNQRPSGVPDRFSGSKSGNSASLAISGLRSEDEADYYCAA
WDDSLSGYVFGSGTKVTVLGQPKAAPSVTLFPPSSEELQANKATLVCLISDFYPGAVTV
AWKADSSPVKAGVETTTPSKQSNNKYAASSYLSLTPEQWKSHRSYSCXVTHEGSTVEK
TVAPTECS

FIG. 35C

Long hinge sequence: CD8 and CD28 hinge sequences: SEQ ID NO:19

AKPTTTPAPRPPTPAPTIASQPLSLRPEACRPAAGGAVHTRGLDFAPRKIEVMYPPPYLD
NEKSNGTIIHVKGKHLCPSPLFPGPSKP

CD3-zeta signaling region (ITAM 3): SEQ ID NO:20

RVKFSRSADKGERRRGKGHDGLYQGLSTATKDTYDALHMQALPPR

CD8 hinge: SEQ ID NO:21

AKPTTTPAPRPPTPAPTIASQPLSLRPEACRPAAGGAVHTRGLDFAPR

Anti-CD38 chimeric antigen receptor (CAR) construct: SEQ ID NO:22

MEWSWVFLFFLSVTTGVHSDIEQKLISEEDLQVQLVESGGGLVKPGGSLRLSCAASGFTF
SDDYMSWIRQAPGKGLEWVASVSNGRPTTYYADSVRGRFTISRDNAKNSLYLQMNSLR
AEDTAVYYCAREDWGGEFTDWGRGTLVTSSGGGGSGGGGSGGGGSQAGLTQPPSAS
GTSGQRVTISCSGSSSNIGINFVYWYQHLPGTAPKLLIYKNNQRPSGVPDRFSGSKSGNS
ASLAISGLRSEDEADYYCAAWDDSLSGYVFGSGTKVTVLAKPTTTPAPRPPTPAPTIASQ
PLSLRPEACRPAAGGAVHTRGLDFAKIEVMYPPPYLDNEKSNGTIIHVKGKHLCPSPLFP
GPSKPFWVLVVVGGVLACYSLLVTVAFIIFWVRSKRSRLLHSDYMNMTPRRPGPTRKH
YQPYAPPRDFAAYRSRVKFSRSADAPAYQQGQNQLYNELNLGRREEYDVLDKRRGRDP
EMGGKPQRRKNPQEGLYNELQKDKMAEAYSEIGMKGERRRGKGHDGLYQGLSTATKD
TYDALHMQALPPR

FIG. 35D

SEQUENCE LISTING

<160> NUMBER OF SEQ ID NOS: 24

<210> SEQ ID NO 1
<211> LENGTH: 118
<212> TYPE: PRT
<213> ORGANISM: Artificial Sequence
<220> FEATURE:
<223> OTHER INFORMATION: Anti-CD38: heavy chain variable region

<400> SEQUENCE: 1

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Asp
            20                  25                  30

Tyr Met Ser Trp Ile Arg Gln Ala Pro Gly Lys Gly Leu Glu Trp Val
        35                  40                  45

Ala Ser Val Ser Asn Gly Arg Pro Thr Thr Tyr Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Trp Gly Gly Glu Phe Thr Asp Trp Gly Arg Gly Thr
            100                 105                 110

Leu Val Thr Val Ser Ser
            115
```

<210> SEQ ID NO 2
<211> LENGTH: 108
<212> TYPE: PRT
<213> ORGANISM: Artificial Sequence
<220> FEATURE:
<223> OTHER INFORMATION: Anti-CD38: heavy chain constant

<400> SEQUENCE: 2

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr
            100                 105
```

<210> SEQ ID NO 3
<211> LENGTH: 110
<212> TYPE: PRT
<213> ORGANISM: Artificial Sequence
<220> FEATURE:
<223> OTHER INFORMATION: Anti-CD38: light chain variable

<400> SEQUENCE: 3

```
Gln Ser Val Leu Thr Gln Pro Pro Ser Ala Ser Gly Thr Ser Gly Gln
1               5                   10                  15

Arg Val Thr Ile Ser Cys Ser Gly Ser Ser Asn Ile Gly Ile Asn
            20                  25                  30

Phe Val Tyr Trp Tyr Gln His Leu Pro Gly Thr Ala Pro Lys Leu Leu
        35                  40                  45
```

```
Ile Tyr Lys Asn Asn Gln Arg Pro Ser Gly Val Pro Asp Arg Phe Ser
    50                  55                  60

Gly Ser Lys Ser Gly Asn Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                 85                  90                  95

Ser Gly Tyr Val Phe Gly Ser Gly Thr Lys Val Thr Val Leu
            100                 105                 110

<210> SEQ ID NO 4
<211> LENGTH: 106
<212> TYPE: PRT
<213> ORGANISM: Artificial Sequence
<220> FEATURE:
<223> OTHER INFORMATION: Anti-CD38: light chain constant

<400> SEQUENCE: 4

Gly Gln Pro Lys Ala Ala Pro Ser Val Thr Leu Phe Pro Pro Ser Ser
 1               5                  10                  15

Glu Glu Leu Gln Ala Asn Lys Ala Thr Leu Val Cys Leu Ile Ser Asp
                 20                  25                  30

Phe Tyr Pro Gly Ala Val Thr Val Ala Trp Lys Ala Asp Ser Ser Pro
             35                  40                  45

Val Lys Ala Gly Val Glu Thr Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
            100                 105

<210> SEQ ID NO 5
<211> LENGTH: 40
<212> TYPE: PRT
<213> ORGANISM: Artificial Sequence
<220> FEATURE:
<223> OTHER INFORMATION: CD28 hinge (short)

<400> SEQUENCE: 5

Lys Ile Glu Val Met Tyr Pro Pro Pro Tyr Leu Asp Asn Glu Lys Ser
 1               5                  10                  15

Asn Gly Thr Ile Ile His Val Lys Gly Lys His Leu Cys Pro Ser Pro
                 20                  25                  30

Leu Phe Pro Gly Pro Ser Lys Pro
            35                  40

<210> SEQ ID NO 6
<211> LENGTH: 27
<212> TYPE: PRT
<213> ORGANISM: Artificial Sequence
<220> FEATURE:
<223> OTHER INFORMATION: CD28: transmembrane

<400> SEQUENCE: 6

Phe Trp Val Leu Val Val Val Gly Gly Val Leu Ala Cys Tyr Ser Leu
 1               5                  10                  15

Leu Val Thr Val Ala Phe Ile Ile Phe Trp Val
                 20                  25
```

```
<210> SEQ ID NO 7
<211> LENGTH: 42
<212> TYPE: PRT
<213> ORGANISM: Artificial Sequence
<220> FEATURE:
<223> OTHER INFORMATION: 4-1BB signaling region

<400> SEQUENCE: 7

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 8
<211> LENGTH: 41
<212> TYPE: PRT
<213> ORGANISM: Artificial Sequence
<220> FEATURE:
<223> OTHER INFORMATION: CD28 signaling region

<400> SEQUENCE: 8

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 9
<211> LENGTH: 112
<212> TYPE: PRT
<213> ORGANISM: Artificial Sequence
<220> FEATURE:
<223> OTHER INFORMATION: CD3zeta signaling region

<400> SEQUENCE: 9

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 10
<211> LENGTH: 19
<212> TYPE: PRT
<213> ORGANISM: Artificial Sequence
<220> FEATURE:
<223> OTHER INFORMATION: Heavy chain leader sequence
```

<400> SEQUENCE: 10

Met Glu Trp Ser Trp Val Phe Leu Phe Phe Leu Ser Val Thr Thr Gly
1               5                   10                  15

Val His Ser

<210> SEQ ID NO 11
<211> LENGTH: 20
<212> TYPE: PRT
<213> ORGANISM: Artificial Sequence
<220> FEATURE:
<223> OTHER INFORMATION: Light chain leader sequence

<400> SEQUENCE: 11

Met Ser Val Pro Thr Gln Val Leu Gly Leu Leu Leu Leu Trp Leu Thr
1               5                   10                  15

Asp Ala Arg Cys
            20

<210> SEQ ID NO 12
<211> LENGTH: 21
<212> TYPE: PRT
<213> ORGANISM: Artificial Sequence
<220> FEATURE:
<223> OTHER INFORMATION: T2A cleavage region

<400> SEQUENCE: 12

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 13
<211> LENGTH: 466
<212> TYPE: PRT
<213> ORGANISM: Artificial Sequence
<220> FEATURE:
<223> OTHER INFORMATION: Anti-CD38: first polypeptide (V2a)

<400> SEQUENCE: 13

Met Glu Trp Ser Trp Val Phe Leu Phe Phe Leu Ser Val Thr Thr Gly
1               5                   10                  15

Val His Ser Gln Val Gln Leu Val Glu Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Asp Asp Tyr Met Ser Trp Ile Arg Gln Ala Pro Gly Lys Gly Leu
    50                  55                  60

Glu Trp Val Ala Ser Val Ser Asn Gly Arg Pro Thr Thr Tyr Tyr Ala
65                  70                  75                  80

Asp Ser Val Arg Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Arg Glu Asp Trp Gly Glu Phe Thr Asp Trp Gly
        115                 120                 125

Arg Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Arg Val Glu Pro Lys Ser Cys
225                 230                 235                 240

Asp Lys Thr His Thr Lys Ile Glu Val Met Tyr Pro Pro Pro Tyr Leu
                245                 250                 255

Asp Asn Glu Lys Ser Asn Gly Thr Ile Ile His Val Lys Gly Lys His
            260                 265                 270

Leu Cys Pro Ser Pro Leu Phe Pro Gly Pro Ser Lys Pro Phe Trp Val
        275                 280                 285

Leu Val Val Val Gly Gly Val Leu Ala Cys Tyr Ser Leu Leu Val Thr
    290                 295                 300

Val Ala Phe Ile Ile Phe Trp Val Lys Arg Gly Arg Lys Lys Leu Leu
305                 310                 315                 320

Tyr Ile Phe Lys Gln Pro Phe Met Arg Pro Val Gln Thr Thr Gln Glu
                325                 330                 335

Glu Asp Gly Cys Ser Cys Arg Phe Pro Glu Glu Glu Glu Gly Gly Cys
            340                 345                 350

Glu Leu Arg Val Lys Phe Ser Arg Ser Ala Asp Ala Pro Ala Tyr Gln
        355                 360                 365

Gln Gly Gln Asn Gln Leu Tyr Asn Glu Leu Asn Leu Gly Arg Arg Glu
    370                 375                 380

Glu Tyr Asp Val Leu Asp Lys Arg Arg Gly Arg Asp Pro Glu Met Gly
385                 390                 395                 400

Gly Lys Pro Arg Arg Lys Asn Pro Gln Glu Gly Leu Tyr Asn Glu Leu
                405                 410                 415

Gln Lys Asp Lys Met Ala Glu Ala Tyr Ser Glu Ile Gly Met Lys Gly
            420                 425                 430

Glu Arg Arg Arg Gly Lys Gly His Asp Gly Leu Tyr Gln Gly Leu Ser
        435                 440                 445

Thr Ala Thr Lys Asp Thr Tyr Asp Ala Leu His Met Gln Ala Leu Pro
    450                 455                 460

Pro Arg
465

<210> SEQ ID NO 14
<211> LENGTH: 236
<212> TYPE: PRT
<213> ORGANISM: Artificial Sequence
<220> FEATURE:
<223> OTHER INFORMATION: Anti-CD38: second polypeptide (V2a)
<220> FEATURE:
<221> NAME/KEY: misc_feature
<222> LOCATION: (218)..(218)
<223> OTHER INFORMATION: Xaa can be any naturally occurring amino acid

<400> SEQUENCE: 14

Met Ser Val Pro Thr Gln Val Leu Gly Leu Leu Leu Leu Trp Leu Thr
1               5                   10                  15

```
Asp Ala Arg Cys Gln Ser Val Leu Thr Gln Pro Ser Ala Ser Gly
             20                  25                  30

Thr Ser Gly Gln Arg Val Thr Ile Ser Cys Ser Gly Ser Ser Ser Asn
         35                  40                  45

Ile Gly Ile Asn Phe Val Tyr Trp Tyr Gln His Leu Pro Gly Thr Ala
 50                  55                  60

Pro Lys Leu Leu Ile Tyr Lys Asn Asn Gln Arg Pro Ser Gly Val Pro
 65                  70                  75                  80

Asp Arg Phe Ser Gly Ser Lys Ser Gly Asn Ser Ala Ser Leu Ala Ile
             85                  90                  95

Ser Gly Leu Arg Ser Glu Asp Glu Ala Asp Tyr Tyr Cys Ala Ala Trp
            100                 105                 110

Asp Asp Ser Leu Ser Gly Tyr Val Phe Gly Ser Gly Thr Lys Val Thr
            115                 120                 125

Val Leu Gly Gln Pro Lys Ala Ala Pro Ser Val Thr Leu Phe Pro Pro
130                 135                 140

Ser Ser Glu Glu Leu Gln Ala Asn Lys Ala Thr Leu Val Cys Leu Ile
145                 150                 155                 160

Ser Asp Phe Tyr Pro Gly Ala Val Thr Val Ala Trp Lys Ala Asp Ser
                165                 170                 175

Ser Pro Val Lys Ala Gly Val Glu Thr Thr Thr Pro Ser Lys Gln Ser
            180                 185                 190

Asn Asn Lys Tyr Ala Ala Ser Ser Tyr Leu Ser Leu Thr Pro Glu Gln
            195                 200                 205

Trp Lys Ser His Arg Ser Tyr Ser Cys Xaa Val Thr His Glu Gly Ser
        210                 215                 220

Thr Val Glu Lys Thr Val Ala Pro Thr Glu Cys Ser
225                 230                 235

<210> SEQ ID NO 15
<211> LENGTH: 723
<212> TYPE: PRT
<213> ORGANISM: Artificial Sequence
<220> FEATURE:
<223> OTHER INFORMATION: Anti-CD38 2nd gen DAR (V2a) precursor
<220> FEATURE:
<221> NAME/KEY: misc_feature
<222> LOCATION: (705)..(705)
<223> OTHER INFORMATION: Xaa can be any naturally occurring amino acid

<400> SEQUENCE: 15

Met Glu Trp Ser Trp Val Phe Leu Phe Phe Leu Ser Val Thr Thr Gly
 1               5                  10                  15

Val His Ser Gln Val Gln Leu Val Glu Ser Gly Gly Gly Leu Val Lys
             20                  25                  30

Pro Gly Gly Ser Leu Arg Leu Ser Cys Ala Ala Ser Gly Phe Thr Phe
         35                  40                  45

Ser Asp Asp Tyr Met Ser Trp Ile Arg Gln Ala Pro Gly Lys Gly Leu
 50                  55                  60

Glu Trp Val Ala Ser Val Ser Asn Gly Arg Pro Thr Tyr Tyr Ala
 65                  70                  75                  80

Asp Ser Val Arg Gly Arg Phe Thr Ile Ser Arg Asp Asn Ala Lys Asn
             85                  90                  95

Ser Leu Tyr Leu Gln Met Asn Ser Leu Arg Ala Glu Asp Thr Ala Val
            100                 105                 110
```

```
Tyr Tyr Cys Ala Arg Glu Asp Trp Gly Gly Glu Phe Thr Asp Trp Gly
        115                 120                 125

Arg Gly Thr Leu Val Thr Val Ser Ser Ala Ser Thr Lys Gly Pro Ser
        130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
                180                 185                 190

Val Leu Gln Ser Ser Gly Leu Tyr Ser Leu Ser Ser Val Val Thr Val
                195                 200                 205

Pro Ser Ser Ser Leu Gly Thr Gln Thr Tyr Ile Cys Asn Val Asn His
        210                 215                 220

Lys Pro Ser Asn Thr Lys Val Asp Lys Arg Val Glu Pro Lys Ser Cys
225                 230                 235                 240

Asp Lys Thr His Thr Lys Ile Glu Val Met Tyr Pro Pro Pro Tyr Leu
                245                 250                 255

Asp Asn Glu Lys Ser Asn Gly Thr Ile Ile His Val Lys Gly Lys His
                260                 265                 270

Leu Cys Pro Ser Pro Leu Phe Pro Gly Pro Ser Lys Pro Phe Trp Val
        275                 280                 285

Leu Val Val Val Gly Gly Val Leu Ala Cys Tyr Ser Leu Leu Val Thr
        290                 295                 300

Val Ala Phe Ile Ile Phe Trp Val Lys Arg Gly Arg Lys Lys Leu Leu
305                 310                 315                 320

Tyr Ile Phe Lys Gln Pro Phe Met Arg Pro Val Gln Thr Thr Gln Glu
                325                 330                 335

Glu Asp Gly Cys Ser Cys Arg Phe Pro Glu Glu Glu Glu Gly Gly Cys
                340                 345                 350

Glu Leu Arg Val Lys Phe Ser Arg Ser Ala Asp Ala Pro Ala Tyr Gln
        355                 360                 365

Gln Gly Gln Asn Gln Leu Tyr Asn Glu Leu Asn Leu Gly Arg Arg Glu
        370                 375                 380

Glu Tyr Asp Val Leu Asp Lys Arg Arg Gly Arg Asp Pro Glu Met Gly
385                 390                 395                 400

Gly Lys Pro Arg Arg Lys Asn Pro Gln Glu Gly Leu Tyr Asn Glu Leu
                405                 410                 415

Gln Lys Asp Lys Met Ala Glu Ala Tyr Ser Glu Ile Gly Met Lys Gly
                420                 425                 430

Glu Arg Arg Arg Gly Lys Gly His Asp Gly Leu Tyr Gln Gly Leu Ser
        435                 440                 445

Thr Ala Thr Lys Asp Thr Tyr Asp Ala Leu His Met Gln Ala Leu Pro
        450                 455                 460

Pro Arg Gly Ser Gly Glu Gly Arg Gly Ser Leu Leu Thr Cys Gly Asp
465                 470                 475                 480

Val Glu Glu Asn Pro Gly Pro Met Ser Val Pro Thr Gln Val Leu Gly
                485                 490                 495

Leu Leu Leu Leu Trp Leu Thr Asp Ala Arg Cys Gln Ser Val Leu Thr
                500                 505                 510

Gln Pro Pro Ser Ala Ser Gly Thr Ser Gly Gln Arg Val Thr Ile Ser
        515                 520                 525
```

```
Cys Ser Gly Ser Ser Asn Ile Gly Ile Asn Phe Val Tyr Trp Tyr
    530                 535                 540

Gln His Leu Pro Gly Thr Ala Pro Lys Leu Leu Ile Tyr Lys Asn Asn
545                 550                 555                 560

Gln Arg Pro Ser Gly Val Pro Asp Arg Phe Ser Gly Ser Lys Ser Gly
                565                 570                 575

Asn Ser Ala Ser Leu Ala Ile Ser Gly Leu Arg Ser Glu Asp Glu Ala
            580                 585                 590

Asp Tyr Tyr Cys Ala Ala Trp Asp Asp Ser Leu Ser Gly Tyr Val Phe
        595                 600                 605

Gly Ser Gly Thr Lys Val Thr Val Leu Gly Gln Pro Lys Ala Ala Pro
    610                 615                 620

Ser Val Thr Leu Phe Pro Pro Ser Ser Glu Glu Leu Gln Ala Asn Lys
625                 630                 635                 640

Ala Thr Leu Val Cys Leu Ile Ser Asp Phe Tyr Pro Gly Ala Val Thr
                645                 650                 655

Val Ala Trp Lys Ala Asp Ser Ser Pro Val Lys Ala Gly Val Glu Thr
            660                 665                 670

Thr Thr Pro Ser Lys Gln Ser Asn Asn Lys Tyr Ala Ala Ser Ser Tyr
        675                 680                 685

Leu Ser Leu Thr Pro Glu Gln Trp Lys Ser His Arg Ser Tyr Ser Cys
    690                 695                 700

Xaa Val Thr His Glu Gly Ser Thr Val Glu Lys Thr Val Ala Pro Thr
705                 710                 715                 720

Glu Cys Ser

<210> SEQ ID NO 16
<211> LENGTH: 399
<212> TYPE: PRT
<213> ORGANISM: Artificial Sequence
<220> FEATURE:
<223> OTHER INFORMATION: Anti-CD38: first polypeptide (V3)

<400> SEQUENCE: 16

Met Glu Trp Ser Trp Val Phe Leu Phe Phe Leu Ser Val Thr Thr Gly
1               5                   10                  15

Val His Ser Gln Val Gln Leu Val Glu Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Asp Asp Tyr Met Ser Trp Ile Arg Gln Ala Pro Gly Lys Gly Leu
    50                  55                  60

Glu Trp Val Ala Ser Val Ser Asn Gly Arg Pro Thr Thr Tyr Tyr Ala
65                  70                  75                  80

Asp Ser Val Arg Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Arg Glu Asp Trp Gly Gly Phe Thr Asp Trp Gly
        115                 120                 125

Arg Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160
```

```
Ala Leu Gly Cys Leu Val Lys Asp Tyr Phe Pro Glu Pro Val Thr Val
            165                 170                 175

Ser Trp Asn Ser Gly Ala Leu Thr Ser Gly Val His Thr Phe Pro Ala
        180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
210                 215                 220

Lys Pro Ser Asn Thr Lys Val Asp Lys Arg Val Glu Pro Lys Ser Cys
225                 230                 235                 240

Asp Lys Thr His Thr Lys Ile Glu Val Met Tyr Pro Pro Pro Tyr Leu
            245                 250                 255

Asp Asn Glu Lys Ser Asn Gly Thr Ile Ile His Val Lys Gly Lys His
            260                 265                 270

Leu Cys Pro Ser Pro Leu Phe Pro Gly Pro Ser Lys Pro Phe Trp Val
        275                 280                 285

Leu Val Val Gly Gly Val Leu Ala Cys Tyr Ser Leu Leu Val Thr
        290                 295                 300

Val Ala Phe Ile Ile Phe Trp Val Lys Arg Gly Arg Lys Lys Leu Leu
305                 310                 315                 320

Tyr Ile Phe Lys Gln Pro Phe Met Arg Pro Val Gln Thr Thr Gln Glu
            325                 330                 335

Glu Asp Gly Cys Ser Cys Arg Phe Pro Glu Glu Glu Gly Gly Cys
            340                 345                 350

Glu Leu Arg Val Lys Phe Ser Arg Ser Ala Asp Lys Gly Glu Arg Arg
            355                 360                 365

Arg Gly Lys Gly His Asp Gly Leu Tyr Gln Gly Leu Ser Thr Ala Thr
        370                 375                 380

Lys Asp Thr Tyr Asp Ala Leu His Met Gln Ala Leu Pro Pro Arg
385                 390                 395

<210> SEQ ID NO 17
<211> LENGTH: 236
<212> TYPE: PRT
<213> ORGANISM: Artificial Sequence
<220> FEATURE:
<223> OTHER INFORMATION: Anti-CD38: second polypeptide (V3)
<220> FEATURE:
<221> NAME/KEY: misc_feature
<222> LOCATION: (218)..(218)
<223> OTHER INFORMATION: Xaa can be any naturally occurring amino acid

<400> SEQUENCE: 17

Met Ser Val Pro Thr Gln Val Leu Gly Leu Leu Leu Leu Trp Leu Thr
1               5                   10                  15

Asp Ala Arg Cys Gln Ser Val Leu Thr Gln Pro Pro Ser Ala Ser Gly
            20                  25                  30

Thr Ser Gly Gln Arg Val Thr Ile Ser Cys Ser Gly Ser Ser Ser Asn
        35                  40                  45

Ile Gly Ile Asn Phe Val Tyr Trp Tyr Gln His Leu Pro Gly Thr Ala
    50                  55                  60

Pro Lys Leu Leu Ile Tyr Lys Asn Asn Gln Arg Pro Ser Gly Val Pro
65                  70                  75                  80

Asp Arg Phe Ser Gly Ser Lys Ser Gly Asn Ser Ala Ser Leu Ala Ile
                85                  90                  95
```

```
Ser Gly Leu Arg Ser Glu Asp Glu Ala Asp Tyr Tyr Cys Ala Ala Trp
            100                 105                 110

Asp Asp Ser Leu Ser Gly Tyr Val Phe Gly Ser Gly Thr Lys Val Thr
            115                 120                 125

Val Leu Gly Gln Pro Lys Ala Ala Pro Ser Val Thr Leu Phe Pro Pro
        130                 135                 140

Ser Ser Glu Glu Leu Gln Ala Asn Lys Ala Thr Leu Val Cys Leu Ile
145                 150                 155                 160

Ser Asp Phe Tyr Pro Gly Ala Val Thr Val Ala Trp Lys Ala Asp Ser
                165                 170                 175

Ser Pro Val Lys Ala Gly Val Glu Thr Thr Thr Pro Ser Lys Gln Ser
            180                 185                 190

Asn Asn Lys Tyr Ala Ala Ser Ser Tyr Leu Ser Leu Thr Pro Glu Gln
        195                 200                 205

Trp Lys Ser His Arg Ser Tyr Ser Cys Xaa Val Thr His Glu Gly Ser
    210                 215                 220

Thr Val Glu Lys Thr Val Ala Pro Thr Glu Cys Ser
225                 230                 235

<210> SEQ ID NO 18
<211> LENGTH: 656
<212> TYPE: PRT
<213> ORGANISM: Artificial Sequence
<220> FEATURE:
<223> OTHER INFORMATION: Anti-CD38 2nd gen DAR (V3) precursor
<220> FEATURE:
<221> NAME/KEY: misc_feature
<222> LOCATION: (638)..(638)
<223> OTHER INFORMATION: Xaa can be any naturally occurring amino acid

<400> SEQUENCE: 18

Met Glu Trp Ser Trp Val Phe Leu Phe Phe Leu Ser Val Thr Thr Gly
1               5                   10                  15

Val His Ser Gln Val Gln Leu Val Glu Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Asp Asp Tyr Met Ser Trp Ile Arg Gln Ala Pro Gly Lys Gly Leu
    50                  55                  60

Glu Trp Val Ala Ser Val Ser Asn Gly Arg Pro Thr Thr Tyr Tyr Ala
65                  70                  75                  80

Asp Ser Val Arg Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Arg Glu Asp Trp Gly Gly Glu Phe Thr Asp Trp Gly
        115                 120                 125

Arg Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190
```

```
Val Leu Gln Ser Ser Gly Leu Tyr Ser Leu Ser Ser Val Val Thr Val
            195                 200                 205

Pro Ser Ser Ser Leu Gly Thr Gln Thr Tyr Ile Cys Asn Val Asn His
210                 215                 220

Lys Pro Ser Asn Thr Lys Val Asp Lys Arg Val Glu Pro Lys Ser Cys
225                 230                 235                 240

Asp Lys Thr His Thr Lys Ile Glu Val Met Tyr Pro Pro Tyr Leu
                245                 250                 255

Asp Asn Glu Lys Ser Asn Gly Thr Ile Ile His Val Lys Gly Lys His
                260                 265                 270

Leu Cys Pro Ser Pro Leu Phe Pro Gly Pro Ser Lys Pro Phe Trp Val
            275                 280                 285

Leu Val Val Gly Gly Val Leu Ala Cys Tyr Ser Leu Leu Val Thr
290                 295                 300

Val Ala Phe Ile Ile Phe Trp Val Lys Arg Gly Arg Lys Lys Leu Leu
305                 310                 315                 320

Tyr Ile Phe Lys Gln Pro Phe Met Arg Pro Val Gln Thr Thr Gln Glu
            325                 330                 335

Glu Asp Gly Cys Ser Cys Arg Phe Pro Glu Glu Glu Glu Gly Gly Cys
            340                 345                 350

Glu Leu Arg Val Lys Phe Ser Arg Ser Ala Asp Lys Gly Glu Arg Arg
            355                 360                 365

Arg Gly Lys Gly His Asp Gly Leu Tyr Gln Gly Leu Ser Thr Ala Thr
            370                 375                 380

Lys Asp Thr Tyr Asp Ala Leu His Met Gln Ala Leu Pro Pro Arg Gly
385                 390                 395                 400

Ser Gly Glu Gly Arg Gly Ser Leu Leu Thr Cys Gly Asp Val Glu Glu
            405                 410                 415

Asn Pro Gly Pro Met Ser Val Pro Thr Gln Val Leu Gly Leu Leu Leu
            420                 425                 430

Leu Trp Leu Thr Asp Ala Arg Cys Gln Ser Val Leu Thr Gln Pro Pro
            435                 440                 445

Ser Ala Ser Gly Thr Ser Gly Gln Arg Val Thr Ile Ser Cys Ser Gly
450                 455                 460

Ser Ser Ser Asn Ile Gly Ile Asn Phe Val Tyr Trp Tyr Gln His Leu
465                 470                 475                 480

Pro Gly Thr Ala Pro Lys Leu Leu Ile Tyr Lys Asn Asn Gln Arg Pro
            485                 490                 495

Ser Gly Val Pro Asp Arg Phe Ser Gly Ser Lys Ser Gly Asn Ser Ala
            500                 505                 510

Ser Leu Ala Ile Ser Gly Leu Arg Ser Glu Asp Glu Ala Asp Tyr Tyr
            515                 520                 525

Cys Ala Ala Trp Asp Asp Ser Leu Ser Gly Tyr Val Phe Gly Ser Gly
            530                 535                 540

Thr Lys Val Thr Val Leu Gly Gln Pro Lys Ala Ala Pro Ser Val Thr
545                 550                 555                 560

Leu Phe Pro Pro Ser Ser Glu Glu Leu Gln Ala Asn Lys Ala Thr Leu
            565                 570                 575

Val Cys Leu Ile Ser Asp Phe Tyr Pro Gly Ala Val Thr Val Ala Trp
            580                 585                 590

Lys Ala Asp Ser Ser Pro Val Lys Ala Gly Val Glu Thr Thr Pro
            595                 600                 605
```

```
Ser Lys Gln Ser Asn Asn Lys Tyr Ala Ala Ser Ser Tyr Leu Ser Leu
    610                 615                 620

Thr Pro Glu Gln Trp Lys Ser His Arg Ser Tyr Ser Cys Xaa Val Thr
625                 630                 635                 640

His Glu Gly Ser Thr Val Glu Lys Thr Val Ala Pro Thr Glu Cys Ser
                645                 650                 655

<210> SEQ ID NO 19
<211> LENGTH: 88
<212> TYPE: PRT
<213> ORGANISM: Artificial Sequence
<220> FEATURE:
<223> OTHER INFORMATION: Long hinge sequence: CD8 and CD28 hinge
      sequences

<400> SEQUENCE: 19

Ala Lys Pro Thr Thr Thr Pro Ala Pro Arg Pro Pro Thr Pro Ala Pro
1               5                   10                  15

Thr Ile Ala Ser Gln Pro Leu Ser Leu Arg Pro Glu Ala Cys Arg Pro
            20                  25                  30

Ala Ala Gly Gly Ala Val His Thr Arg Gly Leu Asp Phe Ala Pro Arg
        35                  40                  45

Lys Ile Glu Val Met Tyr Pro Pro Pro Tyr Leu Asp Asn Glu Lys Ser
    50                  55                  60

Asn Gly Thr Ile Ile His Val Lys Gly Lys His Leu Cys Pro Ser Pro
65                  70                  75                  80

Leu Phe Pro Gly Pro Ser Lys Pro
                85

<210> SEQ ID NO 20
<211> LENGTH: 45
<212> TYPE: PRT
<213> ORGANISM: Artificial Sequence
<220> FEATURE:
<223> OTHER INFORMATION: CD3-zeta signaling region (ITAM 3)

<400> SEQUENCE: 20

Arg Val Lys Phe Ser Arg Ser Ala Asp Lys Gly Glu Arg Arg Arg Gly
1               5                   10                  15

Lys Gly His Asp Gly Leu Tyr Gln Gly Leu Ser Thr Ala Thr Lys Asp
            20                  25                  30

Thr Tyr Asp Ala Leu His Met Gln Ala Leu Pro Pro Arg
        35                  40                  45

<210> SEQ ID NO 21
<211> LENGTH: 48
<212> TYPE: PRT
<213> ORGANISM: Artificial Sequence
<220> FEATURE:
<223> OTHER INFORMATION: CD8 hinge

<400> SEQUENCE: 21

Ala Lys Pro Thr Thr Thr Pro Ala Pro Arg Pro Pro Thr Pro Ala Pro
1               5                   10                  15

Thr Ile Ala Ser Gln Pro Leu Ser Leu Arg Pro Glu Ala Cys Arg Pro
            20                  25                  30

Ala Ala Gly Gly Ala Val His Thr Arg Gly Leu Asp Phe Ala Pro Arg
        35                  40                  45

<210> SEQ ID NO 22
<211> LENGTH: 541
```

<212> TYPE: PRT
<213> ORGANISM: Artificial Sequence
<220> FEATURE:
<223> OTHER INFORMATION: Anti-CD38 chimeric antigen receptor (CAR) construct

<400> SEQUENCE: 22

```
Met Glu Trp Ser Trp Val Phe Leu Phe Phe Leu Ser Val Thr Thr Gly
1               5                   10                  15

Val His Ser Asp Ile Glu Gln Lys Leu Ile Ser Glu Glu Asp Leu Gln
            20                  25                  30

Val Gln Leu Val Glu Ser Gly Gly Gly Leu Val Lys Pro Gly Gly Ser
        35                  40                  45

Leu Arg Leu Ser Cys Ala Ala Ser Gly Phe Thr Phe Ser Asp Asp Tyr
    50                  55                  60

Met Ser Trp Ile Arg Gln Ala Pro Gly Lys Gly Leu Glu Trp Val Ala
65                  70                  75                  80

Ser Val Ser Asn Gly Arg Pro Thr Thr Tyr Tyr Ala Asp Ser Val Arg
                85                  90                  95

Gly Arg Phe Thr Ile Ser Arg Asp Asn Ala Lys Asn Ser Leu Tyr Leu
            100                 105                 110

Gln Met Asn Ser Leu Arg Ala Glu Asp Thr Ala Val Tyr Tyr Cys Ala
        115                 120                 125

Arg Glu Asp Trp Gly Gly Glu Phe Thr Asp Trp Gly Arg Gly Thr Leu
    130                 135                 140

Val Thr Val Ser Ser Gly Gly Gly Ser Gly Gly Gly Ser Gly
145                 150                 155                 160

Gly Gly Ser Gln Ala Gly Leu Thr Gln Pro Ser Ala Ser Gly
                165                 170                 175

Thr Ser Gly Gln Arg Val Thr Ile Ser Cys Ser Gly Ser Ser Ser Asn
            180                 185                 190

Ile Gly Ile Asn Phe Val Tyr Trp Tyr Gln His Leu Pro Gly Thr Ala
        195                 200                 205

Pro Lys Leu Leu Ile Tyr Lys Asn Asn Gln Arg Pro Ser Gly Val Pro
    210                 215                 220

Asp Arg Phe Ser Gly Ser Lys Ser Gly Asn Ser Ala Ser Leu Ala Ile
225                 230                 235                 240

Ser Gly Leu Arg Ser Glu Asp Glu Ala Asp Tyr Tyr Cys Ala Ala Trp
                245                 250                 255

Asp Asp Ser Leu Ser Gly Tyr Val Phe Gly Ser Gly Thr Lys Val Thr
            260                 265                 270

Val Leu Ala Lys Pro Thr Thr Thr Pro Ala Pro Arg Pro Pro Thr Pro
        275                 280                 285

Ala Pro Thr Ile Ala Ser Gln Pro Leu Ser Leu Arg Pro Glu Ala Cys
    290                 295                 300

Arg Pro Ala Ala Gly Gly Ala Val His Thr Arg Gly Leu Asp Phe Ala
305                 310                 315                 320

Lys Ile Glu Val Met Tyr Pro Pro Pro Tyr Leu Asp Asn Glu Lys Ser
                325                 330                 335

Asn Gly Thr Ile Ile His Val Lys Gly Lys His Leu Cys Pro Ser Pro
            340                 345                 350

Leu Phe Pro Gly Pro Ser Lys Pro Phe Trp Val Leu Val Val Val Gly
        355                 360                 365

Gly Val Leu Ala Cys Tyr Ser Leu Leu Val Thr Val Ala Phe Ile Ile
    370                 375                 380
```

```
Phe Trp Val Arg Ser Lys Arg Ser Arg Leu Leu His Ser Asp Tyr Met
385                 390                 395                 400

Asn Met Thr Pro Arg Pro Gly Pro Thr Arg Lys His Tyr Gln Pro
                405             410                 415

Tyr Ala Pro Pro Arg Asp Phe Ala Ala Tyr Arg Ser Arg Val Lys Phe
            420                 425                 430

Ser Arg Ser Ala Asp Ala Pro Ala Tyr Gln Gln Gly Gln Asn Gln Leu
            435                 440                 445

Tyr Asn Glu Leu Asn Leu Gly Arg Arg Glu Glu Tyr Asp Val Leu Asp
            450                 455                 460

Lys Arg Arg Gly Arg Asp Pro Glu Met Gly Gly Lys Pro Gln Arg Arg
465                 470                 475                 480

Lys Asn Pro Gln Glu Gly Leu Tyr Asn Glu Leu Gln Lys Asp Lys Met
                485                 490                 495

Ala Glu Ala Tyr Ser Glu Ile Gly Met Lys Gly Glu Arg Arg Arg Gly
                500                 505                 510

Lys Gly His Asp Gly Leu Tyr Gln Gly Leu Ser Thr Ala Thr Lys Asp
            515                 520                 525

Thr Tyr Asp Ala Leu His Met Gln Ala Leu Pro Pro Arg
            530                 535                 540

<210> SEQ ID NO 23
<211> LENGTH: 15
<212> TYPE: PRT
<213> ORGANISM: Artificial Sequence
<220> FEATURE:
<223> OTHER INFORMATION: 15 amino acid linker

<400> SEQUENCE: 23

Gly Gly Gly Gly Ser Gly Gly Gly Gly Ser Gly Gly Gly Gly Ser
1               5                   10                  15

<210> SEQ ID NO 24
<211> LENGTH: 10
<212> TYPE: PRT
<213> ORGANISM: Artificial Sequence
<220> FEATURE:
<223> OTHER INFORMATION: Myc tag

<400> SEQUENCE: 24

Glu Gln Lys Leu Ile Ser Glu Glu Asp Leu
1               5                   10
```

DIMERIC ANTIGEN RECEPTORS

CROSS REFERENCE TO RELATED APPLICATIONS

This application is a continuation of International Patent Application No. PCT/US2019/021681, filed Mar. 11, 2019, which claims the benefit of priority to U.S. provisional application No. 62/640,775, filed Mar. 9, 2018, and entitled "Dimeric Antigen Receptors and Bivalent Antigen Receptors", the contents of each of which are incorporated herein by reference in their entirety.

Throughout this application various publications, patents, and/or patent applications are referenced. The disclosures of the publications, patents and/or patent applications are hereby incorporated by reference in their entireties into this application in order to more fully describe the state of the art to which this disclosure pertains.

SEQUENCE LISTING

The present application is filed with a Sequence Listing in electronic format. The Sequence Listing is provided as a file entitled "2024-03-29_01386-0015-00PCT_Replacement Seq_List_ST25" created on Mar. 29, 2024, which is 39,800 bytes in size. The information in the electronic format of the sequence listing is incorporated herein by reference in its entirety.

TECHNICAL FIELD

The present disclosure provides dimeric antigen receptors (DAR) protein constructs that bind specifically to a target antigen, nucleic acids that encode the dimeric antigen receptors, vectors comprising the nucleic acids, and host cells harboring the vectors.

BACKGROUND

Chimeric antigen receptors (CARs) have been developed to target antigens associated, in particular, with cancer. The first-generation CAR was engineered to contain a signaling domain (TCRζ) that delivers an activation stimulus (signal 1) only (Geiger et al., *J. Immunol.* 162 (10): 5931-5939, 1999; Haynes et al., *J. Immunol.* 166 (1): 182-187, 2001; Hombach et al. *Cancer Res.* 61 (5): 1976-1982, 2001; Hombach et al., *J. Immunol.* 167 (11): 6123-6131, 2001; Maher et al., *Nat. Biotechnol.* 20 (1): 70-75, 2002). T cells grafted with the first-generation CARs alone exhibited limited anti-tumor efficacy due to suboptimal activation (Beecham et al., *J. Immunother.* 23 (6): 631-642, 2000). The second-generation CAR, immunoglobulin-CD28-T cell receptor (IgCD28TCR), incorporated a costimulatory CD28 (signal 2) into the first-generation receptor (Gerstmayer et al., *J. Immunol.* 158 (10): 4584-4590, 1997; Emtage et al., *Clin. Cancer Res.* 14 (24): 8112-8122, 2008; Lo, Ma et al., *Clin. Cancer Res.* 16 (10): 2769-2780, 2010) that rendered the CAR-T cells a greater anti-tumor capacity (Finney et al., *J. Immunol.* 161 (6): 2791-2797, 1998; Hombach et al., *Cancer Res.* 61 (5): 1976-1982, 2001, Maher et al., *Nat. Biotechnol.* 20 (1): 70-75, 2002). Various CAR variants have been developed by replacing the signal domains of TCRζ or CD28 with molecules with similar functions, such as FcRγ, 4-1BB and OX40 (Eshhar et al., *Proc. Natl. Acad. Sci. USA* 90 (2): 720-724, 1993). TCR CAR-T cells against various tumor antigens have been developed (Ma et al., *Cancer Gene Ther.* 11 (4): 297-306, 2004; Ma et al., *Prostate* 61 (1): 12-25, 2004; Lo et al., *Clin. Cancer Res.* 16 (10): 2769-2780, 2010; Kong et al., *Clin. Cancer Res.* 18 (21): 5949-5960, 2012; Ma et al., *Prostate* 74 (3): 286-296, 2014; Katz et al., *Clin. Cancer Res.* 21 (14): 3149-3159, 2015; Junghans et al., 2016 *The Prostate,* 76 (14): 1257-1270).

Adoptive immunotherapy by infusion of T cells engineered with chimeric antigen receptors (CARs) for redirected tumoricidal activity represents a potentially highly specific modality for the treatment of metastatic cancer. CAR-T cells targeting CD19, a molecule expressed on B cells, have shown success in treatment of B cell malignancies and have received FDA approval, with some trials showing up to 70% of response, including sustained complete response.

Thus, there remains a need in the art to harness the powerful efficacy of CAR treatments with an antibody having both a heavy chain binding region and a light chain binding region in separate polypeptide chains antibody directed cell therapy. The present disclosure was made to satisfy this need in the art.

SUMMARY

The present disclosure provides dimeric antigen receptors (DAR) precursor polypeptide comprising ten regions ordered from the amino terminus to the carboxyl terminus: (1) a heavy chain leader sequence (2) an antibody heavy chain variable region, (3) an antibody heavy chain constant region, (4) an optional hinge region, (5) a transmembrane region, (6) an intracellular signaling region, (7) a T2A cleavage sequence, (8) a light chain leader sequence, (9) an antibody light chain variable region, and (10) an antibody light chain constant region.

The present disclosure provides dimeric antigen receptors (DAR) precursor polypeptide comprising ten regions ordered from the amino terminus to the carboxyl terminus: (1) a light chain leader sequence (2) an antibody light chain variable region, (3) an antibody light chain constant region, (4) an optional hinge region, (5) a transmembrane region, (6) an intracellular signaling region, (7) a T2A cleavage sequence, (8) a heavy chain leader sequence, (9) an antibody heavy chain variable region, and (10) an antibody heavy chain constant region.

In one embodiment, the precursor polypeptide optionally comprises a hinge sequence from an antibody selected from a group consisting of IgG, IgA, IgM, IgE and IgD. In one embodiment, the precursor polypeptide comprises a hinge sequence from a CD8a or CD28 hinge region. In one embodiment, the precursor polypeptide comprises a hinge region comprises a CPPC or SPPC amino acid sequence.

In one embodiment, the precursor polypeptide comprises a transmembrane region from CD8α, CD8β, 4-1BB/CD137, CD28, CD34, CD4, FcεRIγ, CD16, OX40/CD134, CD3ζ, CD3ε, CD3γ, CD3δ, TCRα, TCRβ, TCRζ, CD32, CD64, CD64, CD45, CD5, CD9, CD22, CD33, CD37, CD64, CD80, CD86, CD137, CD154, LFA-1 T cell co-receptor, CD2 T cell co-receptor/adhesion molecule, CD40, CD40L/CD154, VEGFR2, FAS, or FGFR2B.

In one embodiment, the precursor polypeptide comprises an intracellular signaling region comprises an intracellular signaling sequence in any order and of any combination of two to five signaling sequences from 4-1BB, CD3zeta, CD28, CD27, OX40, CD30, CD40, PD-1, ICOS, lymphocyte function-associated antigen-1 (LFA-1), CD2, CD7, LIGHT, NKG2C, B7-H3, GITR (TNFRSF18), DR3 (TNFRSF25), TNFR2 and/or CD226.

In one embodiment, the precursor polypeptide comprises the amino acid sequence of SEQ ID NO:15 or 18.

The present disclosure provides a dimeric antigen receptors (DAR) comprising: (a) a first polypeptide chain comprising five regions ordered from the amino terminus to the carboxyl terminus: (i) an antibody heavy chain variable region, (ii) an antibody heavy chain constant region, (iii) an optional hinge region, (iv) a transmembrane region, and (v) an intracellular signaling region comprising two or three intracellular signaling sequences; and (b) a second polypeptide chain comprising two regions ordered from the amino terminus to the carboxyl terminus: (i) an antibody light chain variable region, and (ii) an antibody light chain constant region, wherein the antibody heavy chain constant region and the antibody light chain constant region form a dimerization domain, and wherein the antibody heavy chain variable region and the antibody light chain variable region form an antigen binding domain.

The present disclosure provides a dimeric antigen receptors (DAR) comprising: (a) a first polypeptide chain comprising five regions ordered from the amino terminus to the carboxyl terminus: (i) an antibody light chain variable region, (ii) an antibody light chain constant region, (iii) an optional hinge region, (iv) a transmembrane region, and (v) an intracellular signaling region comprising two or three intracellular signaling sequences; and (b) a second polypeptide chain comprising two regions ordered from the amino terminus to the carboxyl terminus: (i) an antibody heavy chain variable region, and (ii) an antibody heavy chain constant region, wherein the antibody heavy chain constant region and the antibody light chain constant region form a dimerization domain, and wherein the antibody heavy chain variable region and the antibody light chain variable region form an antigen binding domain.

In one embodiment the dimeric antigen receptor (DAR) comprises an antibody heavy chain constant region and the antibody light chain constant region that dimerize via one or two disulfide bonds.

In one embodiment, the dimeric antigen receptor (DAR) optionally comprises a hinge region which can be derived from an antibody selected from a group consisting of IgG, IgA, IgM, IgE and IgD. In one embodiment, the hinge comprises a CD8a or CD28 hinge region. In one embodiment, the hinge region comprises a CPPC or SPPC amino acid sequence.

In one embodiment, the dimeric antigen receptor (DAR) comprises a transmembrane region from CD8α, CD8β, 4-1BB/CD137, CD28, CD34, CD4, FcεRIγ, CD16, OX40/CD134, CD3ζ, CD3ε, CD3γ, CD3δ, TCRα, TCRβ, TCRζ, CD32, CD64, CD64, CD45, CD5, CD9, CD22, CD33, CD37, CD64, CD80, CD86, CD137, CD154, LFA-1 T cell co-receptor, CD2 T cell co-receptor/adhesion molecule, CD40, CD40L/CD154, VEGFR2, FAS, and FGFR2B.

In one embodiment, the dimeric antigen receptor (DAR) comprises an intracellular signaling region comprising an intracellular signaling sequence in any order and of any combination of two to five signaling sequences from 4-1BB, CD3zeta, CD28, CD27, OX40, CD30, CD40, PD-1, ICOS, lymphocyte function-associated antigen-1 (LFA-1), CD2, CD7, LIGHT, NKG2C, B7-H3, GITR (TNFRSF18), DR3 (TNFRSF25), TNFR2 and/or CD226.

The present disclosure provides a dimeric antigen receptors (DAR) comprising: (a) a first polypeptide chain comprising five regions ordered from the amino terminus to the carboxyl terminus: (i) a CD38 antibody heavy chain variable region comprising the amino acid sequence of SEQ ID NO:1, (ii) a CD38 antibody heavy chain constant region comprising the amino acid sequence of SEQ ID NO:2, (iii) a CD28 hinge region comprising the amino acid sequence of SEQ ID NO:5 and optionally a second hinge region comprising the amino acid sequence of SEQ ID NO: 21, (iv) a CD28 transmembrane region comprising the amino acid sequence of SEQ ID NO: 6, and (v) an intracellular signaling region comprising a 4-1BB intracellular signaling sequence comprising the amino acid sequence of SEQ ID NO:7 and a CD3zeta intracellular signaling sequence comprising the amino acid sequence of SEQ ID NO:9 or 20; and (b) a second polypeptide chain comprising two regions ordered from the amino terminus to the carboxyl terminus: (i) a CD38 antibody light chain variable region comprising the amino acid sequence of SEQ ID NO:3, and (ii) a CD38 antibody light chain constant region comprising the amino acid sequence of SEQ ID NO:4, wherein the antibody heavy chain constant region and the antibody light chain constant region form a dimerization domain, and wherein the antibody heavy chain variable region and the antibody light chain variable region form an antigen binding domain that binds a CD38 protein. In one embodiment, the hinge region is optional.

In one embodiment, the dimeric antigen receptors (DAR) comprises a first polypeptide comprising the amino acid sequence of SEQ ID NO: 13 and a second polypeptide comprising the amino acid sequence of SEQ ID NO:14.

In one embodiment, the dimeric antigen receptors (DAR) comprises a first polypeptide comprising the amino acid sequence of SEQ ID NO: 16 and a second polypeptide comprising the amino acid sequence of SEQ ID NO:17.

The present disclosure provides a nucleic acid encoding a precursor polypeptide comprising (1) an antibody heavy chain leader sequence comprising the amino acid sequence of SEQ ID NO:10; (2) an antibody heavy chain variable region comprising the amino acid sequence of SEQ ID NO:1; (3) an antibody heavy chain constant region comprising the amino acid sequence of SEQ ID NO:2; (4) an optional hinger region comprising the amino acid sequence of SEQ ID NO:5; (5) a transmembrane region comprising the amino acid sequence of SEQ ID NO: 6; (6) an intracellular signaling region comprising any one or any combination of two or more signaling sequences selected from a group consisting of 4-1BB signaling sequence comprising the amino acid sequence of SEQ ID NO:7, CD28 signaling sequence comprising the amino acid sequence of SEQ ID NO:8, CD3zeta (long) signaling sequence comprising the amino acid sequence of SEQ ID NO:9 and/or CD3zeta (short) signaling sequence having an ITAM 3 motif and comprising the amino acid sequence of SEQ ID NO:20; (7) a T2A cleavage sequence comprising the amino acid sequence of SEQ ID NO: 12; (8) a light chain leader sequence comprising the amino acid sequence of SEQ ID NO:11; (9) an antibody light chain variable region comprising the amino acid sequence of SEQ ID NO:3; and (10) an antibody light chain constant region comprising the amino acid sequence of SEQ ID NO:4.

The present disclosure provides a nucleic acid encoding a precursor polypeptide comprising the amino acid sequence of SEQ ID NO:15 or 18.

The present disclosure provides a nucleic acid encoding (a) a first polypeptide chain comprising five regions ordered from the amino terminus to the carboxyl terminus: (i) a CD38 antibody heavy chain variable region comprising the amino acid sequence of SEQ ID NO:1, (ii) a CD38 antibody heavy chain constant region comprising the amino acid sequence of SEQ ID NO: 2, (iii) a CD28 hinge region comprising the amino acid sequence of SEQ ID NO:5 and optionally a second hinge region comprising the amino acid sequence of SEQ ID NO:21, (iv) a CD28 transmembrane region comprising the amino acid sequence of SEQ ID NO:6, and (v) an intracellular signaling region comprising a 4-1BB intracellular signaling sequence comprising the amino acid sequence of SEQ ID NO:7 and a CD3zeta intracellular signaling sequence comprising the amino acid sequence of SEQ ID NO:9 or 20; and the same nucleic acid or a second nucleic acid encoding (b) a second polypeptide chain comprising two regions ordered from the amino terminus to the carboxyl terminus: (i) a CD38 antibody light chain variable region comprising the amino acid sequence of SEQ ID NO:3, and (ii) a CD38 antibody light chain constant region comprising the amino acid sequence of SEQ ID NO:4, wherein the antibody heavy chain constant region and the antibody light chain constant region form a dimerization domain, and wherein the antibody heavy chain variable region and the antibody light chain variable region form an antigen binding domain that binds a CD38 protein. In one embodiment, the hinge region is optional.

In one embodiment, the nucleic acid encodes a first polypeptide comprising the amino acid sequence of SEQ ID NO:13 and a second polypeptide comprising the amino acid sequence of SEQ ID NO: 14.

In one embodiment, the nucleic acid encodes a first polypeptide comprising the amino acid sequence of SEQ ID NO:16 and a second polypeptide comprising the amino acid sequence of SEQ ID NO:17.

The present disclosure provides a vector operably linked to a nucleic acid encoding a precursor polypeptide comprising (1) an antibody heavy chain leader sequence comprising the amino acid sequence of SEQ ID NO:10; (2) an antibody heavy chain variable region comprising the amino acid sequence of SEQ ID NO:1; (3) an antibody heavy chain constant region comprising the amino acid sequence of SEQ ID NO:2; (4) an optional hinger region comprising the amino acid sequence of SEQ ID NO:5; (5) a transmembrane region comprising the amino acid sequence of SEQ ID NO:6; (6) an intracellular signaling region comprising any one or any combination of two or more signaling sequences selected from a group consisting of 4-1BB signaling sequence comprising the amino acid sequence of SEQ ID NO:7, CD28 signaling sequence comprising the amino acid sequence of SEQ ID NO:8, CD3zeta (long) signaling sequence comprising the amino acid sequence of SEQ ID NO:9 and/or CD3zeta (short) signaling sequence having an ITAM 3 motif and comprising the amino acid sequence of SEQ ID NO:20; (7) a T2A cleavage sequence comprising the amino acid sequence of SEQ ID NO: 12; (8) a light chain leader sequence comprising the amino acid sequence of SEQ ID NO:11; (9) an antibody light chain variable region comprising the amino acid sequence of SEQ ID NO:3; and (10) an antibody light chain constant region comprising the amino acid sequence of SEQ ID NO:4.

The present disclosure provides a vector operably linked to a nucleic acid encoding a precursor polypeptide having the amino acid sequence of SEQ ID NO: 15 or 18.

In one embodiment, the vector comprises an expression vector that is operably linked to a nucleic acid that encodes precursor polypeptide comprising the amino acid sequence of SEQ ID NO: 15 or 18.

In one embodiment, the expression vector in the host cell or the population of host cells directs transient introduction of the nucleic acid encoding the precursor polypeptide into the host cell or the population of host cells.

In one embodiment, the expression vector in the host cell or the population of host cells directs stable insertion into the host cell's genome the nucleic acid encoding the precursor polypeptide into the host cells' genome.

In one embodiment, the expression vector in the host cell or the population of host cells directs transcription and/or translation of the nucleic acid encoding the precursor polypeptide in the host cell or the population of host cells. For example, the expression vector can include one or more regulatory sequences, such as inducible and/or constitutive promoters and enhancers, which direct transcription and/or translation (e.g., expression) of the nucleic acid encoding the precursor polypeptide in the host cell or population of host cells.

The present disclosure provides a vector operably linked to a nucleic acid encoding (a) a first polypeptide chain comprising five regions ordered from the amino terminus to the carboxyl terminus: (i) a CD38 antibody heavy chain variable region comprising the amino acid sequence of SEQ ID NO:1, (ii) a CD38 antibody heavy chain constant region comprising the amino acid sequence of SEQ ID NO:2, (iii) a CD28 hinge region comprising the amino acid sequence of SEQ ID NO:5 and optionally a second hinge region comprising the amino acid sequence of SEQ ID NO:21, (iv) a CD28 transmembrane region comprising the amino acid sequence of SEQ ID NO:6, and (v) an intracellular signaling region comprising a 4-1BB intracellular signaling sequence comprising the amino acid sequence of SEQ ID NO:7 and a CD3zeta intracellular signaling sequence comprising the amino acid sequence of SEQ ID NO:9 or 20; and the same vector or a second vector operably linked to a nucleic acid encoding (b) a second polypeptide chain comprising two regions ordered from the amino terminus to the carboxyl terminus: (i) a CD38 antibody light chain variable region comprising the amino acid sequence of SEQ ID NO:3, and (ii) a CD38 antibody light chain constant region comprising the amino acid sequence of SEQ ID NO:4, wherein the antibody heavy chain constant region and the antibody light chain constant region form a dimerization domain, and wherein the antibody heavy chain variable region and the antibody light chain variable region form an antigen binding domain that binds a CD38 protein. In one embodiment, the vector comprises an expression vector. In one embodiment, the hinge region is optional.

In one embodiment, the expression vector is operably linked to a nucleic acid that encodes a first polypeptide comprising the amino acid sequence of SEQ ID NO: 13 and a second polypeptide comprising the amino acid sequence of SEQ ID NO:14.

In one embodiment, a first expression vector is operably linked to a nucleic acid that encodes a first polypeptide comprising the amino acid sequence of SEQ ID NO: 13 and a second vector operably linked to a nucleic acid that encodes a second polypeptide comprising the amino acid sequence of SEQ ID NO:14.

In one embodiment, the expression vector is operably linked to a nucleic acid that encodes a first polypeptide comprising the amino acid sequence of SEQ ID NO: 16 and a second polypeptide comprising the amino acid sequence of SEQ ID NO:17.

In one embodiment, a first expression vector is operably linked to a nucleic acid that encodes a first polypeptide comprising the amino acid sequence of SEQ ID NO: 16 and a second vector operably linked to a nucleic acid that encodes a second polypeptide comprising the amino acid sequence of SEQ ID NO:17.

In one embodiment, the expression vector in the host cell or the population of host cells directs transient introduction of the nucleic acid encoding the first and/or second polypeptide into the host cell or the population of host cells.

In one embodiment, the expression vector in the host cell or the population of host cells directs stable insertion into the host cell's genome the nucleic acid encoding the first and/or second polypeptide into the host cells' genome.

In one embodiment, the expression vector in the host cell or the population of host cells directs transcription and/or translation of the nucleic acid encoding the first and/or second polypeptide in the host cell or the population of host cells. For example, the expression vector can include one or more regulatory sequences, such as inducible and/or constitutive promoters and enhancers, which direct transcription and/or translation (e.g., expression) of the nucleic acid encoding the first and/or second polypeptide in the host cell or population of host cells.

The present disclosure provides a host cell or a population of host cells harboring a vector operably linked to a nucleic acid encoding a precursor polypeptide comprising (1) an antibody heavy chain leader sequence comprising the amino acid sequence of SEQ ID NO:10; (2) an antibody heavy chain variable region comprising the amino acid sequence of SEQ ID NO: 1; (3) an antibody heavy chain constant region comprising the amino acid sequence of SEQ ID NO: 2; (4) an optional hinger region comprising the amino acid sequence of SEQ ID NO:5; (5) a transmembrane region comprising the amino acid sequence of SEQ ID NO:6; (6) an intracellular signaling region comprising any one or any combination of two or more signaling sequences selected from a group consisting of 4-1BB signaling sequence comprising the amino acid sequence of SEQ ID NO:7, CD28 signaling sequence comprising the amino acid sequence of SEQ ID NO:8, CD3zeta (long) signaling sequence comprising the amino acid sequence of SEQ ID NO:9 and/or CD3zeta (short) signaling sequence having an ITAM 3 motif and comprising the amino acid sequence of SEQ ID NO:20; (7) a T2A cleavage sequence comprising the amino acid sequence of SEQ ID NO: 12; (8) a light chain leader sequence comprising the amino acid sequence of SEQ ID NO:11; (9) an antibody light chain variable region comprising the amino acid sequence of SEQ ID NO:3; and (10) an antibody light chain constant region comprising the amino acid sequence of SEQ ID NO:4.

In one embodiment, the host cell or population of host cells harbor a vector operably linked to a nucleic acid encoding a precursor polypeptide comprising the amino acid sequence of SEQ ID NO:15 or 18.

In one embodiment the vector harbored by the host cell or the population of host cells comprises an expression vector that directs transient introduction of the nucleic acid encoding the precursor polypeptide into the host cell or the population of host cells.

In one embodiment, the expression vector in the host cell or the population of host cells directs stable insertion into the host cell's genome the nucleic acid encoding the precursor polypeptide into the host cells' genome.

In one embodiment, the expression vector in the host cell or the population of host cells directs transcription and/or translation of the nucleic acid encoding the precursor polypeptide in the host cell or the population of host cells. For example, the expression vector can include one or more regulatory sequences, such as inducible and/or constitutive promoters and enhancers, which direct transcription and/or translation (e.g., expression) of the nucleic acid encoding the precursor polypeptide in the host cell or population of host cells.

The present disclosure provides a host cell or a population of host cells harboring a vector operably linked to a nucleic acid encoding (a) a first polypeptide chain comprising five regions ordered from the amino terminus to the carboxyl terminus: (i) a CD38 antibody heavy chain variable region comprising the amino acid sequence of SEQ ID NO:1, (ii) a CD38 antibody heavy chain constant region comprising the amino acid sequence of SEQ ID NO:2, (iii) a CD28 hinge region comprising the amino acid sequence of SEQ ID NO:5 and optionally a second hinge region comprising the amino acid sequence of SEQ ID NO:21, (iv) a CD28 transmembrane region comprising the amino acid sequence of SEQ ID NO:6, and (v) an intracellular signaling region comprising a 4-1BB intracellular signaling sequence comprising the amino acid sequence of SEQ ID NO:7 and a CD3zeta intracellular signaling sequence comprising the amino acid sequence of SEQ ID NO:9 or 20; and (b) a second polypeptide chain comprising two regions ordered from the amino terminus to the carboxyl terminus: (i) a CD38 antibody light chain variable region comprising the amino acid sequence of SEQ ID NO:3, and (ii) a CD38 antibody light chain constant region comprising the amino acid sequence of SEQ ID NO: 4, wherein the antibody heavy chain constant region and the antibody light chain constant region form a dimerization domain, and wherein the antibody heavy chain variable region and the antibody light chain variable region form an antigen binding domain that binds a CD38 protein. In one embodiment, the hinge region is optional. In one embodiment, the host cell or the population of host cells harbor an expression vector that directs transcription and/or translation (e.g., expression) of the first and/or second polypeptide chain. In one embodiment, the host cells expresses the first and/or second polypeptide chain.

In one embodiment, the host cell or population of host cells harbor a vector operably linked to a nucleic acid that encodes a first polypeptide comprising the amino acid sequence of SEQ ID NO:13 and a second polypeptide comprising the amino acid sequence of SEQ ID NO: 14.

In one embodiment, the host cell or population of host cells harbor a first vector operably linked to a nucleic acid that encodes a first polypeptide comprising the amino acid sequence of SEQ ID NO: 13 and a second vector operably linked to a nucleic acid that encodes a second polypeptide comprising the amino acid sequence of SEQ ID NO: 14.

In one embodiment, the host cell or population of host cells harbor the vector operably linked to a nucleic acid that encodes a first polypeptide comprising the amino acid sequence of SEQ ID NO:16 and a second polypeptide comprising the amino acid sequence of SEQ ID NO: 17.

In one embodiment, the host cell or population of host cells harbor a first vector operably linked to a nucleic acid that encodes a first polypeptide comprising the amino acid sequence of SEQ ID NO:16 and a second vector operably linked to a nucleic acid that encodes a second polypeptide comprising the amino acid sequence of SEQ ID NO: 17.

The present disclosure provides a method for treating a subject having a disease, disorder or condition associated with detrimental expression of a tumor antigen in the subject, comprising: administering to the subject a host cell, or a population of host cells, which harbors an expression vector operably linked to a nucleic acid that encodes a precursor polypeptide comprising: ten regions ordered from the amino terminus to the carboxyl terminus: (1) a heavy chain leader region, (2) an antibody heavy chain variable region, (3) an antibody heavy chain constant region, (4) an optional hinge region, (5) a transmembrane region, (6) an intracellular signaling region having two to five intracellular signaling sequences, (7) T2A cleavable sequence region, (8) a light chain leader region, (9) an antibody light chain variable region, and (10) an antibody light chain constant region.

In one embodiment, the host cell, or a population of host cells, harbors an expression vector operably linked to a nucleic acid that encodes a precursor polypeptide which comprises: (1) an antibody heavy chain leader sequence comprising the amino acid sequence of SEQ ID NO: 10; (2) an antibody heavy chain variable region comprising the amino acid sequence of SEQ ID NO: 1; (3) an antibody heavy chain constant region comprising the amino acid sequence of SEQ ID NO:2; (4) an optional hinger region comprising the amino acid sequence of SEQ ID NO: 5; (5) a transmembrane region comprising the amino acid sequence of SEQ ID NO:6; (6) an intracellular signaling region comprising any one or any combination of two or more signaling sequences selected from a group consisting of 4-1BB signaling sequence comprising the amino acid sequence of SEQ ID NO:7, CD28 signaling sequence comprising the amino acid sequence of SEQ ID NO:8, CD3zeta (long) signaling sequence comprising the amino acid sequence of SEQ ID NO:9 and/or CD3zeta (short) signaling sequence having an ITAM 3 motif and comprising the amino acid sequence of SEQ ID NO:20; (7) a T2A cleavage sequence comprising the amino acid sequence of SEQ ID NO: 12; (8) a light chain leader sequence comprising the amino acid sequence of SEQ ID NO:11; (9) an antibody light chain variable region comprising the amino acid sequence of SEQ ID NO:3; and (10) an antibody light chain constant region comprising the amino acid sequence of SEQ ID NO:4.

In one embodiment, the host cell, or the population of host cells, which harbors the expression vector operably linked to a nucleic acid that encodes a precursor polypeptide comprising the amino acid sequence of SEQ ID NO:15 or 18.

The present disclosure provides a method for treating a subject having a disease, disorder or condition associated with detrimental expression of a tumor antigen in the subject, comprising: administering to the subject a host cell, or a population of host cells, which harbors an expression vector operably linked to a nucleic acid that encodes (a) a first polypeptide chain comprising five regions ordered from the amino terminus to the carboxyl terminus: (i) a CD38 antibody heavy chain variable region comprising the amino acid sequence of SEQ ID NO:1, (ii) a CD38 antibody heavy chain constant region comprising the amino acid sequence of SEQ ID NO: 2, (iii) a CD28 hinge region comprising the amino acid sequence of SEQ ID NO:5 and optionally a second hinge region comprising the amino acid sequence of SEQ ID NO:21, (iv) a CD28 transmembrane region comprising the amino acid sequence of SEQ ID NO:6, and (v) an intracellular signaling region comprising a 4-1BB intracellular signaling sequence comprising the amino acid sequence of SEQ ID NO:7 and a CD3zeta intracellular signaling sequence comprising the amino acid sequence of SEQ ID NO:9 or 20; and (b) a second polypeptide chain comprising two regions ordered from the amino terminus to the carboxyl terminus: (i) a CD38 antibody light chain variable region comprising the amino acid sequence of SEQ ID NO:3, and (ii) a CD38 antibody light chain constant region comprising the amino acid sequence of SEQ ID NO: 4. In one embodiment, the antibody heavy chain constant region and the antibody light chain constant region form a dimerization domain, and wherein the antibody heavy chain variable region and the antibody light chain variable region form an antigen binding domain that binds a CD38 protein. In one embodiment, the hinge region is optional.

In one embodiment, the host cell or the population of host cells are selected from a group consisting of T lymphocytes (e.g., T cells, regulatory T cells, gamma-delta T cells, and cytotoxic T cells), NK (natural killer) cells, macrophages, dendritic cells, mast cells, eosinophils, B lymphocytes and monocytes.

In one embodiment, the host cells comprise NK cells that comprise cord blood-derived NK cells, or placental derived NK cells.

In one embodiment, the expression vector in the host cell or the population of host cells directs transient introduction of the nucleic acid encoding the first and/or second polypeptide into the host cell or the population of host cells.

In one embodiment, the expression vector in the host cell or the population of host cells directs stable insertion into the host cell's genome the nucleic acid encoding the first and/or second polypeptide into the host cells' genome.

In one embodiment, the expression vector in the host cell or the population of host cells directs transcription and/or translation of the nucleic acid encoding the first and/or second polypeptide in the host cell or the population of host cells. For example, the expression vector can include one or more regulatory sequences, such as inducible and/or constitutive promoters and enhancers, which direct transcription and/or translation (e.g., expression) of the nucleic acid encoding the first and/or second polypeptide in the host cell or population of host cells.

In one embodiment, the disease, disorder or condition associated with detrimental expression of a tumor antigen, is a cancer, including, but not limited to hematologic breast cancer, ovarian cancer, prostate cancer, head and neck cancer, lung cancer, bladder cancer, melanoma, colorectal cancer, pancreatic cancer, lung cancer, liver cancer, renal cancer, esophageal cancer, leiomyoma, leiomyosarcoma, glioma, and glioblastoma.

In one embodiment, the disease is a hematologic cancer selected from the group consisting of non-Hodgkin's lymphoma (NHL), Burkitt's lymphoma (BL), B chronic lymphocytic leukemia (B-CLL), B and T acute lymphocytic leukemia (ALL), T cell lymphoma (TCL), acute myeloid leukemia (AML), hairy cell leukemia (HCL), Hodgkin's Lymphoma (HL), chronic myeloid leukemia (CML) and multiple myeloma (MM).

DESCRIPTION OF THE DRAWINGS

FIG. 35A shows amino acid sequences of different regions of CD38 dimeric antigen receptor (DAR) construct.

FIG. 35B shows amino acid sequences of a first polypeptide, a second polypeptide and precursor polypeptide of a CD38 dimeric antigen receptor (DAR) construct V2a.

FIG. 35C shows amino acid sequences of a first polypeptide, a second polypeptide and precursor polypeptide of a CD38 dimeric antigen receptor (DAR) construct V3.

FIG. 35D shows amino acid sequences of a long hinge sequence comprising CD8 and CD28 hinge sequences, and a CD3zeta signaling region having only ITAM 3 motif, a CD8 hinge sequence, and an anti-CD38 CAR construct.

DESCRIPTION

Figure 1:
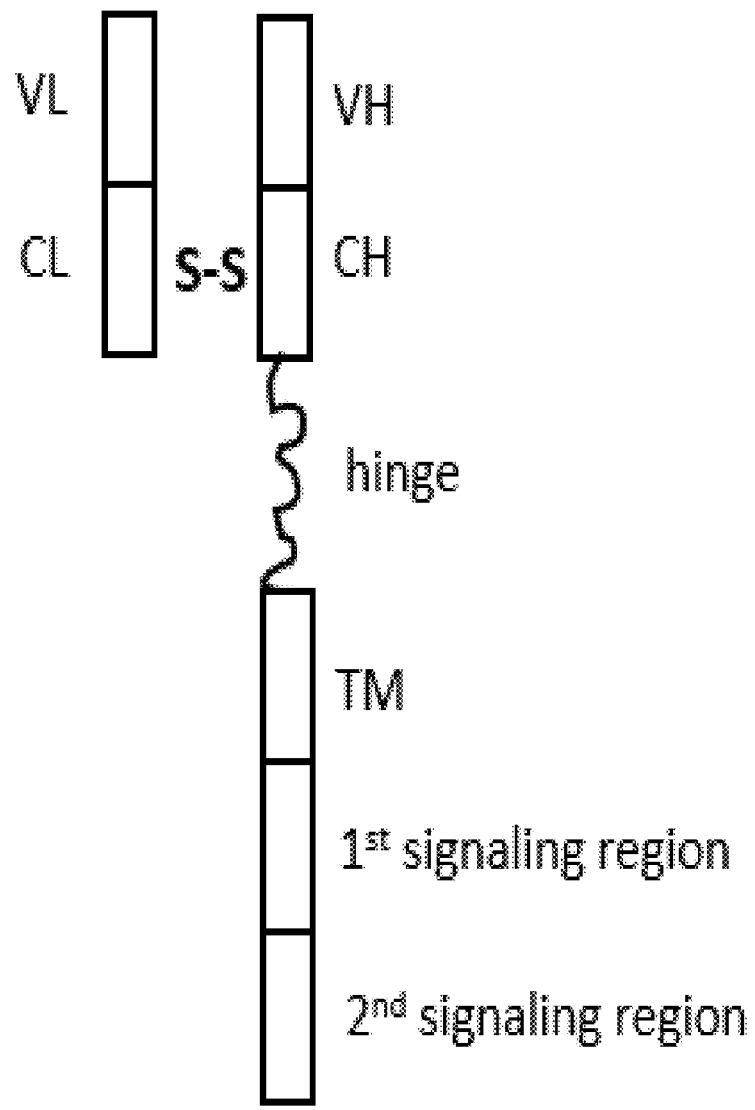
FIG. 1 is a schematic showing an exemplary dimeric antigen receptor comprising two intracellular signaling sequences.

Unless defined otherwise, technical and scientific terms used herein have meanings that are commonly understood by those of ordinary skill in the art unless defined otherwise. Generally, terminologies pertaining to techniques of cell and tissue culture, molecular biology, immunology, microbiology, genetics, transgenic cell production, protein chemistry and nucleic acid chemistry and hybridization described herein are well known and commonly used in the art. The methods and techniques provided herein are generally performed according to conventional procedures well known in the art and as described in various general and more specific references that are cited and discussed herein unless otherwise indicated. See, e.g., Sambrook et al. Molecular Cloning: A Laboratory Manual, 2d ed., Cold Spring Harbor Laboratory Press, Cold Spring Harbor, N.Y. (1989) and Ausubel et al., Current Protocols in Molecular Biology, Greene Publishing Associates (1992). A number of basic texts describe standard antibody production processes, including, Borrebaeck (cd) *Antibody Engineering, 2nd Edition* Freeman and Company, N Y, 1995; McCafferty et al. *Antibody Engineering, A Practical Approach* IRL at Oxford Press, Oxford, England, 1996; and Paul (1995) *Antibody Engineering Protocols* Humana Press, Towata, N.J., 1995; Paul (ed.), *Fundamental Immunology*, Raven Press, N.Y, 1993; Coligan (1991) *Current Protocols in Immunology* Wiley/Greene, NY; Harlow and Lane (1989) *Antibodies: A Laboratory Manual* Cold Spring Harbor Press, NY; Stites et al. (eds.) *Basic and Clinical Immunology* (4th ed.) Lange Medical Publications, Los Altos, Calif., and references cited therein; *Coding Monoclonal Antibodies: Principles and Practice* (2nd ed.) Academic Press, New York, N. Y., 1986, and Kohler and Milstein *Nature* 256:495-497, 1975. All of the references cited herein are incorporated herein by reference in their entireties. Enzymatic reactions and enrichment/purification techniques are also well known and are performed according to manufacturer's specifications, as commonly accomplished in the art or as described herein. The terminology used in connection with, and the laboratory procedures and techniques of, analytical chemistry, synthetic organic chemistry, and medicinal and pharmaceutical chemistry described herein are well known and commonly used in the art. Standard techniques can be used for chemical syntheses, chemical analyses, pharmaceutical preparation, formulation, and delivery, and treatment of patients.

The headings provided herein are not limitations of the various aspects of the disclosure, which aspects can be understood by reference to the specification as a whole.

Unless otherwise required by context herein, singular terms shall include pluralities and plural terms shall include the singular. Singular forms "a", "an" and "the", and singular use of any word, include plural referents unless expressly and unequivocally limited on one referent.

It is understood the use of the alternative (e.g., "or") herein is taken to mean either one or both or any combination thereof of the alternatives.

The term "and/or" used herein is to be taken mean specific disclosure of each of the specified features or components with or without the other. For example, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

As used herein, terms "comprising", "including", "having" and "containing", and their grammatical variants, as used herein are intended to be non-limiting so that one item or multiple items in a list do not exclude other items that can be substituted or added to the listed items. It is understood that wherever aspects are described herein with the language "comprising," otherwise analogous aspects described in terms of "consisting of" and/or "consisting essentially of" are also provided.

As used herein, the term "about" refers to a value or composition that is within an acceptable error range for the particular value or composition as determined by one of ordinary skill in the art, which will depend in part on how the value or composition is measured or determined, i.e., the limitations of the measurement system. For example, "about" or "approximately" can mean within one or more than one standard deviation per the practice in the art. Alternatively, "about" or "approximately" can mean a range of up to 10% (i.e., ±10%) or more depending on the limitations of the measurement system. For example, about 5 mg can include any number between 4.5 mg and 5.5 mg. Furthermore, particularly with respect to biological systems or processes, the terms can mean up to an order of magnitude or up to 5-fold of a value. When particular values or compositions are provided in the instant disclosure, unless otherwise stated, the meaning of "about" or "approximately" should be assumed to be within an acceptable error range for that particular value or composition.

The terms "peptide", "polypeptide" and "protein" and other related terms used herein are used interchangeably and refer to a polymer of amino acids and are not limited to any particular length. Polypeptides may comprise natural and non-natural amino acids. Polypeptides include recombinant or chemically-synthesized forms. Polypeptides also include precursor molecules that have not yet been subjected to post-translation modification such as proteolytic cleavage, cleavage due dot T2A ribosomal skipping, hydroxylation, methylation, lipidation, acetylation, SUMOylation, ubiquitination, glycosylation, phosphorylation and/or disulfide bond formation. These terms encompass native and artificial proteins, protein fragments and polypeptide analogs (such as muteins, variants, chimeric proteins and fusion proteins) of a protein sequence as well as post-translationally, or otherwise covalently or non-covalently, modified proteins. Dimeric antigen receptors comprising two polypeptide chains are described herein.

The terms "nucleic acid", "polynucleotide" and "oligonucleotide" and other related terms used herein are used interchangeably and refer to polymers of nucleotides and are not limited to any particular length. Nucleic acids include recombinant and chemically-synthesized forms. Nucleic acids include DNA molecules (cDNA or genomic DNA), RNA molecules (e.g., mRNA), analogs of the DNA or RNA generated using nucleotide analogs (e.g., peptide nucleic acids and non-naturally occurring nucleotide analogs), and hybrids thereof. Nucleic acid molecule can be single-stranded or double-stranded. In one embodiment, the nucleic acid molecules of the disclosure comprise a contiguous open reading frame encoding an antibody, or a fragment or scFv, derivative, mutein, or variant thereof. In one embodiment, nucleic acids comprise a one type of polynucleotides or a mixture of two or more different types of polynucleotides. Nucleic acids encoding the dimeric antigen receptors are described herein.

An antigen binding protein can have, for example, the structure of an immunoglobulin. In one embodiment, an "immunoglobulin" refers to a tetrameric molecule composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa or lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two antigen binding sites. In one embodiment, an antigen binding protein can be a synthetic molecule having a structure that differs from a tetrameric immunoglobulin molecule but still binds a target antigen or binds two or more target antigens. For example, a synthetic antigen binding protein can comprise antibody fragments, 1-6 or more polypeptide chains, asymmetrical assemblies of polypeptides, or other synthetic molecules. Dimeric antigen receptors having immunoglobulin-like properties that bind specifically to target antigens are described herein.

An "antibody" and "antibodies" and related terms used herein refers to an intact immunoglobulin or to an antigen binding portion thereof that binds specifically to an antigen. Antigen binding portions may be produced by recombinant DNA techniques or by enzymatic or chemical cleavage of intact antibodies. Antigen binding portions include, inter alia, Fab, Fab', F(ab')$_2$, Fv, domain antibodies (dAbs), and complementarity determining region (CDR) fragments, single-chain antibodies (scFv), chimeric antibodies, diabodies, triabodies, tetrabodies, and polypeptides that contain at least a portion of an immunoglobulin that is sufficient to confer specific antigen binding to the polypeptide.

Antibodies include recombinantly produced antibodies and antigen binding portions. Antibodies include non-human, chimeric, humanized and fully human antibodies. Antibodies include monospecific, multispecific (e.g., bispecific, trispecific and higher order specificities). Antibodies include tetrameric antibodies, light chain monomers, heavy chain monomers, light chain dimers, heavy chain dimers. Antibodies include F(ab')$_2$ fragments, Fab' fragments and Fab fragments. Antibodies include single domain antibodies, monovalent antibodies, single chain antibodies, single chain variable fragment (scFv), camelized antibodies, affibodies, disulfide-linked Fvs (sdFv), anti-idiotypic antibodies (anti-Id), minibodies. Antibodies include monoclonal and polyclonal populations. Dimeric antigen receptors that behave like antibodies are described herein.

An "antigen binding domain," "antigen binding region," or "antigen binding site" and other related terms used herein refer to a portion of an antigen binding protein that contains amino acid residues (or other moieties) that interact with an antigen and contribute to the antigen binding protein's specificity and affinity for the antigen. For an antibody that specifically binds to its antigen, this will include at least part of at least one of its CDR domains. Dimeric antigen receptors having antibody heavy chain variable region and the antibody light chain variable region that form an antigen binding domain are described herein.

The terms "specific binding", "specifically binds" or "specifically binding" and other related terms, as used herein in the context of an antibody or antigen binding protein or antibody fragment, refer to non-covalent or covalent preferential binding to an antigen relative to other molecules or moieties (e.g., an antibody specifically binds to a particular antigen relative to other available antigens). In one embodiment, an antibody specifically binds to a target antigen if it binds to the antigen with a dissociation constant $K_D$ of $10^{-5}$ M or less, or $10^{-6}$ M or less, or $10^{-7}$ M or less, or $10^{-8}$ M or less, or $10^{-9}$ M or less, or $10^{-10}$ M or less. Dimeric antigen receptors that specifically bind target antigens are described herein.

In one embodiment, a dissociation constant ($K_D$) can be measured using a BIACORE surface plasmon resonance (SPR) assay. Surface plasmon resonance refers to an optical phenomenon that allows for the analysis of real-time interactions by detection of alterations in protein concentrations within a biosensor matrix, for example using the BIACORE system (Biacore Life Sciences division of GE Healthcare, Piscataway, NJ).

An "epitope" and related terms as used herein refers to a portion of an antigen that is bound by an antigen binding protein (e.g., by an antibody or an antigen binding portion thereof). An epitope can comprise portions of two or more antigens that are bound by an antigen binding protein. An epitope can comprise non-contiguous portions of an antigen or of two or more antigens (e.g., amino acid residues that are not contiguous in an antigen's primary sequence but that, in the context of the antigen's tertiary and quaternary structure, are near enough to each other to be bound by an antigen binding protein). Generally, the variable regions, particularly the CDRs, of an antibody interact with the epitope. Dimeric antigen receptors that bind an epitope of a target antigen (e.g., CD38) are described herein.

An "antibody fragment", "antibody portion", "antigen-binding fragment of an antibody", or "antigen-binding portion of an antibody" and other related terms used herein refer to a molecule other than an intact antibody that comprises a portion of an intact antibody that binds the antigen to which the intact antibody binds. Examples of antibody fragments include, but are not limited to, Fv, Fab, Fab', Fab'-SH, F(ab')$_2$; Fd; and Fv fragments, as well as dAb; diabodies; linear antibodies; single-chain antibody molecules (e.g. scFv); polypeptides that contain at least a portion of an antibody that is sufficient to confer specific antigen binding to the polypeptide. Antigen binding portions of an antibody may be produced by recombinant DNA techniques or by enzymatic or chemical cleavage of intact antibodies. Antigen binding portions include, inter alia, Fab, Fab', F(ab')$_2$, Fv, domain antibodies (dAbs), and complementarity determining region (CDR) fragments, chimeric antibodies, diabodies, triabodies, tetrabodies, and polypeptides that contain at least a portion of an immunoglobulin that is sufficient to confer antigen binding properties to the antibody fragment. Dimeric antigen receptors comprising a Fab fragment joined to a hinge, transmembrane and intracellular signaling regions are described herein.

The terms "Fab", "Fab fragment" and other related terms refers to a monovalent fragment comprising a variable light chain region ($V_L$), constant light chain region ($C_L$), variable heavy chain region ($V_H$), and first constant region ($C_{H1}$). A Fab is capable of binding an antigen. An F(ab')$_2$ fragment is a bivalent fragment comprising two Fab fragments linked by a disulfide bridge at the hinge region. A F (Ab') 2 has antigen binding capability. An Fd fragment comprises $V_H$ and $C_{H1}$ regions. An Fv fragment comprises $V_L$ and $V_H$ regions. An Fv can bind an antigen. A dAb fragment has a $V_H$ domain, a $V_L$ domain, or an antigen-binding fragment of a $V_H$ or VL domain (U.S. Pat. Nos. 6,846,634 and 6,696,245; U.S. published Application Nos. 2002/02512, 2004/0202995, 2004/0038291, 2004/0009507, 2003/0039958; and Ward et al., Nature 341:544-546, 1989). Dimeric antigen receptors comprising a Fab fragment joined to a hinge, transmembrane and intracellular signaling regions are described herein.

The term "human antibody" refers to antibodies that have one or more variable and constant regions derived from human immunoglobulin sequences. In one embodiment, all of the variable and constant domains are derived from human immunoglobulin sequences (e.g., a fully human antibody). These antibodies may be prepared in a variety of ways, examples of which are described below, including through recombinant methodologies or through immunization with an antigen of interest of a mouse that is genetically modified to express antibodies derived from human heavy and/or light chain-encoding genes. Dimeric antigen receptors comprising fully human antibody heavy chain variable region and the antibody light chain variable region are described herein.

The term "hinge" refers to an amino acid segment that is generally found between two domains of a protein and may allow for flexibility of the overall construct and movement of one or both of the domains relative to one another. Structurally, a hinge region comprises from about 10 to about 100 amino acids, e.g., from about 15 to about 75 amino acids, from about 20 to about 50 amino acids, or from about 30 to about 60 amino acids. In one embodiment, the hinge region is 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, or 100 amino acids in length. The hinge region can be derived from is a hinge region of a naturally-occurring protein, such as a CD8 hinge region or a fragment thereof, a CD8a hinge region, or a fragment thereof, a hinge region of an antibody (e.g., IgG, IgA, IgM, IgE, or IgD antibodies), or a hinge region that joins the constant domains CH1 and CH2 of an antibody. The hinge region can be derived from an antibody and may or may not comprise one or more constant regions of the antibody, or the hinge region comprises the hinge region of an antibody and the CH3 constant region of the antibody, or the hinge region comprises the hinge region of an antibody and the CH2 and CH3 constant regions of the antibody, or the hinge region is a non-naturally occurring peptide, or the hinge region is disposed between the C-terminus of the scFv and the N-terminus of the transmembrane domain.

The term "leader sequence" or "leader peptide" or "peptide signal sequence" or "signal peptide" refers to a peptide sequence that is located at the N-terminus of a polypeptide. A leader sequence directs a polypeptide chain to a cellular secretory pathway and can direct integration and anchoring of the polypeptide into the lipid bilayer of the cellular membrane. Typically, a leader sequence is about $10^{-50}$ amino acids in length. A leader sequence can direct transport of a precursor polypeptide from the cytosol to the endoplasmic reticulum. A leader sequence include signal sequences comprising CD8α, CD28 or CD16 leader sequences.

The term "Chimeric Antigen Receptor" or "CAR" refers to a single chain fusion protein comprising an extracellular antigen-binding protein that is fused to an intracellular signaling domain. The CAR extracellular binding domain is a single chain variable fragment (scFv or sFv) derived from fusing the variable heavy and light regions of a monoclonal antibody, such as a human monoclonal antibody. The disclosed constructs are DARs which are distinct from CARs in that DARs do not use a single chain antibody for targeting but instead use separate heavy and light chain variable domain regions.

A "vector" and related terms used herein refers to a nucleic acid molecule (e.g., DNA or RNA) which can be operably linked to foreign genetic material (e.g., nucleic acid transgene). Vectors can be used as a vehicle to introduce foreign genetic material into a cell (e.g., host cell). Vectors can include at least one restriction endonuclease recognition sequence for insertion of the transgene into the vector. Vectors can include at least one gene sequence that confers antibiotic resistance or a selectable characteristic to aid in selection of host cells that harbor a vector-transgene construct. Vectors can be single-stranded or double-stranded nucleic acid molecules. Vectors can be linear or circular nucleic acid molecules. A donor nucleic acid used for gene editing methods employing zinc finger nuclease, TALEN or CRISPR/Cas can be a type of a vector. One type of vector is a "plasmid," which refers to a linear or circular double stranded extrachromosomal DNA molecule which can be linked to a transgene, and is capable of replicating in a host cell, and transcribing and/or translating the transgene. A viral vector typically contains viral RNA or DNA backbone sequences which can be linked to the transgene. The viral backbone sequences can be modified to disable infection but retain insertion of the viral backbone and the co-linked transgene into a host cell genome. Examples of viral vectors include retroviral, lentiviral, adenoviral, adeno-associated, baculoviral, papovaviral, vaccinia viral, herpes simplex viral and Epstein Barr viral vectors. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome.

An "expression vector" is a type of vector that can contain one or more regulatory sequences, such as inducible and/or constitutive promoters and enhancers. Expression vectors can include ribosomal binding sites and/or polyadenylation sites. Regulatory sequences direct transcription, or transcription and translation, of a transgene linked to the expression vector which is transduced into a host cell. The regulatory sequence(s) can control the level, timing and/or location of expression of the transgene. The regulatory sequence can, for example, exert its effects directly on the transgene, or through the action of one or more other molecules (e.g., polypeptides that bind to the regulatory sequence and/or the nucleic acid). Regulatory sequences can be part of a vector. Further examples of regulatory sequences are described in, for example, Goeddel, 1990, Gene Expression Technology: Methods in Enzymology 185, Academic Press, San Diego, Calif. and Baron et al., 1995, Nucleic Acids Res. 23:3605-3606. Expression vectors comprising nucleic acids that encode dimeric antigen receptors are described herein.

A transgene is "operably linked" to a vector when there is linkage between the transgene and the vector to permit functioning or expression of the transgene sequences contained in the vector. In one embodiment, a transgene is "operably linked" to a regulatory sequence when the regulatory sequence affects the expression (e.g., the level, timing, or location of expression) of the transgene.

The terms "transfected" or "transformed" or "transduced" or other related terms used herein refer to a process by which exogenous nucleic acid (e.g., transgene) is transferred or introduced into a host cell. A "transfected" or "transformed" or "transduced" host cell is one which has been transfected, transformed or transduced with exogenous nucleic acid (transgene). The host cell includes the primary subject cell and its progeny. Exogenous nucleic acids encoding at least a portion of any of the dimeric antigen receptors are described herein and can be introduced into a host cell. Expression vectors comprising at least a portion of any of the dimeric antigen receptors described herein can be introduced into a host cell, and the host cell can express the first and second polypeptides that dimerize to form the dimeric antigen receptors described herein.

The terms "host cell" or "or a population of host cells" or related terms as used herein refer to a cell (or a population thereof) into which foreign (exogenous or transgene) nucleic acids have been introduced. The foreign nucleic acids can include an expression vector operably linked to a transgene, and the host cell can be used to express the nucleic acid and/or polypeptide encoded by the foreign nucleic acid (transgene). A host cell (or a population thereof) can be a cultured cell or can be extracted from a subject. The host cell (or a population thereof) includes the primary subject cell and its progeny without any regard for the number of passages. The host cell (or a population thereof) includes immortalized cell lines. Progeny cells may or may not harbor identical genetic material compared to the parent cell. Host cells encompass progeny cells. In one embodiment, a host cell describes any cell (including its progeny) that has been modified, transfected, transduced, transformed, and/or manipulated in any way to express an antibody, as disclosed herein. In one example, the host cell (or population thereof) can be introduced with an expression vector operably linked to a nucleic acid encoding the desired antibody, or an antigen binding portion thereof, described herein. Host cells and populations thereof can harbor an expression vector that is stably integrated into the host's genome or can harbor an extrachromosomal expression vector. In one embodiment, host cells and populations thereof can harbor an extrachromosomal vector that is present after several cell divisions or is present transiently and is lost after several cell divisions.

A host cell can be a prokaryote, for example, E. coli, or it can be a eukaryote, for example, a single-celled eukaryote (e.g., a yeast or other fungus), a plant cell (e.g., a tobacco or tomato plant cell), an mammalian cell (e.g., a human cell, a monkey cell, a hamster cell, a rat cell, a mouse cell, or an insect cell) or a hybridoma. In one embodiment, a host cell can be introduced with an expression vector operably linked to a nucleic acid encoding a desired antibody thereby generating a transfected/transformed host cell which is cultured under conditions suitable for expression of the antibody by the transfected/transformed host cell, and optionally recovering the antibody from the transfected/transformed host cells (e.g., recovery from host cell lysate) or recovery from the culture medium. In one embodiment, host cells comprise non-human cells including CHO, BHK, NS0, SP2/0, and YB2/0. In one embodiment, host cells comprise human cells including HEK293, HT-1080, Huh-7 and PER.C6. Examples of host cells include the COS-7 line of monkey kidney cells (ATCC CRL 1651) (see Gluzman et al., 1981, Cell 23:175), L cells, C127 cells, 3T3 cells (ATCC CCL 163), Chinese hamster ovary (CHO) cells or their derivatives such as Veggie CHO and related cell lines which grow in serum-free media (see Rasmussen et al., 1998, Cytotechnology 28:31) or CHO strain DX-B 11, which is deficient in DHFR (see Urlaub et al., 1980, Proc. Natl. Acad. Sci. USA 77:4216-20), HeLa cells, BHK (ATCC CRL 10) cell lines, the CV1/EBNA cell line derived from the African green monkey kidney cell line CV1 (ATCC CCL 70) (see McMahan et al., 1991, EMBO J. 10:2821), human embryonic kidney cells such as 293, 293 EBNA or MSR 293, human epidermal A431 cells, human Colo 205 cells, other transformed primate cell lines, normal diploid cells, cell strains derived from in vitro culture of primary tissue, primary explants, HL-60, U937, HaK or Jurkat cells. In one embodiment, host cells include lymphoid cells such as Y0, NS0 or Sp20. In one embodiment, a host cell is a mammalian host cell, but is not a human host cell. Typically, a host cell is a cultured cell that can be transformed or transfected with a polypeptide-encoding nucleic acid, which can then be expressed in the host cell. The phrase "transgenic host cell" or "recombinant host cell" can be used to denote a host cell that has been introduced (e.g., transformed or transfected) with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but also to the progeny or potential progeny of such a cell. Because certain modifications may occur in succeeding generations due to, e.g., mutation or environmental influence, such progeny may not, in fact, be identical to the parent cell, but are still included within the scope of the term as used herein.

The host cell or the population of host cells comprise T lymphocytes (e.g., T cells, regulatory T cells, gamma-delta T cells, and cytotoxic T cells), NK (natural killer) cells, macrophages, dendritic cells, mast cells, eosinophils, B lymphocytes, monocytes. In one embodiment, the NK cells comprise cord blood-derived NK cells, or placental derived NK cells.

Transgenic host cells can be prepared using non-viral methods, including well-known designer nucleases including zinc finger nucleases, TALENS or CRISPR/Cas. A transgene can be introduced into a host cell's genome using genome editing technologies such as zinc finger nuclease. A zinc finger nuclease includes a pair of chimeric proteins each containing a non-specific endonuclease domain of a restriction endonuclease (e.g., FokI) fused to a DNA-binding domain from an engineered zinc finger motif. The DNA-binding domain can be engineered to bind a specific sequence in the host's genome and the endonuclease domain makes a double-stranded cut. The donor DNA carries the transgene, for example any of the nucleic acids encoding a CAR or DAR construct described herein, and flanking sequences that are homologous to the regions on either side of the intended insertion site in the host cell's genome. The host cell's DNA repair machinery enables precise insertion of the transgene by homologous DNA repair. Transgenic mammalian host cells have been prepared using zinc finger nucleases (U.S. Pat. Nos. 9,597,357, 9,616,090, 9,816,074 and 8,945,868). A transgenic host cell can be prepared using TALEN (Transcription Activator-Like Effector Nucleases) which are similar to zinc finger nucleases in that they include a non-specific endonuclease domain fused to a DNA-binding domain which can deliver precise transgene insertion. Like zinc finger nucleases, TALEN also introduce a double-strand cut into the host's DNA. Transgenic host cells can be prepared using CRISPR (Clustered Regularly Interspaced Short Palindromic Repeats). CRISPR employs a Cas endonuclease coupled to a guide RNA for target specific donor DNA integration. The guide RNA includes a conserved multi-nucleotide containing protospacer adjacent motif (PAM) sequence upstream of the gRNA-binding region in the target DNA and hybridizes to the host cell target site where the Cas endonuclease cleaves the double-stranded target DNA. The guide RNA can be designed to hybridize to a specific target site. Similar to zinc finger nuclease and TALEN, the CRISPR/Cas system can be used to introduce site specific insertion of donor DNA having flanking sequences that have homology to the insertion site. Examples of CRISPR/Cas systems used to modify genomes are described for example in U.S. Pat. Nos. 8,697,359, 10,000,772, 9,790,490, and U. S. Patent Application Publication No. US 2018/0346927. In one embodiment, transgenic host cells can be prepared using zinc finger nuclease, TALEN or CRISPR/Cas system, and the host target site can be a TRAC gene (T Cell Receptor Alpha Constant). The donor DNA can include for example any of the nucleic acids encoding a CAR or DAR construct described herein. Electroporation, nucleofection or lipofection can be used to co-deliver into the host cell the donor DNA with the zinc finger nuclease, TALEN or CRISPR/Cas system.

Transgenic host cells can be prepared by transducing T cells with a retroviral vector carrying the CAR or DAR construct. The transduction can be performed essentially as described in Ma et al., 2004 *The Prostate* 61:12-25; and Ma et al., *The Prostate* 74 (3): 286-296, 2014 (the disclosures of which are incorporated by reference herein in their entireties). The anti-CD38 CAR or DAR MFG retroviral vector plasmid DNA can be transfected into a Phoenix-Eco cell line (ATCC) using FuGene reagent (Promega, Madison, WI) to produce Ecotropic retrovirus, then harvest transient viral supernatant (Ecotropic virus) can be used to transduce PG13 packaging cells with Gal-V envelope to produce retrovirus to infect human cells. Viral supernatant from the PG13 cells can be used to transduce activated T cells (or PBMCs) two to three days after CD3 or CD3/CD28 activation. Activated human T cells can be prepared by activating normal healthy donor peripheral blood mononuclear cells (PBMC) with 100 ng/ml mouse anti-human CD3 antibody OKT3 (Orth Biotech, Rartian, NJ) or anti-CD3, anti-CD28 TransAct (Miltenyi Biotech, German) as manufacturer's manual and 300-1000 U/ml IL2 in AIM-V growth medium (GIBCO-Thermo Fisher scientific, Waltham, MA) supplemented with 5% FBS for two days. Approximately $5 \times 10^6$ activated human T cells can be transduced in a 10 µg/ml retronectin (Takara Bio USA) pre-coated 6-well plate with 3 ml viral supernatant and centrifuged at 1000 g for about 1 hour at approximately 32° C. After transduction, the transduced T cells can be expanded in AIM-V growth medium supplemented with 5% FBS and 300-1000 U/ml IL2.

Polypeptides of the present disclosure (e.g., antibodies and antigen binding proteins) can be produced using any methods known in the art. In one example, the polypeptides are produced by recombinant nucleic acid methods by inserting a nucleic acid sequence (e.g., DNA) encoding the polypeptide into a recombinant expression vector which is introduced into a host cell and expressed by the host cell under conditions promoting expression.

General techniques for recombinant nucleic acid manipulations are described for example in Sambrook et al., in *Molecular Cloning: A Laboratory Manual*, Vols. 1-3, Cold Spring Harbor Laboratory Press, 2 ed., 1989, or F. Ausubel et al., in Current Protocols in Molecular Biology (Green Publishing and Wiley-Interscience: New York, 1987) and periodic updates, herein incorporated by reference in their entireties. The nucleic acid (e.g., DNA) encoding the polypeptide is operably linked to an expression vector carrying one or more suitable transcriptional or translational regulatory elements derived from mammalian, viral, or insect genes. Such regulatory elements include a transcriptional promoter, an optional operator sequence to control transcription, a sequence encoding suitable mRNA ribosomal binding sites, and sequences that control the termination of transcription and translation. The expression vector can include an origin or replication that confers replication capabilities in the host cell. The expression vector can include a gene that confers selection to facilitate recognition of transgenic host cells (e.g., transformants).

The recombinant DNA can also encode any type of protein tag sequence that may be useful for purifying the protein. Examples of protein tags include but are not limited to a histidine tag, a FLAG tag, a myc tag, an HA tag, or a GST tag. Appropriate cloning and expression vectors for use with bacterial, fungal, yeast, and mammalian cellular hosts can be found in Cloning Vectors: A Laboratory Manual, (Elsevier, N.Y., 1985).

The expression vector construct can be introduced into the host cell using a method appropriate for the host cell. A variety of methods for introducing nucleic acids into host cells are known in the art, including, but not limited to, electroporation; transfection employing calcium chloride, rubidium chloride, calcium phosphate, DEAE-dextran, or other substances; viral transfection; non-viral transfection; microprojectile bombardment; lipofection; and infection (e.g., where the vector is an infectious agent). Suitable host cells include prokaryotes, yeast, mammalian cells, or bacterial cells.

Suitable bacteria include gram negative or gram positive organisms, for example, *E. coli* or *Bacillus* spp. Yeast, such as from the *Saccharomyces* species, such as *S. cerevisiae*, may also be used for production of polypeptides. Various mammalian or insect cell culture systems can also be employed to express recombinant proteins. Baculovirus systems for production of heterologous proteins in insect cells are reviewed by Luckow and Summers, (Bio/Technology, 6:47, 1988). Examples of suitable mammalian host cell lines include endothelial cells, COS-7 monkey kidney cells, CV-1, L cells, C127, 3T3, Chinese hamster ovary (CHO), human embryonic kidney cells, HeLa, 293, 293T, and BHK cell lines. Purified polypeptides are prepared by culturing suitable host/vector systems to express the recombinant proteins. The protein is then purified from culture media or cell extracts. Any of the first and second polypeptides that form a dimeric antigen receptor can be expressed by transgenic host cells.

Antibodies and antigen binding proteins disclosed herein can also be produced using cell-translation systems. For such purposes the nucleic acids encoding the polypeptide must be modified to allow in vitro transcription to produce mRNA and to allow cell-free translation of the mRNA in the particular cell-free system being utilized (eukaryotic such as a mammalian or yeast cell-free translation system or prokaryotic such as a bacterial cell-free translation system.

Nucleic acids encoding any of the various polypeptides disclosed herein may be synthesized chemically. Codon usage may be selected so as to improve expression in a cell. Such codon usage will depend on the cell type selected. Specialized codon usage patterns have been developed for *E. coli* and other bacteria, as well as mammalian cells, plant cells, yeast cells and insect cells. See for example: Mayfield et al., Proc. Natl. Acad. Sci. USA. 2003 100 (2): 438-42; Sinclair et al. Protein Expr. Purif. 2002 (1): 96-105; Connell N D. Curr. Opin. Biotechnol. 2001 12 (5): 446-9; Makrides et al. Microbiol. Rev. 1996 60 (3): 512-38; and Sharp et al. Yeast. 1991 7 (7): 657-78.

Antibodies and antigen binding proteins described herein can also be produced by chemical synthesis (e.g., by the methods described in Solid Phase Peptide Synthesis, 2nd ed., 1984, The Pierce Chemical Co., Rockford, Ill.). Modifications to the protein can also be produced by chemical synthesis.

Antibodies and antigen binding proteins described herein can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, gel filtration, gel permeation chromatography, affinity chromatography, electrophoresis, countercurrent distribution or any combinations of these. After purification, polypeptides may be exchanged into different buffers and/or concentrated by any of a variety of methods known to the art, including, but not limited to, filtration and dialysis.

The purified antibodies and antigen binding proteins described herein are at least 65% pure, at least 75% pure, at least 85% pure, at least 95% pure, or at least 98% pure. Regardless of the exact numerical value of the purity, the polypeptide is sufficiently pure for use as a pharmaceutical product. Any of the dimeric antigen receptors described herein can be expressed by transgenic host cells and then purified to about 65-98% purity or high level of purity using any art-known method.

In certain embodiments, the antibodies and antigen binding proteins herein can further comprise post-translational modifications. Exemplary post-translational protein modifications include phosphorylation, acetylation, methylation, ADP-ribosylation, ubiquitination, glycosylation, carbonylation, sumoylation, biotinylation or addition of a polypeptide side chain or of a hydrophobic group. As a result, the modified polypeptides may contain non-amino acid elements, such as lipids, poly- or mono-saccharide, and phosphates. In one embodiment, glycosylation can be sialylation, which conjugates one or more sialic acid moieties to the polypeptide. Sialic acid moieties improve solubility and serum half-life while also reducing the possible immunogenicity of the protein. See Raju et al. Biochemistry. 2001 31; 40(30):8868-76.

In one embodiment, the antibodies and antigen binding proteins described herein can be modified to become soluble polypeptides which comprises linking the Antibodies and antigen binding proteins to non-proteinaceous polymers. In one embodiment, the non-proteinaccous polymer comprises polyethylene glycol ("PEG"), polypropylene glycol, or polyoxyalkylenes, in the manner as set forth in U.S. Pat. Nos. 4,640,835; 4,496,689; 4,301,144; 4,670,417; 4,791,192 or 4,179,337.

The present disclosure provides therapeutic compositions comprising any of the dimeric antigen receptors described herein in an admixture with a pharmaceutically-acceptable excipient. An excipient encompasses carriers, stabilizers and excipients. Excipients of pharmaceutically acceptable excipients includes for example inert diluents or fillers (e.g., sucrose and sorbitol), lubricating agents, glidants, and anti-adhesives (e.g., magnesium stearate, zinc stearate, stearic acid, silicas, hydrogenated vegetable oils, or talc). Additional examples include buffering agents, stabilizing agents, preservatives, non-ionic detergents, anti-oxidants and isotonifiers.

Therapeutic compositions and methods for preparing them are well known in the art and are found, for example, in "*Remington: The Science and Practice of Pharmacy*" (20th ed., cd. A. R. Gennaro A R., 2000, Lippincott Williams & Wilkins, Philadelphia, Pa.). Therapeutic compositions can be formulated for parenteral administration may, and can for example, contain excipients, sterile water, saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the antibody (or antigen binding protein thereof) described herein. Nanoparticulate formulations (e.g., biodegradable nanoparticles, solid lipid nanoparticles, liposomes) may be used to control the biodistribution of the antibody (or antigen binding protein thereof). Other potentially useful parenteral delivery systems include ethylene-vinyl acetate copolymer particles, osmotic pumps, implantable infusion systems, and liposomes. The concentration of the antibody (or antigen binding protein thereof) in the formulation varies depending upon a number of factors, including the dosage of the drug to be administered, and the route of administration.

Any of the dimeric antigen receptors describe herein may be optionally administered as a pharmaceutically acceptable salt, such as non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include zinc, iron, and the like. In one example, the antibody (or antigen binding portions thereof) is formulated in the presence of sodium acetate to increase thermal stability.

Any of the dimeric antigen receptors described herein may be formulated for oral use include tablets containing the active ingredient(s) in a mixture with non-toxic pharmaceutically acceptable excipients. Formulations for oral use may also be provided as chewable tablets, or as hard gelatin capsules wherein the active ingredient is mixed with an inert solid diluent, or as soft gelatin capsules wherein the active ingredient is mixed with water or an oil medium.

The present disclosure provides dimeric antigen receptors (DARs) comprising a Fab fragment joined to a transmembrane region and intracellular signaling regions. In one embodiment, the DAR construct includes an optional hinge region between the Fab fragment and the transmembrane region. The present disclosure of DAR structures provides unexpected and surprising results that compare a DAR structure having a Fab format antibody to a CAR structure having an scFv format of the same antibody. Moreover, the DAR and CAR formats directly compare because the hinge regions, transmembrane regions and two intracellular signaling regions are the same. Yet the activity of the DAR format was superior to its corresponding CAR format.

The present disclosure provides dimeric antigen receptors (DAR) constructs comprising a heavy chain binding region on one polypeptide chain and a light chain binding region on a separate polypeptide chain. The two polypeptide chains that make up the dimeric antigen receptors can dimerize to form a protein complex. The dimeric antigen receptors have antibody-like properties as they bind specifically to a target antigen. The dimeric antigen receptors can be used for directed cell therapy.

The present disclosure provides a structure for a DAR (dimeric antigen receptor) construct having a first polypeptide chain and a second polypeptide chain, wherein the first polypeptide chain comprises a heavy chain variable region of an antibody and the second polypeptide chain comprises a light chain variable region of an antibody, wherein the first polypeptide chain is linked to the second polypeptide chain by one or a plurality of disulfide bonds at regions outside of a transduced cell when both the first polypeptide chain and the second polypeptide chain are expressed by a same cell. More specifically, a DAR construct comprises a first polypeptide chain comprising, in sequence, an antibody heavy chain (or light chain) with a variable domain region and a CH1 region (kappa (K) or lambda (L)) with a corresponding CL/CK region, a hinge region, a transmembrane region, and one or two signaling domains and a second polypeptide chain comprising, and an antibody light chain (or heavy chain) variable domain region (kappa (K) or lambda (L)) with a corresponding CL/CK region, wherein the CH regions in each first and second polypeptide chains are linked with one or two disulfide bonds at a hinge sequence.

The present disclosure provides a structure for a DAR (dimeric antigen receptor) construct having a first polypeptide chain and a second polypeptide chain, wherein the first polypeptide chain comprises a heavy chain variable region of an antibody and the second polypeptide chain comprises a light chain variable region of an antibody, wherein the first polypeptide chain is linked to the second polypeptide chain by one or a plurality of disulfide bonds at regions outside of a transduced cell when both the first polypeptide chain and the second polypeptide chain are expressed by a same cell. More specifically, a DAR construct comprises a first polypeptide chain comprising, in sequence, an antibody heavy chain with a variable domain region and a CH1 region (kappa (K) or lambda (L)) with a corresponding CL/CK region, a hinge region, a transmembrane region, and one or two signaling domains and a second polypeptide chain comprising, an antibody light chain variable domain region (kappa or lambda) with a corresponding CL/CK region, wherein the CH regions in each first and second polypeptide chains are linked with one or two disulfide bonds at the hinge sequence.

In one embodiment, the DAR construct comprises an antibody heavy chain variable region and an antibody light chain variable region on separate polypeptide chains, wherein the heavy chain variable region and the light chain variable region form an antigen binding domain.

In one embodiment, the hinge region is about 10 to about 100 amino acids in length. In one embodiment, the hinge region is independently selected from the group consisting of a CD8 hinge region or a fragment thereof, a CD8a hinge region or a fragment thereof, a hinge region of an antibody (IgG, IgA, IgM, IgE, or IgD) joining the constant domains CH1 and CH2 of an antibody. The hinge region can be derived from an antibody and may or may not comprise one or more constant regions of the antibody.

In one embodiment, the transmembrane domain can be derived from a membrane protein sequence region selected from the group consisting of CD8α, CD8β, 4-1BB/CD137, CD28, CD34, CD4, FcεRIγ, CD16, OX40/CD134, CD3ζ, CD3ε, CD3γ, CD3δ, TCRα, TCRβ, TCRζ, CD32, CD64, CD64, CD45, CD5, CD9, CD22, CD33, CD37, CD64, CD80, CD86, CD137, CD154, LFA-1 T cell co-receptor, CD2 T cell co-receptor/adhesion molecule, CD40, CD40L/CD154, VEGFR2, FAS, and FGFR2B.

In one embodiment, the signaling region is selected from the group consisting of signaling regions from CD3-zeta chain, 4-1BB, CD28, CD27, OX40, CD30, CD40, PD-1, ICOS, lymph oocyte function-associated antigen-1 (LFA-1), CD2, CD7, LIGHT, NKG2C, B7-H3, GITR (TNFRSF18), DR3 (TNFRSF25), TNFR2, CD226, and combinations thereof.

In one embodiment, a general design of a dimeric antigen receptor includes a first polypeptide chain and a second polypeptide chain, wherein the first polypeptide chain comprises an antigen binding region connected to a dimerization region, connected to a hinge region, connected to a transmembrane region, and connected to one or a plurality of intracellular signaling sequence region(s), and wherein the second polypeptide chain comprises an antigen binding domain and a dimerization domain. In one embodiment, the antigen binding domain on one or both of the first and the second polypeptide chains is selected from the group consisting of a heavy chain variable region, a light chain variable region, an extracellular region of a cytokine receptor, a single domain antibody, and combinations thereof. In one embodiment, the dimerization domain on one or both of the first and second polypeptide chains is selected from the group consisting of a kappa light chain constant region, a lambda light chain constant region, a leucine zipper, myc-max components, and combinations thereof. In FIGS. 1-4, the "S—S" represents any chemical bond or association that results in dimerization of the first and second polypeptide chains, including disulfide bond, leucine zipper or myc-max components.

Figure 2:
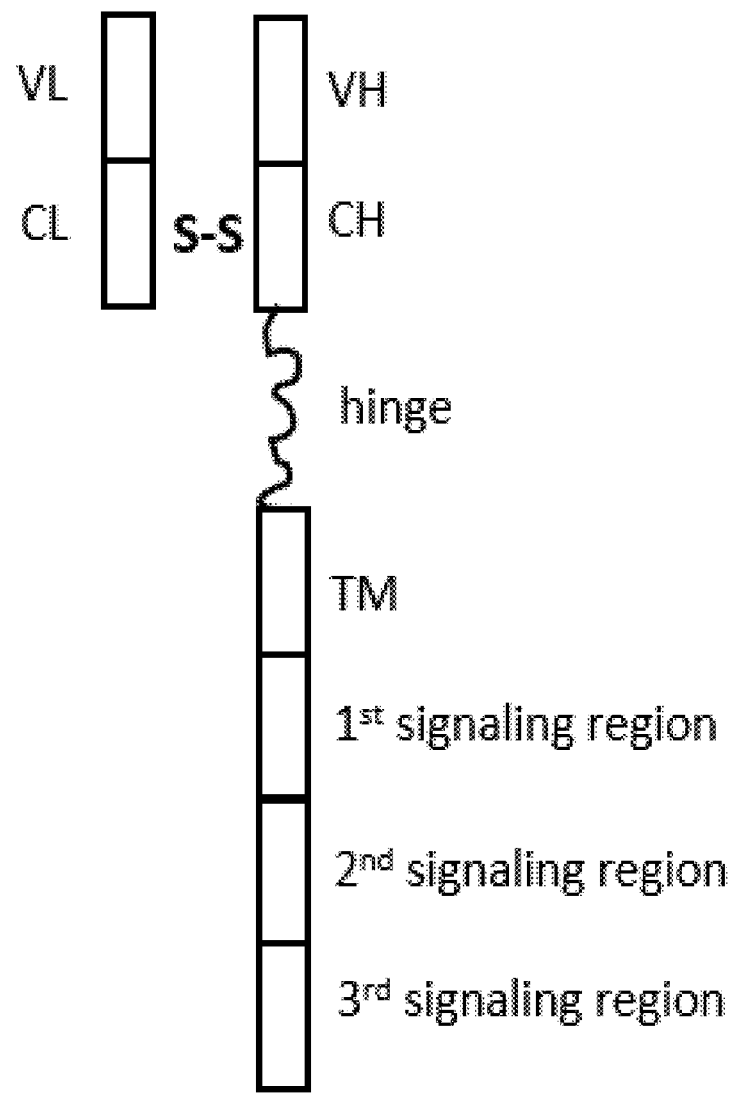
FIG. 2 is a schematic showing an exemplary dimeric antigen receptor comprising three intracellular signaling sequences.

The present disclosure provides dimeric antigen receptors (DAR) constructs where the first polypeptide chain carries the heavy chain variable (VH) and heavy chain constant regions (CH), and the second polypeptide chain carries the light chain variable (VL) and light chain constant regions (CL) (e.g., FIGS. 1 and 2). In one embodiment, the dimeric antigen receptors (DAR) construct comprises: (a) a first polypeptide chain comprising five regions ordered from the amino terminus to the carboxyl terminus: (i) an antibody heavy chain variable region (VH), (ii) an antibody heavy chain constant region (CH), (iii) an optional hinge region, (iv) a transmembrane region (TM), and (v) an intracellular signaling region; (b) a second polypeptide chain comprising two regions ordered from the amino terminus to the carboxyl terminus: (i) an antibody light chain variable region (VL) (e.g., kappa or lambda), and (ii) an antibody light chain constant region (CL).

Figure 3:
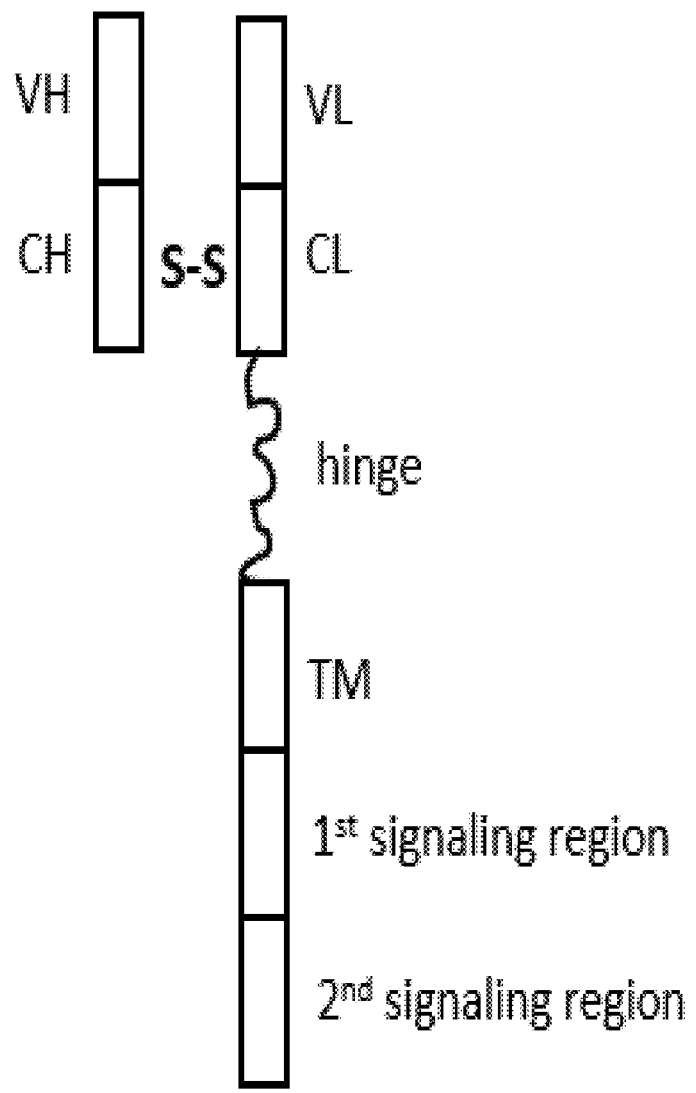
FIG. 3 is a schematic showing an exemplary dimeric antigen receptor comprising two intracellular signaling sequences.
Figure 4:
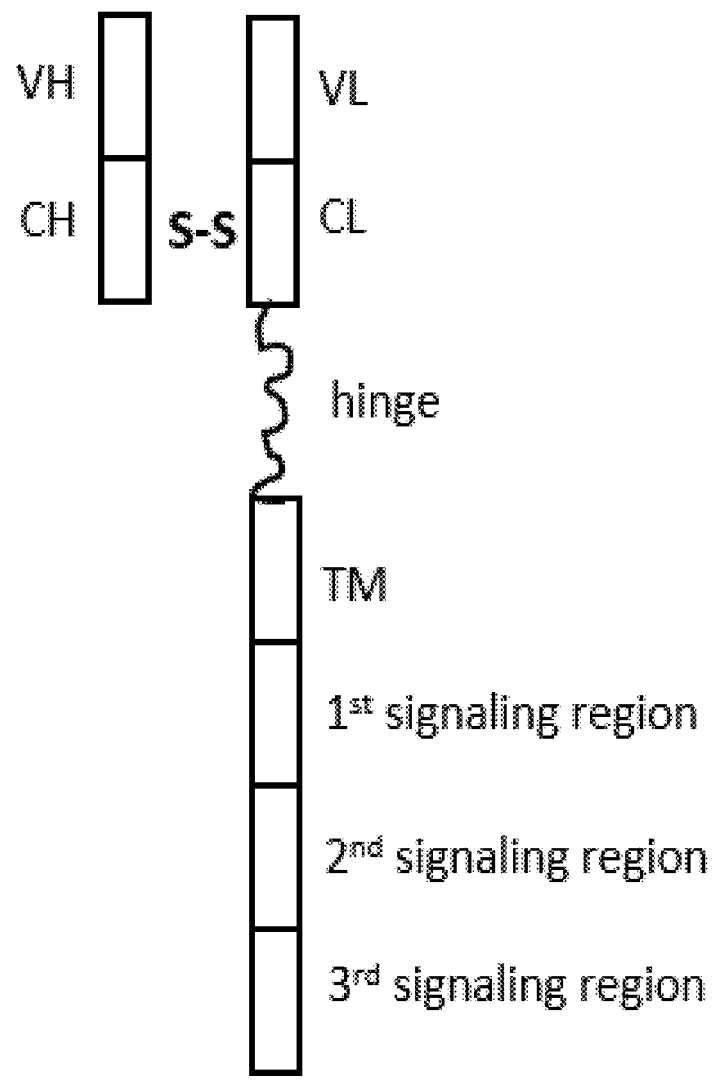
FIG. 4 is a schematic showing an exemplary dimeric antigen receptor comprising three intracellular signaling sequences.

The present disclosure provides dimeric antigen receptors (DAR) constructs where the first polypeptide chain carries the light chain variable (VL) and light chain constant regions (CL), and the second polypeptide chain carries the heavy chain variable (VH) and heavy chain constant regions (CH) (e.g., FIGS. 3 and 4). In one embodiment, the dimeric antigen receptors (DAR) constructs comprises (a) a first polypeptide chain comprising five regions ordered from the amino terminus to the carboxyl terminus: (i) an antibody light chain variable region (VL), (ii) an antibody light chain constant region (CL), (iii) an optional hinge region, (iv) a transmembrane region (TM), and (v) an intracellular signaling region; (b) a second polypeptide chain comprising two regions ordered from the amino terminus to the carboxyl terminus: (i) an antibody heavy chain variable region (VH), and (ii) an antibody heavy chain constant region (CH).

In one embodiment, for the dimeric antigen receptors shown in FIGS. 1-4, the antibody heavy chain constant region (CH) and the antibody light chain constant region (CL) can dimerize to form a dimerization domain. In one embodiment, the antibody heavy chain constant region and the antibody light chain constant region dimerize via one or two disulfide bonds.

In one embodiment, for the dimeric antigen receptors shown in FIGS. 1-4, the antibody heavy chain variable region (VH) and the antibody light chain variable region (VL) associate with each other to form an antigen binding domain. For example, the antibody heavy chain variable region and the antibody light chain variable region associate with each other when the antibody heavy chain constant region and the antibody light chain constant region dimerize.

In one embodiment, for the dimeric antigen receptors shown in FIGS. 1-4, the antigen binding domain, which is formed from the antibody heavy chain variable region and the antibody light chain variable region, binds a target antigen.

In one embodiment, for the dimeric antigen receptors shown in FIGS. 1-4, the antibody heavy chain variable region and the antibody light chain variable region are fully human antibody regions.

In one embodiment, for the dimeric antigen receptors shown in FIGS. 1-4, the hinge region is about 10 to about 100 amino acids in length. In one embodiment, the hinge region comprises a hinge region or a fragment thereof from an antibody (e.g., IgG, IgA, IgM, IgE, or IgD). In one embodiment, the hinge region comprises a CD8 (e.g., CD8α) or CD28 hinge region or a fragment thereof. In one embodiment, the hinge region comprises a CPPC or SPPC amino acid sequence. In one embodiment, the hinge region comprises both CD8 and CD28 hinge sequences (e.g., long hinge region), only CD8 sequence (short hinge) or only CD28 hinge sequence (e.g., short hinge region).

In one embodiment, for the dimeric antigen receptors shown in FIGS. 1-4, the transmembrane regions of the first and second polypeptide chains can be independently derived from CD8α, CD8β, 4-1BB/CD137, CD28, CD34, CD4, FcεRIγ, CD16, OX40/CD134, CD3, CD3ε, CD3γ, CD3δ, TCRα, TCRβ, TCRζ, CD32, CD64, CD64, CD45, CD5, CD9, CD22, CD33, CD37, CD64, CD80, CD86, CD137, CD154, LFA-1 T cell co-receptor, CD2 T cell co-receptor/adhesion molecule, CD40, CD40L/CD154, VEGFR2, FAS, and FGFR2B.

In one embodiment, for the dimeric antigen receptors shown in FIGS. 1-4, the intracellular signaling region of the first polypeptide comprises intracellular signaling sequences in any order and of any combination of two to five signaling sequences from 4-1BB, CD3zeta, CD28, CD27, OX40, CD30, CD40, PD-1, ICOS, lymphocyte function-associated antigen-1 (LFA-1), CD2, CD7, LIGHT, NKG2C, B7-H3, GITR (TNFRSF18), DR3 (TNFRSF25), TNFR2, CD226, and combinations thereof. In one embodiment, the intracellular signaling region comprises intracellular signaling sequences from any one or any combination of two or more of CD28, 4-1BB and/or CD3-zeta. In one embodiment, the intracellular signaling region comprises CD28 and CD3-zeta intracellular signaling sequences, or 4-1BB and CD3-zeta intracellular signaling sequences. In one embodiment, the CD3-zeta portion of the intracellular signaling region comprises ITAM (immunoreceptor tyrosine-based activation motif) motifs 1, 2 and 3 (e.g., long CD3-zeta). In one embodiment, the CD3-zeta portion of the intracellular signaling region comprises only one of the ITAM motifs such as only ITAM 1, 2 or 3 (e.g., short CD3-zeta).

The present disclosure provides dimeric antigen receptors (DAR) constructs having first and second polypeptide chains that associate with each other to form an antigen binding domain that binds a CD38 protein antigen. In one embodiment, the CD38 protein is from human, cynomolgus and/or mouse. In one embodiment, the CD38 protein comprises wild type or mutant CD38 protein.

In one embodiment, the first polypeptide chain of the dimeric antigen receptor comprises an antibody heavy chain variable region comprising the amino acid sequence of SEQ ID NO: 1. In one embodiment, the antibody heavy chain constant region comprises the amino acid sequence of SEQ ID NO:2. In one embodiment, the hinge region comprises a CD28 hinge comprising the amino acid sequence of SEQ ID NO:5, or a CD8 hinge comprising the amino acid sequence of SEQ ID NO:21, or a hinge region comprising a CD28 and CD8 hinge sequences of SEQ ID NO: 19 (e.g., long hinge). In one embodiment, the transmembrane region is a CD28 transmembrane region comprising the amino acid sequence of SEQ ID NO:6. In one embodiment, the intracellular signaling region comprises any one or any combination of two or more signaling sequences selected from a group consisting of 4-1BB signaling sequence comprising the amino acid sequence of SEQ ID NO:7, CD28 signaling sequence comprising the amino acid sequence of SEQ ID NO:8, CD3zeta (long) signaling sequence comprising the amino acid sequence of SEQ ID NO:9 and/or CD3zeta (short) signaling sequence having an ITAM 3 motif and comprising the amino acid sequence of SEQ ID NO:20. In one embodiment, the first polypeptide chain comprises the amino acid sequence of SEQ ID NO:13 (e.g., with or without the leader sequence underlined in FIG. 35B). In one embodiment, the first polypeptide chain comprises the amino acid sequence of SEQ ID NO:13 and a CD28 signaling sequence (SEQ ID NO: 8) between the 4-1BB and CD3zeta signaling sequences. In one embodiment, the first polypeptide chain comprises the amino acid sequence of SEQ ID NO: 16 (e.g., with or without the leader sequence underlined in FIG. 35C). In one embodiment, the first polypeptide chain comprises the amino acid sequence of SEQ ID NO: 16 and a CD28 signaling sequence (SEQ ID NO: 8) between the 4-1BB and CD3zeta signaling sequences.

In one embodiment, the second polypeptide chain of the dimeric antigen receptor comprises an antibody light chain variable region comprising the amino acid sequence of SEQ ID NO: 3. In one embodiment, the antibody light chain constant region comprises the amino acid sequence of SEQ ID NO:4. In one embodiment, the full length of the second polypeptide chain comprises the amino acid sequence of SEQ ID NO: 14 (e.g., with or without the leader sequence underlined in FIG. 35B). In one embodiment, the full length of the second polypeptide chain comprises the amino acid sequence of SEQ ID NO:17 (e.g., with or without the leader sequence underlined in FIG. 35C).

The present disclosure provides a dimeric antigen receptor (DAR) construct comprising: (a) a first polypeptide chain comprising five regions ordered from the amino terminus to the carboxyl terminus: (i) a CD38 antibody heavy chain variable region comprising the amino acid sequence of SEQ ID NO:1, (ii) a CD38 antibody heavy chain constant region comprising the amino acid sequence of SEQ ID NO:2, (iii) a CD28 hinge region comprising the amino acid sequence of SEQ ID NO:5, (iv) a CD28 transmembrane region comprising the amino acid sequence of SEQ ID NO:6, and (v) an intracellular signaling region comprising a 4-1BB intracellular signaling sequence comprising the amino acid sequence of SEQ ID NO:7 and a CD3zeta intracellular signaling sequence comprising the amino acid sequence of SEQ ID NO:9; and (b) a second polypeptide chain comprising two regions ordered from the amino terminus to the carboxyl terminus: (i) a CD38 antibody light chain variable region comprising the amino acid sequence of SEQ ID NO:3, and (ii) a CD38 antibody light chain constant region comprising the amino acid sequence of SEQ ID NO:4, wherein the antibody heavy chain constant region and the antibody light chain constant region form a dimerization domain, and wherein the antibody heavy chain variable region and the antibody light chain variable region form an antigen binding domain that binds a CD38 protein (e.g., FIG. 1).

The present disclosure provides a dimeric antigen receptor (DAR) construct comprising: (a) a first polypeptide chain comprising five regions ordered from the amino terminus to the carboxyl terminus: (i) a CD38 antibody heavy chain variable region comprising the amino acid sequence of SEQ ID NO:1, (ii) a CD38 antibody heavy chain constant region comprising the amino acid sequence of SEQ ID NO:2, (iii) a CD28 hinge region comprising the amino acid sequence of SEQ ID NO:5, (iv) a CD28 transmembrane region comprising the amino acid sequence of SEQ ID NO:6, and (v) an intracellular signaling region comprising a 4-1BB intracellular signaling sequence comprising the amino acid sequence of SEQ ID NO:7 and a CD3zeta intracellular signaling sequence having ITAM 3 motif and comprising the amino acid sequence of SEQ ID NO:20; and (b) a second polypeptide chain comprising two regions ordered from the amino terminus to the carboxyl terminus: (i) a CD38 antibody light chain variable region comprising the amino acid sequence of SEQ ID NO:3, and (ii) a CD38 antibody light chain constant region comprising the amino acid sequence of SEQ ID NO:4, wherein the antibody heavy chain constant region and the antibody light chain constant region form a dimerization domain, and wherein the antibody heavy chain variable region and the antibody light chain variable region form an antigen binding domain that binds a CD38 protein (e.g., FIG. 1).

The present disclosure provides a Version 1 (e.g., V1) dimeric antigen receptors (DAR) construct comprising a first polypeptide chain carrying heavy chain variable (VH) and heavy chain constant regions (CH), and a second polypeptide chain carrying light chain variable (VL) and light chain constant regions (CL) (e.g., FIG. 1), wherein (a) the first polypeptide chain comprising five regions ordered from the amino terminus to the carboxyl terminus: (i) an antibody heavy chain variable region (VH), (ii) an antibody heavy chain constant region (CH), (iii) a long hinge region comprising CD8 and CD28 hinge sequences (e.g., SEQ ID NO:19), (iv) a transmembrane region (TM) comprising CD28 transmembrane sequence (e.g., SEQ ID NO:6), and (v) an intracellular signaling region comprising CD28 signaling sequence (e.g., SEQ ID NO: 8) and CD3-zeta signaling sequence having ITAM motifs 1, 2 and 3 (e.g., SEQ ID NO:9); (b) a second polypeptide chain comprising two regions ordered from the amino terminus to the carboxyl terminus: (i) an antibody light chain variable region (VL) (e.g., kappa or lambda), and (ii) an antibody light chain constant region (CL). In one embodiment, the antibody heavy chain variable region (VH) comprises an anti-CD38 heavy chain variable region sequence (e.g., SEQ ID NO: 1) and the antibody heavy chain constant region (CH) comprises an anti-CD38 heavy chain constant region sequence (e.g., SEQ ID NO:2).

The present disclosure provides a Version 2 (e.g., V2) dimeric antigen receptors (DAR) construct comprising a first polypeptide chain carrying heavy chain variable (VH) and heavy chain constant regions (CH), and a second polypeptide chain carrying light chain variable (VL) and light chain constant regions (CL) (e.g., FIGS. 1 and 2), wherein (a) the first polypeptide chain comprising five regions ordered from the amino terminus to the carboxyl terminus: (i) an antibody heavy chain variable region (VH), (ii) an antibody heavy chain constant region (CH), (iii) a short hinge region comprising a CD28 hinge sequence (e.g., SEQ ID NO:5), (iv) a transmembrane region (TM) comprising CD28 transmembrane sequence (e.g., SEQ ID NO: 6), and (v) an intracellular signaling region comprising either (1) a 4-1BB signaling sequence (e.g., SEQ ID NO:7) and CD3-zeta having ITAM motifs 1, 2 and 3 (e.g., SEQ ID NO: 9), or (2) CD28 (e.g., SEQ ID NO:8) signaling sequence and CD3-zeta having ITAM motifs 1, 2 and 3 (e.g., SEQ ID NO:9), or (3) 4-1BB (e.g., SEQ ID NO:7) signaling sequence and CD28 (e.g., SEQ ID NO:8) signaling sequence and CD3-zeta having ITAM motifs 1, 2 and 3 (e.g., SEQ ID NO:9); (b) a second polypeptide chain comprising two regions ordered from the amino terminus to the carboxyl terminus: (i) an antibody light chain variable region (VL) (e.g., kappa or lambda), and (ii) an antibody light chain constant region (CL).

In one embodiment, the Version 2a (V2a) DAR construct comprises the intracellular signaling region having the 4-1BB signaling sequence (e.g., SEQ ID NO:7) and CD3-zeta having ITAM motifs 1, 2 and 3 (e.g., SEQ ID NO:9).

In one embodiment, the Version 2b (V2b) DAR construct comprises the intracellular signaling region having the CD28 (e.g., SEQ ID NO:8) signaling sequence and CD3-zeta having ITAM motifs 1, 2 and 3 (e.g., SEQ ID NO:9).

In one embodiment, the Version 2c (V2c) DAR construct comprises the intracellular signaling region having the 4-1BB (e.g., SEQ ID NO:7) signaling sequence and CD28 (e.g., SEQ ID NO: 8) signaling sequence and CD3-zeta having ITAM motifs 1, 2 and 3 (e.g., SEQ ID NO: 9).

In one embodiment, the DAR V2a and V2b are second generation DAR constructs, while the DAR V2c is a third generation DAR construct. In one embodiment, the antibody heavy chain variable region (VH) comprises an anti-CD38 heavy chain variable region sequence (e.g., SEQ ID NO:1) and the antibody heavy chain constant region (CH) comprises an anti-CD38 heavy chain constant region sequence (e.g., SEQ ID NO:2).

The present disclosure provides a Version 3 (e.g., V3) dimeric antigen receptors (DAR) construct comprising a first polypeptide chain carrying heavy chain variable (VH) and heavy chain constant regions (CH), and a second polypeptide chain carrying light chain variable (VL) and light chain constant regions (CL) (e.g., FIG. 1), wherein (a) the first polypeptide chain comprising five regions ordered from the amino terminus to the carboxyl terminus: (i) an antibody heavy chain variable region (VH), (ii) an antibody heavy chain constant region (CH), (iii) a short hinge region comprising CD28 hinge sequences (e.g., SEQ ID NO:5), (iv) a transmembrane region (TM) comprising CD28 transmembrane sequence (e.g., SEQ ID NO:6), and (v) an intracellular signaling region comprising 4-1BB signaling sequence (e.g., SEQ ID NO: 7) and CD3-zeta signaling sequence having only ITAM motif 3 (e.g., SEQ ID NO:20); (b) a second polypeptide chain comprising two regions ordered from the amino terminus to the carboxyl terminus: (i) an antibody light chain variable region (VL) (e.g., kappa or lambda), and (ii) an antibody light chain constant region (CL). In one embodiment, the antibody heavy chain variable region (VH) comprises an anti-CD38 heavy chain variable region sequence (e.g., SEQ ID NO: 1) and the antibody heavy chain constant region (CH) comprises an anti-CD38 heavy chain constant region sequence (e.g., SEQ ID NO:2).

The present disclosure provides a Version 4 (e.g., V4) dimeric antigen receptors (DAR) construct comprising a first polypeptide chain carrying heavy chain variable (VH) and heavy chain constant regions (CH), and a second polypeptide chain carrying light chain variable (VL) and light chain constant regions (CL), wherein (a) the first polypeptide chain comprising four regions ordered from the amino terminus to the carboxyl terminus: (i) an antibody heavy chain variable region (VH), (ii) an antibody heavy chain constant region (CH), (iii) a transmembrane region (TM) comprising CD28 transmembrane sequence (e.g., SEQ ID NO:6), and (iv) an intracellular signaling region comprising 4-1BB signaling sequence (e.g., SEQ ID NO: 7) and CD3-zeta signaling sequence having only ITAM motif 3 (e.g., SEQ ID NO:20); (b) a second polypeptide chain comprising two regions ordered from the amino terminus to the carboxyl terminus: (i) an antibody light chain variable region (VL) (e.g., kappa or lambda), and (ii) an antibody light chain constant region (CL). The DAR V4 construct lacks a hinge sequence. In one embodiment, the antibody heavy chain variable region (VH) comprises an anti-CD38 heavy chain variable region sequence (e.g., SEQ ID NO: 1) and the antibody heavy chain constant region (CH) comprises an anti-CD38 heavy chain constant region sequence (e.g., SEQ ID NO: 2).

The present disclosure provides precursor polypeptides. In one embodiment, the precursor polypeptide can be processed to become first and second polypeptide chains that associate/assemble to form dimeric antigen receptors (DAR) constructs.

Figure 5:
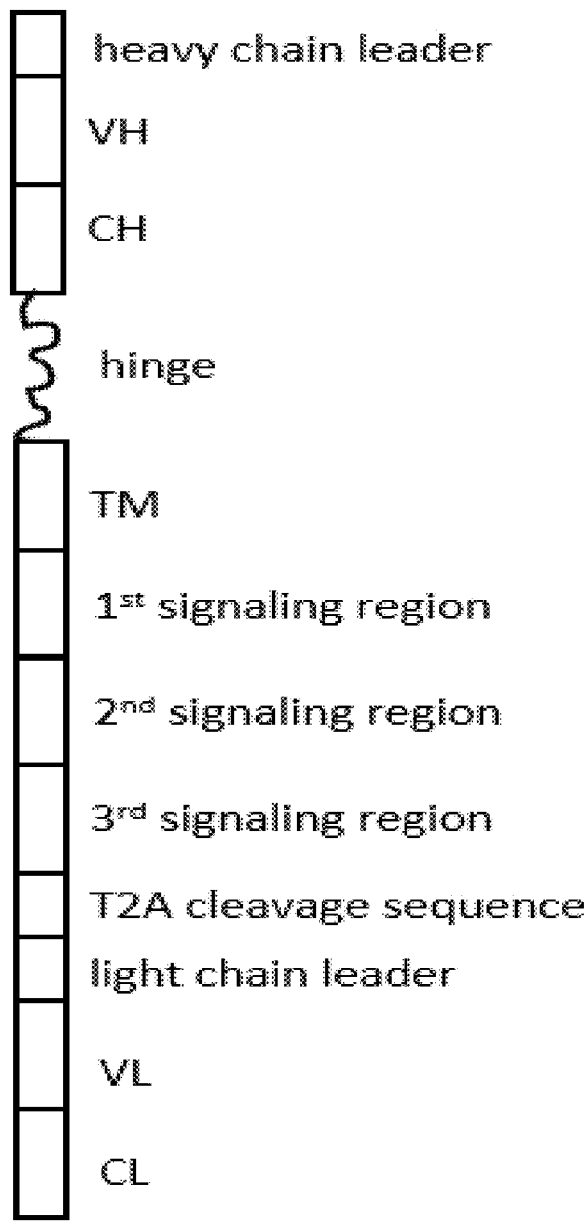
FIG. 5 is a schematic showing an exemplary precursor polypeptide molecule comprising a T2A cleavage sequence and three intracellular signaling sequences.
Figure 6:
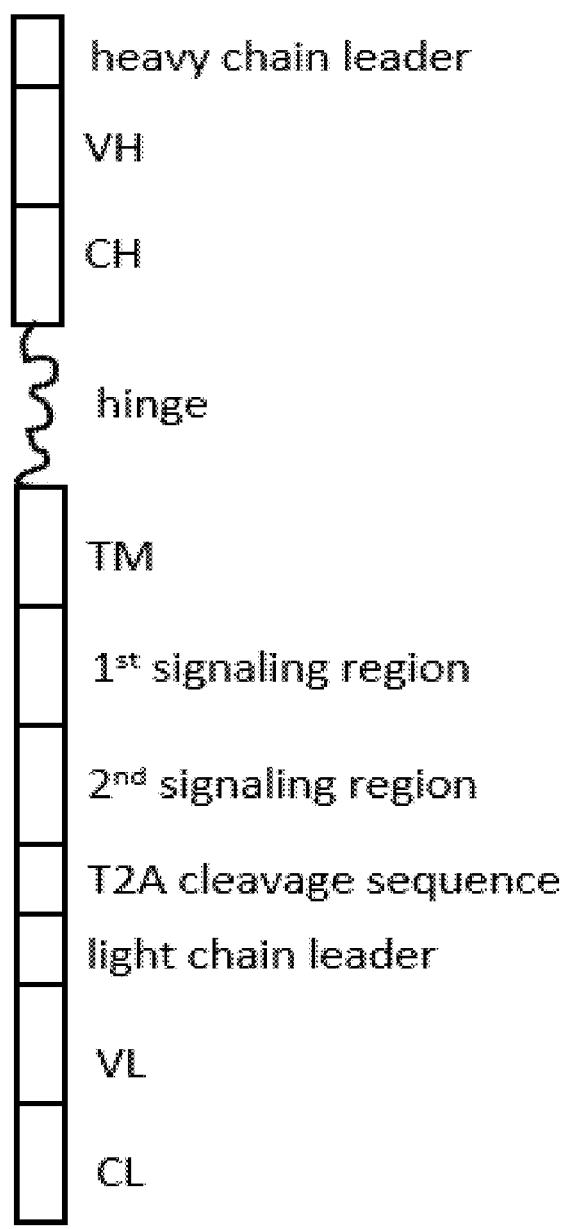
FIG. 6 is a schematic showing an exemplary precursor polypeptide molecule comprising a T2A cleavage sequence and two intracellular signaling sequences.

The present disclosure provides precursor polypeptides comprising ten regions ordered from the amino terminus to the carboxyl terminus: (1) a heavy chain leader sequence (2) an antibody heavy chain variable region, (3) an antibody heavy chain constant region, (4) an optional hinge region, (5) a transmembrane region, (6) an intracellular signaling region, (7) a T2A cleavage sequence, (8) a light chain leader sequence, (9) an antibody light chain variable region, and (10) an antibody light chain constant region (FIGS. 5 and 6). In a non-limiting example, the intracellular signaling region comprises intracellular signaling sequences of any combination of at least two of 4-1BB, CD3zeta and/or CD28 (FIGS. 5 and 6). The skilled artisan will appreciate that combinations of other intracellular signaling sequences are possible. The T2A cleavage sequence is an amino acid sequence that promotes ribosomal skipping and recommencement of protein translation which generates two separate polypeptides. In one embodiment, a population of precursor polypeptides includes a mixture of polypeptides that have been cleaved at the T2A cleavage sequence or not, and/or a mixture of polypeptides that have been cleaved at the heavy chain and/or light chain leader sequences or not.

Figure 7:
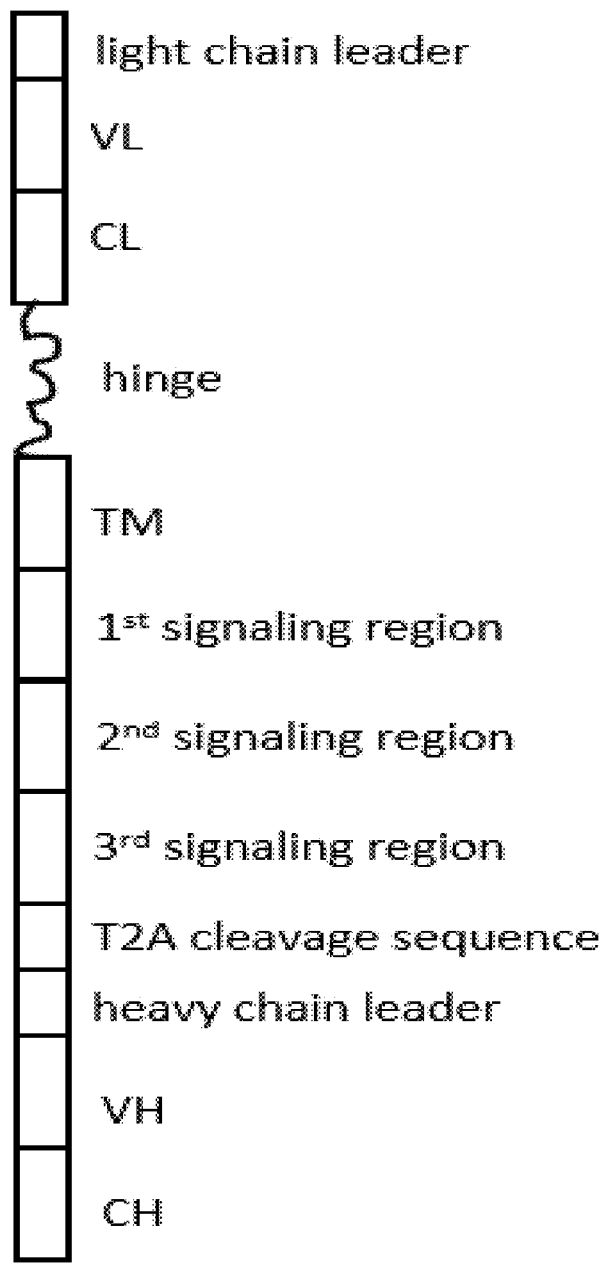
FIG. 7 is a schematic showing an exemplary precursor polypeptide molecule comprising a T2A cleavage sequence and three intracellular signaling sequences.
Figure 8:
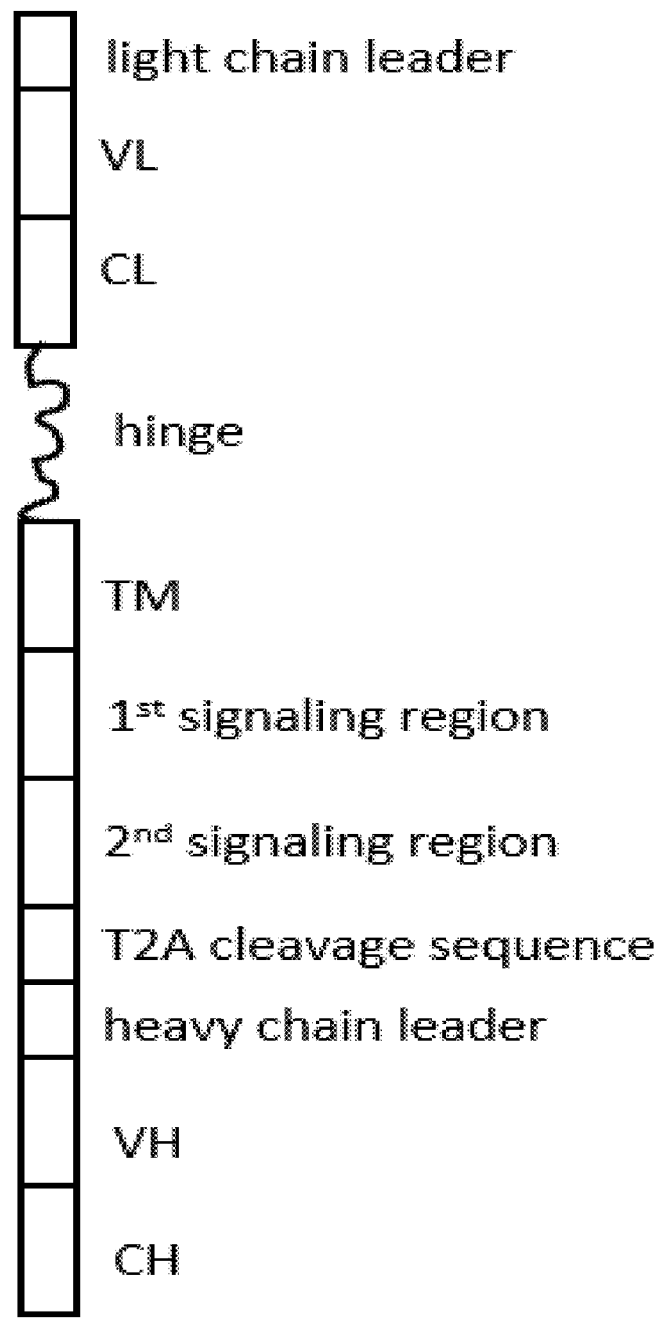
FIG. 8 is a schematic showing an exemplary precursor polypeptide molecule comprising a T2A cleavage sequence and two intracellular signaling sequences.

The present disclosure provides precursor polypeptides comprising ten regions ordered from the amino terminus to the carboxyl terminus: (1) a light chain leader sequence (2) an antibody light chain variable region, (3) an antibody light chain constant region, (4) an optional hinge region, (5) a transmembrane region, (6) an intracellular signaling region, (7) a T2A cleavage sequence, (8) a heavy chain leader sequence, (9) an antibody heavy chain variable region, and (10) an antibody heavy chain constant region (FIGS. 7 and 8). In a non-limiting example, the intracellular signaling region comprises intracellular signaling sequences of any combination of at least two of 4-1BB, CD3zeta and/or CD28 (FIGS. 7 and 8). The skilled artisan will appreciate that combinations of other intracellular signaling sequences are possible. The T2A cleavage sequence is an amino acid sequence that promotes ribosomal skipping and recommencement of protein translation which generates two separate polypeptides. In one embodiment, a population of precursor polypeptides includes a mixture of polypeptides that have been cleaved at the T2A cleavage sequence or not, and/or a mixture of polypeptides that have been cleaved at the heavy chain and/or light chain leader sequences or not.

In one embodiment, for the precursor polypeptides shown in FIGS. 5-8, the heavy chain and light chain leader sequences comprise peptide signal sequences that target a polypeptide chain (e.g., first and second polypeptide chains) to the secretory pathway of a cell and will allow for integration and anchoring of the polypeptide into the lipid bilayer of the cellular membrane. The heavy and light chain leader sequence can direct transport of the precursor polypeptide from the cytosol to the endoplasmic reticulum of a host cell. The heavy chain and light chain leader sequences include signal sequences comprising CD8α, CD28 or CD16 leader sequences.

In one embodiment, for the precursor polypeptides shown in FIGS. 5-8, the N-terminal end of a precursor polypeptide includes a first peptide signal sequence (e.g., heavy chain or light chain leader sequence).

In one embodiment, for the precursor polypeptides shown in FIGS. 5-8, the precursor polypeptide can include a second peptide signal sequence (e.g., heavy chain or light chain leader sequence) located after a cleavage sequence.

In one embodiment, the precursor polypeptide can be cleaved at the cleavage sequence thereby generating first and second polypeptide chains each having a peptide signal sequence at their N-terminal ends.

In one embodiment, for the precursor polypeptides shown in FIGS. 5-8, the processing of the precursor polypeptide includes cleaving the precursor into first and second polypeptide chains, secreting the precursor, and/or anchoring the precursor in a cellular membrane.

In one embodiment, for the precursor polypeptides shown in FIGS. 5-8, after the precursor polypeptide chain is cleaved to generate first and second polypeptide chains, the antibody heavy chain constant region (CH) (of one of the polypeptide chains) and the antibody light chain constant region (CL) (of the other polypeptide chain) can dimerize to form a dimerization domain. In one embodiment, the antibody heavy chain constant region and the antibody light chain constant region dimerize via one or two disulfide bonds.

In one embodiment, for the precursor polypeptides shown in FIGS. 5-8, after the precursor polypeptide chain is cleaved to generate first and second polypeptide chains, the antibody heavy chain variable region (VH) (of one of the polypeptide chains) and the antibody light chain variable region (VL) (of the other polypeptide chain) associate with each other to form an antigen binding domain. For example, the antibody heavy chain variable region and the antibody light chain variable region associate with each other when the antibody heavy chain constant region and the antibody light chain constant region dimerize.

In one embodiment, for the precursor polypeptides shown in FIGS. 5-8, the antigen binding domain, which is formed from the antibody heavy chain variable region and the antibody light chain variable region, binds a target antigen.

In one embodiment, for the precursor polypeptides shown in FIGS. 5-8, the antibody heavy chain variable region and the antibody light chain variable region are fully human antibody regions.

In one embodiment, for the precursor polypeptides shown in FIGS. 5-8, the hinge region is about 10 to about 100 amino acids in length. In one embodiment, the hinge region comprises a hinge region or a fragment thereof from an antibody (e.g., IgG, IgA, IgM, IgE, or IgD). In one embodiment, the hinge region comprises a CD8 (e.g., CD8α) or CD28 hinge region or a fragment thereof. In one embodiment, the hinge region comprises a CPPC or SPPC amino acid sequence. In one embodiment, the hinge region comprises both CD8 and CD28 hinge sequences (e.g., long hinge region), only CD8 sequence (short hinge) or only CD28 hinge sequence (e.g., short hinge region).

In one embodiment, for the precursor polypeptides shown in FIGS. 5-8, the transmembrane regions of the precursor polypeptide chain can be derived from CD8α, CD8β, 4-1BB/CD137, CD28, CD34, CD4, FcεRIγ, CD16, OX40/CD134, CD3ζ, CD3ε, CD3Y, CD3δ, TCRα, TCRβ, TCR, CD32, CD64, CD64, CD45, CD5, CD9, CD22, CD33, CD37, CD64, CD80, CD86, CD137, CD154, LFA-1 T cell co-receptor, CD2 T cell co-receptor/adhesion molecule, CD40, CD40L/CD154, VEGFR2, FAS, and FGFR2B.

In one embodiment, for the precursor polypeptides shown in FIGS. 5-8, the intracellular signaling region of the first polypeptide comprises intracellular signaling sequences in any order and of any combination of two to five signaling sequences from 4-1BB, CD3zeta, CD28, CD27, OX40, CD30, CD40, PD-1, ICOS, lymphocyte function-associated antigen-1 (LFA-1), CD2, CD7, LIGHT, NKG2C, B7-H3, GITR (TNFRSF18), DR3 (TNFRSF25), TNFR2 and/or CD226. In one embodiment, the intracellular signaling region comprises intracellular signaling sequences from any one or any combination of two or more of CD28, 4-1BB and/or CD3-zeta. In one embodiment, the intracellular signaling region comprises CD28 and CD3-zeta intracellular signaling sequences, or 4-1BB and CD3-zeta intracellular signaling sequences. In one embodiment, the CD3-zeta portion of the intracellular signaling region comprises ITAM (immunoreceptor tyrosine-based activation motif) motifs 1, 2 and 3 (e.g., long CD3-zeta). In one embodiment, the CD3-zeta portion of the intracellular signaling region comprises only one of the ITAM motifs such as only ITAM 1, 2 or 3 (e.g., short CD3-zeta).

The present disclosure provides a precursor polypeptide, comprising ten regions: (1) a heavy chain leader sequence comprising the amino acid sequence of SEQ ID NO: 10; (2) a CD38 antibody heavy chain variable region comprising the amino acid sequence of SEQ ID NO: 1; (3) a CD38 antibody heavy chain constant region comprising the amino acid sequence of SEQ ID NO: 2; (4) a CD28 hinge region comprising the amino acid sequence of SEQ ID NO:5 and optionally a CD8 hinge comprising the amino acid sequence of SEQ ID NO:21; (5) a CD28 transmembrane region comprising the amino acid sequence of SEQ ID NO:6; (6) an intracellular signaling region comprising any one or any combination of three or more signaling sequences selected from a group consisting of 4-1BB signaling sequence comprising the amino acid sequence of SEQ ID NO:7, CD28 signaling sequence comprising the amino acid sequence of SEQ ID NO:8, CD3zeta (long) signaling sequence comprising the amino acid sequence of SEQ ID NO: 9 and/or CD3zeta (short) signaling sequence having an ITAM 3 motif and comprising the amino acid sequence of SEQ ID NO:20; (7) a T2A cleavage sequence comprising the amino acid sequence of SEQ ID NO: 12; (8) a light chain leader sequence comprising the amino acid sequence of SEQ ID NO:11; (9) a CD38 antibody light chain variable region comprising the amino acid sequence of SEQ ID NO:3; and (10) a CD38 antibody light chain constant region comprising the amino acid sequence of SEQ ID NO:4. In one embodiment, the full length precursor polypeptide comprises the amino acid sequence of SEQ ID NO: 15 or 18. In one embodiment, the full length precursor polypeptide comprises the amino acid sequence of SEQ ID NO: 15 and a CD28 signaling sequence (SEQ ID NO:8) between the 4-1BB and CD3zeta signaling sequences. In one embodiment, the precursor polypeptide can be processed by cleaving at the T2A cleavable sequence to release the first and second polypeptide chains and secreting the precursor, and/or anchoring the precursor in a cellular membrane. The first and second polypeptide chains can dimerize via at least one disulfide bond between the antibody heavy chain constant region and the antibody light chain constant region, and the antibody heavy chain variable region and the antibody light chain variable region can form an antigen binding domain that binds a CD38 antigen. In one embodiment, the hinge region is optional.

The present disclosure provides a precursor polypeptide, comprising ten regions: (1) a heavy chain leader sequence comprising the amino acid sequence of SEQ ID NO: 10; (2) a CD38 antibody heavy chain variable region comprising the amino acid sequence of SEQ ID NO:1; (3) a CD38 antibody heavy chain constant region comprising the amino acid sequence of SEQ ID NO: 2; (4) a CD28 hinge region comprising the amino acid sequence of SEQ ID NO:5; (5) a CD28 transmembrane region comprising the amino acid sequence of SEQ ID NO:6; (6) an intracellular signaling region comprising a 4-1BB signaling sequence comprising the amino acid sequence of SEQ ID NO:7 and CD3zeta (short) signaling sequence having an ITAM 3 motif and comprising the amino acid sequence of SEQ ID NO:20, and optionally a CD28 signaling sequence comprising the amino acid sequence of SEQ ID NO:8; (7) a T2A cleavage sequence comprising the amino acid sequence of SEQ ID NO: 12; (8) a light chain leader sequence comprising the amino acid sequence of SEQ ID NO:11; (9) a CD38 antibody light chain variable region comprising the amino acid sequence of SEQ ID NO:3; and (10) a CD38 antibody light chain constant region comprising the amino acid sequence of SEQ ID NO:4. In one embodiment, the full length precursor polypeptide comprises the amino acid sequence of SEQ ID NO: 18. In one embodiment, the precursor polypeptide can be processed by cleaving at the T2A cleavable sequence to release the first and second polypeptide chains and secreting the precursor, and/or anchoring the precursor in a cellular membrane. In one embodiment, after release of the first and second polypeptide chains, the first polypeptide chain comprises the amino acid sequence of SEQ ID NO: 16 and the second polypeptide chain comprises the amino acid sequence of SEQ ID NO:17. The first and second polypeptide chains can dimerize via at least one disulfide bond between the antibody heavy chain constant region and the antibody light chain constant region, and the antibody heavy chain variable region and the antibody light chain variable region can form an antigen binding domain that binds a CD38 antigen.

The present disclosure provides nucleic acids that encode any of the first polypeptide chains, second polypeptide chains, first and second polypeptide chains, dimeric antigen receptors or precursor polypeptides described herein.

The present disclosure provides a nucleic acid that encodes a first polypeptide chain comprising: five regions ordered from the amino terminus to the carboxyl terminus: (i) an antibody heavy chain variable region, (ii) an antibody heavy chain constant region, (iii) an optional hinge region, (iv) a transmembrane region, and (v) an intracellular signaling region.

The present disclosure provides a nucleic acid that encodes a second polypeptide chain comprising: two regions ordered from the amino terminus to the carboxyl terminus: (i) an antibody light chain variable region, and (ii) an antibody light chain constant region.

In one embodiment, the nucleic acid encodes the first and second polypeptide chains, comprising: (a) a first polypeptide chain comprising five regions ordered from the amino terminus to the carboxyl terminus: (i) an antibody heavy chain variable region, (ii) an antibody heavy chain constant region, (iii) an optional hinge region, (iv) a transmembrane region, and (v) an intracellular signaling region having two to five intracellular signaling sequences; and (b) a second polypeptide chain comprising: two regions ordered from the amino terminus to the carboxyl terminus: (i) an antibody light chain variable region, and (ii) an antibody light chain constant region (e.g., FIGS. 1 and 2).

The present disclosure provides a nucleic acid that encodes a first polypeptide chain comprising: five regions ordered from the amino terminus to the carboxyl terminus: (i) an antibody light chain variable region, (ii) an antibody light chain constant region, (iii) an optional hinge region, (iv) a transmembrane region, and (v) an intracellular signaling region.

The present disclosure provides a nucleic acid that encodes a second polypeptide chain comprising: two regions ordered from the amino terminus to the carboxyl terminus: (i) an antibody heavy chain variable region, and (ii) an antibody heavy chain constant region.

In one embodiment, the nucleic acid encodes the first and second polypeptide chains, comprising: (a) a first polypeptide chain comprising five regions ordered from the amino terminus to the carboxyl terminus: (i) an antibody light chain variable region, (ii) an antibody light chain constant region, (iii) an optional hinge region, (iv) a transmembrane region, and (v) an intracellular signaling region having two to five intracellular signaling sequences; and (b) a second polypeptide chain comprising: two regions ordered from the amino terminus to the carboxyl terminus: (i) an antibody heavy chain variable region, and (ii) an antibody heavy chain constant region (e.g., FIGS. 3 and 4).

The present disclosure provides a nucleic acid that encodes a first polypeptide chain comprising: six regions ordered from the amino terminus to the carboxyl terminus: (i) a heavy chain leader region, (ii) an antibody heavy chain variable region, (iii) an antibody heavy chain constant region, (iv) an optional hinge region, (v) a transmembrane region, and (vi) an intracellular signaling region.

The present disclosure provides a nucleic acid that encodes a second polypeptide chain comprising: three regions ordered from the amino terminus to the carboxyl terminus: (i) a light chain leader region, (ii) an antibody light chain variable region, and (iii) an antibody light chain constant region.

In one embodiment, the nucleic acid encodes the first and second polypeptide chains, comprising: (a) a first polypeptide chain comprising six regions ordered from the amino terminus to the carboxyl terminus: (i) a heavy chain leader sequence, (ii) an antibody heavy chain variable region, (iii) an antibody heavy chain constant region, (iv) an optional hinge region, (v) a transmembrane region, and (vi) an intracellular signaling region having two to five intracellular signaling sequences; and (b) a second polypeptide chain comprising: two regions ordered from the amino terminus to the carboxyl terminus: (i) an antibody light chain variable region, and (ii) an antibody light chain constant region.

The present disclosure provides a nucleic acid that encodes a first polypeptide chain comprising: six regions ordered from the amino terminus to the carboxyl terminus: (i) a light chain leader region, (ii) an antibody light chain variable region, (iii) an antibody light chain constant region, (iv) an optional hinge region, (v) a transmembrane region, and (vi) an intracellular signaling region.

The present disclosure provides a nucleic acid that encodes a second polypeptide chain comprising: three regions ordered from the amino terminus to the carboxyl terminus: (i) a heavy chain leader region, (ii) an antibody heavy chain variable region, and (iii) an antibody light chain constant region.

In one embodiment, the nucleic acid encodes the first and second polypeptide chains, comprising: (a) a first polypeptide chain comprising six regions ordered from the amino terminus to the carboxyl terminus: (i) a light chain leader sequence, (ii) an antibody light chain variable region, (iii) an antibody light chain constant region, (iv) an optional hinge region, (v) a transmembrane region, and (vi) an intracellular signaling region having two to five intracellular signaling sequences; and (b) a second polypeptide chain comprising: two regions ordered from the amino terminus to the carboxyl terminus: (i) an antibody heavy chain variable region, and (ii) an antibody heavy chain constant region.

The present disclosure provides a nucleic acid that encodes a precursor polypeptide comprising: ten regions ordered from the amino terminus to the carboxyl terminus: (1) a heavy chain leader region, (2) an antibody heavy chain variable region, (3) an antibody heavy chain constant region, (4) an optional hinge region, (5) a transmembrane region, (6) an intracellular signaling region having two to five intracellular signaling sequences, (7) T2A cleavable sequence region, (8) a light chain leader region, (9) an antibody light chain variable region, and (10) an antibody light chain constant region (e.g., FIGS. 5 and 6).

The present disclosure provides a nucleic acid that encodes a precursor polypeptide comprising: ten regions ordered from the amino terminus to the carboxyl terminus: (1) a light chain leader region, (2) an antibody light chain variable region, (3) an antibody light chain constant region, (4) an optional hinge region, (5) a transmembrane region, (6) an intracellular signaling region having two to five intracellular signaling sequences, (7) T2A cleavable sequence region, (8) a heavy chain leader region, (9) an antibody heavy chain variable region, and (10) an antibody heavy chain constant region (e.g., FIGS. 7 and 8).

The present disclosure provides nucleic acids that encode a first polypeptide chain comprising five regions ordered from the amino terminus to the carboxyl terminus: (i) a CD38 antibody heavy chain variable region comprising the amino acid sequence of SEQ ID NO:1, (ii) a CD38 antibody heavy chain constant region comprising the amino acid sequence of SEQ ID NO: 2, (iii) a CD28 hinge region comprising the amino acid sequence of SEQ ID NO:5 and optionally a CD8 hinge comprising the amino acid sequence of SEQ ID NO:21, (iv) a CD28 transmembrane region comprising the amino acid sequence of SEQ ID NO:6, and (v) an intracellular signaling region comprising any one or any combination of two or more signaling sequences selected from a group consisting of 4-1BB signaling sequence comprising the amino acid sequence of SEQ ID NO:7, CD28 signaling sequence comprising the amino acid sequence of SEQ ID NO:8, CD3zeta (long) signaling sequence comprising the amino acid sequence of SEQ ID NO:9 and/or CD3zeta (short) signaling sequence having an ITAM 3 motif and comprising the amino acid sequence of SEQ ID NO:20. In one embodiment, the nucleic acid encodes a first polypeptide chain which comprises the amino acid sequence of SEQ ID NO:13 or 16 (e.g., with or without the leader sequence underlined in FIG. 35B or 35C). In one embodiment, the nucleic acid encodes the first polypeptide chain which comprises the amino acid sequence of SEQ ID NO:13 and a CD28 signaling sequence (SEQ ID NO:8) between the 4-1BB and CD3zeta signaling sequences. In one embodiment, the nucleic acid encodes the first polypeptide chain which comprises the amino acid sequence of SEQ ID NO: 16 (e.g., with or without the leader sequence underlined in FIG. 35C). In one embodiment, the nucleic acid encodes the first polypeptide chain which comprises the amino acid sequence of SEQ ID NO:16 and a CD28 signaling sequence (SEQ ID NO:8) between the 4-1BB and CD3zeta signaling sequences. In one embodiment, the hinge region is optional.

In one embodiment, the nucleic acid encodes the second polypeptide chain of the dimeric antigen receptor which comprises an antibody light chain variable region comprising the amino acid sequence of SEQ ID NO:3. In one embodiment, the nucleic acid encodes the second polypeptide chain of the dimeric antigen receptor which comprises the antibody light chain constant region comprises the amino acid sequence of SEQ ID NO:4. In one embodiment, the nucleic acid encodes the full length of the second polypeptide chain which comprises the amino acid sequence of SEQ ID NO: 14 or 17 (e.g., with or without the leader sequence underlined in FIG. 35B or 35C).

The present disclosure provide nucleic acids that encode a second polypeptide chain comprising two regions ordered from the amino terminus to the carboxyl terminus: (i) a CD38 antibody light chain variable region comprising the amino acid sequence of SEQ ID NO:3, and (ii) a CD38 antibody light chain constant region comprising the amino acid sequence of SEQ ID NO: 4.

In one embodiment, the nucleic acid encodes the first polypeptide chain (SEQ ID NO: 13 or 16), a T2A cleavage sequence (SEQ ID NO:12), and the second polypeptide chain (SEQ ID NO:14 or 17). In one embodiment, the first polypeptide chain (SEQ ID NO:13 or 16) includes or lacks the leader sequence underlined in FIGS. 35B and C, respectively. In one embodiment, the second polypeptide chain (SEQ ID NO: 14 or 17) includes or lacks the leader sequence underlined in FIG. 35B or C, respectively.

The present disclosure provides nucleic acids that encode a precursor polypeptide, comprising the amino acid sequence of SEQ ID NO:15 or 18.

The present disclosure provides nucleic acids that encode a Version 1 (e.g., V1) dimeric antigen receptors (DAR) construct comprising a first polypeptide chain carrying heavy chain variable (VH) and heavy chain constant regions (CH), and a second polypeptide chain carrying light chain variable (VL) and light chain constant regions (CL) (e.g., FIG. 1), wherein (a) a first nucleic acid encodes the first polypeptide chain comprising five regions ordered from the amino terminus to the carboxyl terminus: (i) an antibody heavy chain variable region (VH), (ii) an antibody heavy chain constant region (CH), (iii) a long hinge region comprising CD8 and CD28 hinge sequences (e.g., SEQ ID NO:19), (iv) a transmembrane region (TM) comprising CD28 transmembrane sequence (e.g., SEQ ID NO:6), and (v) an intracellular signaling region comprising CD28 signaling sequence (e.g., SEQ ID NO:8) and CD3-zeta signaling sequence having ITAM motifs 1, 2 and 3 (e.g., SEQ ID NO:9); (b) the second nucleic acid encodes a second polypeptide chain comprising two regions ordered from the amino terminus to the carboxyl terminus: (i) an antibody light chain variable region (VL) (e.g., kappa or lambda), and (ii) an antibody light chain constant region (CL). In one embodiment, the antibody heavy chain variable region (VH) comprises an anti-CD38 heavy chain variable region sequence (e.g., SEQ ID NO: 1) and the antibody heavy chain constant region (CH) comprises an anti-CD38 heavy chain constant region sequence (e.g., SEQ ID NO:2).

The present disclosure provides nucleic acids that encode a Version 2 (e.g., V2) dimeric antigen receptors (DAR) construct comprising a first polypeptide chain carrying heavy chain variable (VH) and heavy chain constant regions (CH), and a second polypeptide chain carrying light chain variable (VL) and light chain constant regions (CL) (e.g., FIGS. 1 and 2), wherein (a) a first nucleic acid encodes the first polypeptide chain comprising five regions ordered from the amino terminus to the carboxyl terminus: (i) an antibody heavy chain variable region (VH), (ii) an antibody heavy chain constant region (CH), (iii) a short hinge region comprising a CD28 hinge sequence (e.g., SEQ ID NO:5), (iv) a transmembrane region (TM) comprising CD28 transmembrane sequence (e.g., SEQ ID NO:6), and (v) an intracellular signaling region comprising either (1) a 4-1BB signaling sequence (e.g., SEQ ID NO:7) and CD3-zeta having ITAM motifs 1, 2 and 3 (e.g., SEQ ID NO:9), or (2) CD28 (e.g., SEQ ID NO: 8) signaling sequence and CD3-zeta having ITAM motifs 1, 2 and 3 (e.g., SEQ ID NO:9), or (3) 4-1BB (e.g., SEQ ID NO:7) signaling sequence and CD28 (e.g., SEQ ID NO:8) signaling sequence and CD3-zeta having ITAM motifs 1, 2 and 3 (e.g., SEQ ID NO:9); (b) a second nucleic acid encodes the second polypeptide chain comprising two regions ordered from the amino terminus to the carboxyl terminus: (i) an antibody light chain variable region (VL) (e.g., kappa or lambda), and (ii) an antibody light chain constant region (CL).

In one embodiment, the nucleic acids encode the Version 2a (V2a) DAR construct comprising the intracellular signaling region having the 4-1BB signaling sequence (e.g., SEQ ID NO: 7) and CD3-zeta having ITAM motifs 1, 2 and 3 (e.g., SEQ ID NO:9).

In one embodiment, the nucleic acids encode the Version 2b (V2b) DAR construct comprising the intracellular signaling region having the CD28 (e.g., SEQ ID NO:8) signaling sequence and CD3-zeta having ITAM motifs 1, 2 and 3 (e.g., SEQ ID NO:9).

In one embodiment, the nucleic acids encode the Version 2c (V2c) DAR construct comprising the intracellular signaling region having the 4-1BB (e.g., SEQ ID NO:7) signaling sequence and CD28 (e.g., SEQ ID NO:8) signaling sequence and CD3-zeta having ITAM motifs 1, 2 and 3 (e.g., SEQ ID NO:9). In one embodiment, the DAR V2a and V2b are second generation DAR constructs, while the DAR V2c is a third generation DAR construct. In one embodiment, the antibody heavy chain variable region (VH) comprises an anti-CD38 heavy chain variable region sequence (e.g., SEQ ID NO:1) and the antibody heavy chain constant region (CH) comprises an anti-CD38 heavy chain constant region sequence (e.g., SEQ ID NO:2).

The present disclosure provides nucleic acids that encodes a Version 3 (e.g., V3) dimeric antigen receptors (DAR) construct comprising a first polypeptide chain carrying heavy chain variable (VH) and heavy chain constant regions (CH), and a second polypeptide chain carrying light chain variable (VL) and light chain constant regions (CL) (e.g., FIG. 1), wherein (a) a first nucleic acid encodes the first polypeptide chain comprising five regions ordered from the amino terminus to the carboxyl terminus: (i) an antibody heavy chain variable region (VH), (ii) an antibody heavy chain constant region (CH), (iii) a short hinge region comprising CD28 hinge sequences (e.g., SEQ ID NO:5), (iv) a transmembrane region (TM) comprising CD28 transmembrane sequence (e.g., SEQ ID NO:6), and (v) an intracellular signaling region comprising 4-1BB signaling sequence (e.g., SEQ ID NO:7) and CD3-zeta signaling sequence having only ITAM motif 3 (e.g., SEQ ID NO:20); (b) a second nucleic acid encodes the second polypeptide chain comprising two regions ordered from the amino terminus to the carboxyl terminus: (i) an antibody light chain variable region (VL) (e.g., kappa or lambda), and (ii) an antibody light chain constant region (CL). In one embodiment, the antibody heavy chain variable region (VH) comprises an anti-CD38 heavy chain variable region sequence (e.g., SEQ ID NO: 1) and the antibody heavy chain constant region (CH) comprises an anti-CD38 heavy chain constant region sequence (e.g., SEQ ID NO:2).

The present disclosure provides nucleic acids that encode a Version 4 (e.g., V4) dimeric antigen receptors (DAR) construct comprising a first polypeptide chain carrying heavy chain variable (VH) and heavy chain constant regions (CH), and a second polypeptide chain carrying light chain variable (VL) and light chain constant regions (CL), wherein (a) a first nucleic acid encodes the first polypeptide chain comprising four regions ordered from the amino terminus to the carboxyl terminus: (i) an antibody heavy chain variable region (VH), (ii) an antibody heavy chain constant region (CH), (iii) a transmembrane region (TM) comprising CD28 transmembrane sequence (e.g., SEQ ID NO:6), and (iv) an intracellular signaling region comprising 4-1BB signaling sequence (e.g., SEQ ID NO:7) and CD3-zeta signaling sequence having only ITAM motif 3 (e.g., SEQ ID NO:20); (b) a second nucleic acid encodes the second polypeptide chain comprising two regions ordered from the amino terminus to the carboxyl terminus: (i) an antibody light chain variable region (VL) (e.g., kappa or lambda), and (ii) an antibody light chain constant region (CL). The DAR V4 construct lacks a hinge sequence. In one embodiment, the antibody heavy chain variable region (VH) comprises an anti-CD38 heavy chain variable region sequence (e.g., SEQ ID NO:1) and the antibody heavy chain constant region (CH) comprises an anti-CD38 heavy chain constant region sequence (e.g., SEQ ID NO:2).

The present disclosure provides vectors operably linked to nucleic acids that encode any of the first polypeptide chains, second polypeptide chains, first and second polypeptide chains, dimeric antigen receptors or precursor polypeptide described herein.

The present disclosure provides a vector operably linked to a nucleic acid that encodes a first polypeptide chain comprising: five regions ordered from the amino terminus to the carboxyl terminus: (i) an antibody heavy chain variable region, (ii) an antibody heavy chain constant region, (iii) an optional hinge region, (iv) a transmembrane region, and (v) an intracellular signaling region.

The present disclosure provides a vector operably linked to a nucleic acid that encodes a second polypeptide chain comprising: two regions ordered from the amino terminus to the carboxyl terminus: (i) an antibody light chain variable region, and (ii) an antibody light chain constant region.

In one embodiment, the vector that is operably linked to a nucleic acid encoding the first and second polypeptide chains, comprises: (a) a first polypeptide chain comprising five regions ordered from the amino terminus to the carboxyl terminus: (i) an antibody heavy chain variable region, (ii) an antibody heavy chain constant region, (iii) an optional hinge region, (iv) a transmembrane region, and (v) an intracellular signaling region having two to five intracellular signaling sequences; and (b) a second polypeptide chain comprising: two regions ordered from the amino terminus to the carboxyl terminus: (i) an antibody light chain variable region, and (ii) an antibody light chain constant region.

The present disclosure provides a vector operably linked to a nucleic acid that encodes a first polypeptide chain comprising: five regions ordered from the amino terminus to the carboxyl terminus: (i) an antibody light chain variable region, (ii) an antibody light chain constant region, (iii) an optional hinge region, (iv) a transmembrane region, and (v) an intracellular signaling region.

The present disclosure provides a vector operably linked to a nucleic acid that encodes a second polypeptide chain comprising: two regions ordered from the amino terminus to the carboxyl terminus: (i) an antibody heavy chain variable region, and (ii) an antibody heavy chain constant region.

In one embodiment, the vector that is operably linked to a nucleic acid encoding the first and second polypeptide chains, comprises: (a) a first polypeptide chain comprising five regions ordered from the amino terminus to the carboxyl terminus: (i) an antibody light chain variable region, (ii) an antibody light chain constant region, (iii) an optional hinge region, (iv) a transmembrane region, and (v) an intracellular signaling region having two to five intracellular signaling sequences; and (b) a second polypeptide chain comprising: two regions ordered from the amino terminus to the carboxyl terminus: (i) an antibody heavy chain variable region, and (ii) an antibody heavy chain constant region.

The present disclosure provides a vector operably linked to a nucleic acid that encodes a first polypeptide chain comprising: six regions ordered from the amino terminus to the carboxyl terminus: (i) a heavy chain leader region, (ii) an antibody heavy chain variable region, (iii) an antibody heavy chain constant region, (iv) an optional hinge region, (v) a transmembrane region, and (vi) an intracellular signaling region.

The present disclosure provides a vector operably linked to a nucleic acid that encodes a second polypeptide chain comprising: three regions ordered from the amino terminus to the carboxyl terminus: (i) a light chain leader region, (ii) an antibody light chain variable region, and (iii) an antibody light chain constant region.

In one embodiment, the vector that is operably linked to a nucleic acid encoding the first and second polypeptide chains, comprises: (a) a first polypeptide chain comprising six regions ordered from the amino terminus to the carboxyl terminus: (i) a heavy chain leader sequence, (ii) an antibody heavy chain variable region, (iii) an antibody heavy chain constant region, (iv) an optional hinge region, (v) a transmembrane region, and (vi) an intracellular signaling region having two to five intracellular signaling sequences; and (b) a second polypeptide chain comprising: two regions ordered from the amino terminus to the carboxyl terminus: (i) an antibody light chain variable region, and (ii) an antibody light chain constant region.

The present disclosure provides a vector operably linked to a nucleic acid that encodes a first polypeptide chain comprising: six regions ordered from the amino terminus to the carboxyl terminus: (i) a light chain leader region, (ii) an antibody light chain variable region, (iii) an antibody light chain constant region, (iv) an optional hinge region, (v) a transmembrane region, and (vi) an intracellular signaling region.

The present disclosure provides a vector operably linked to a nucleic acid that encodes a second polypeptide chain comprising: three regions ordered from the amino terminus to the carboxyl terminus: (i) a heavy chain leader region, (ii) an antibody heavy chain variable region, and (iii) an antibody light chain constant region.

In one embodiment, the vector that is operably linked to a nucleic acid encoding the first and second polypeptide chains, comprises: (a) a first polypeptide chain comprising six regions ordered from the amino terminus to the carboxyl terminus: (i) a light chain leader sequence, (ii) an antibody light chain variable region, (iii) an antibody light chain constant region, (iv) an optional hinge region, (v) a transmembrane region, and (vi) an intracellular signaling region having two to five intracellular signaling sequences; and (b) a second polypeptide chain comprising: two regions ordered from the amino terminus to the carboxyl terminus: (i) an antibody heavy chain variable region, and (ii) an antibody heavy chain constant region.

The present disclosure provides a vector operably linked to a nucleic acid that encodes a precursor polypeptide comprising: ten regions ordered from the amino terminus to the carboxyl terminus: (1) a heavy chain leader region, (2) an antibody heavy chain variable region, (3) an antibody heavy chain constant region, (4) an optional hinge region, (5) a transmembrane region, (6) an intracellular signaling region having two to five intracellular signaling sequences, (7) T2A cleavable sequence region, (8) a light chain leader region, (9) an antibody light chain variable region, and (10) an antibody light chain constant region.

The present disclosure provides a vector operably linked to a nucleic acid that encodes a precursor polypeptide comprising: ten regions ordered from the amino terminus to the carboxyl terminus: (1) a light chain leader region, (2) an antibody light chain variable region, (3) an antibody light chain constant region, (4) an optional hinge region, (5) a transmembrane region, (6) an intracellular signaling region having two to five intracellular signaling sequences, (7) T2A cleavable sequence region, (8) a heavy chain leader region, (9) an antibody heavy chain variable region, and (10) an antibody heavy chain constant region.

The present disclosure provides a vector operably linked to a nucleic acid that encodes a first polypeptide chain comprising five regions ordered from the amino terminus to the carboxyl terminus: (i) a CD38 antibody heavy chain variable region comprising the amino acid sequence of SEQ ID NO:1, (ii) a CD38 antibody heavy chain constant region comprising the amino acid sequence of SEQ ID NO:2, (iii) a CD28 hinge region comprising the amino acid sequence of SEQ ID NO:5, (iv) a CD28 transmembrane region comprising the amino acid sequence of SEQ ID NO:6, and (v) an intracellular signaling region comprising a 4-1BB intracellular signaling sequence comprising the amino acid sequence of SEQ ID NO:7 and a CD3zeta intracellular signaling sequence comprising the amino acid sequence of SEQ ID NO:9.

The present disclosure provides a vector operably linked to a nucleic acid that encodes a second polypeptide chain comprising two regions ordered from the amino terminus to the carboxyl terminus: (i) a CD38 antibody light chain variable region comprising the amino acid sequence of SEQ ID NO:3, and (ii) a CD38 antibody light chain constant region comprising the amino acid sequence of SEQ ID NO:4.

In one embodiment, the vector is operably linked to a nucleic acid that encodes the first polypeptide chain (SEQ ID NO: 13 or 16) and the second polypeptide chain (SEQ ID NO:14 or 17).

In one embodiment, the vector is operably linked to a nucleic acid that encodes the first polypeptide chain (SEQ ID NO:13 or 16), a T2A cleavage sequence (SEQ ID NO:12), and the second polypeptide chain (SEQ ID NO:14 or 17). In one embodiment, the first polypeptide chain (SEQ ID NO:13 or 16) includes or lacks the leader sequence underlined in FIGS. 35B and C. In one embodiment, the second polypeptide chain (SEQ ID NO:14 or 17) includes or lacks the leader sequence underlined in FIGS. 35B and C. The present disclosure provides a vector operably linked to a nucleic acid that encodes a precursor polypeptide, comprising the amino acid sequence of SEQ ID NO: 15 or 18.

The present disclosure provides vectors operably linked to nucleic acids that encode a Version 1 (e.g., V1) dimeric antigen receptors (DAR) construct comprising a first polypeptide chain carrying heavy chain variable (VH) and heavy chain constant regions (CH), and a second polypeptide chain carrying light chain variable (VL) and light chain constant regions (CL) (e.g., FIG. 1), wherein (a) a first vector is operably linked to a first nucleic acid that encodes the first polypeptide chain comprising five regions ordered from the amino terminus to the carboxyl terminus: (i) an antibody heavy chain variable region (VH), (ii) an antibody heavy chain constant region (CH), (iii) a long hinge region comprising CD8 and CD28 hinge sequences (e.g., SEQ ID NO: 19), (iv) a transmembrane region (TM) comprising CD28 transmembrane sequence (e.g., SEQ ID NO:6), and (v) an intracellular signaling region comprising CD28 signaling sequence (e.g., SEQ ID NO:8) and CD3-zeta signaling sequence having ITAM motifs 1, 2 and 3 (e.g., SEQ ID NO:9); (b) the first vector is operably linked to the second nucleic acid that encodes a second polypeptide chain comprising two regions ordered from the amino terminus to the carboxyl terminus: (i) an antibody light chain variable region (VL) (e.g., kappa or lambda), and (ii) an antibody light chain constant region (CL). In one embodiment, the antibody heavy chain variable region (VH) comprises an anti-CD38 heavy chain variable region sequence (e.g., SEQ ID NO: 1) and the antibody heavy chain constant region (CH) comprises an anti-CD38 heavy chain constant region sequence (e.g., SEQ ID NO:2).

The present disclosure provides vectors operably linked to nucleic acids that encode a Version 2 (e.g., V2) dimeric antigen receptors (DAR) construct comprising a first polypeptide chain carrying heavy chain variable (VH) and heavy chain constant regions (CH), and a second polypeptide chain carrying light chain variable (VL) and light chain constant regions (CL) (e.g., FIGS. 1 and 2), wherein (a) a first vector operably linked to a first nucleic acid that encodes the first polypeptide chain comprising five regions ordered from the amino terminus to the carboxyl terminus: (i) an antibody heavy chain variable region (VH), (ii) an antibody heavy chain constant region (CH), (iii) a short hinge region comprising a CD28 hinge sequence (e.g., SEQ ID NO:5), (iv) a transmembrane region (TM) comprising CD28 transmembrane sequence (e.g., SEQ ID NO: 6), and (v) an intracellular signaling region comprising either (1) a 4-1BB signaling sequence (e.g., SEQ ID NO:7) and CD3-zeta having ITAM motifs 1, 2 and 3 (e.g., SEQ ID NO: 9), or (2) CD28 (e.g., SEQ ID NO:8) signaling sequence and CD3-zeta having ITAM motifs 1, 2 and 3 (e.g., SEQ ID NO:9), or (3) 4-1BB (e.g., SEQ ID NO:7) signaling sequence and CD28 (e.g., SEQ ID NO:8) signaling sequence and CD3-zeta having ITAM motifs 1, 2 and 3 (e.g., SEQ ID NO:9); (b) the first vector is operably linked to a second nucleic acid that encodes the second polypeptide chain comprising two regions ordered from the amino terminus to the carboxyl terminus: (i) an antibody light chain variable region (VL) (e.g., kappa or lambda), and (ii) an antibody light chain constant region (CL).

In one embodiment, the vector is operably linked to a nucleic acid encoding the Version 2a (V2a) DAR construct comprising the intracellular signaling region having the 4-1BB signaling sequence (e.g., SEQ ID NO:7) and CD3-zeta having ITAM motifs 1, 2 and 3 (e.g., SEQ ID NO:9).

In one embodiment, the vector is operably linked to a nucleic acid encoding the Version 2b (V2b) DAR construct comprising the intracellular signaling region having the CD28 (e.g., SEQ ID NO:8) signaling sequence and CD3-zeta having ITAM motifs 1, 2 and 3 (e.g., SEQ ID NO:9).

In one embodiment, the vector is operably linked to a nucleic acid encoding the Version 2c (V2c) DAR construct comprising the intracellular signaling region having the 4-1BB (e.g., SEQ ID NO:7) signaling sequence and CD28 (e.g., SEQ ID NO:8) signaling sequence and CD3-zeta having ITAM motifs 1, 2 and 3 (e.g., SEQ ID NO:9). In one embodiment, the DAR V2a and V2b are second generation DAR constructs, while the DAR V2c is a third generation DAR construct. In one embodiment, the antibody heavy chain variable region (VH) comprises an anti-CD38 heavy chain variable region sequence (e.g., SEQ ID NO:1) and the antibody heavy chain constant region (CH) comprises an anti-CD38 heavy chain constant region sequence (e.g., SEQ ID NO:2).

The present disclosure provides vectors operably linked to nucleic acids that encode a Version 3 (e.g., V3) dimeric antigen receptors (DAR) construct comprising a first polypeptide chain carrying heavy chain variable (VH) and heavy chain constant regions (CH), and a second polypeptide chain carrying light chain variable (VL) and light chain constant regions (CL) (e.g., FIG. 1), wherein (a) a first vector operably linked to a first nucleic acid that encodes the first polypeptide chain comprising five regions ordered from the amino terminus to the carboxyl terminus: (i) an antibody heavy chain variable region (VH), (ii) an antibody heavy chain constant region (CH), (iii) a short hinge region comprising CD28 hinge sequences (e.g., SEQ ID NO:5), (iv) a transmembrane region (TM) comprising CD28 transmembrane sequence (e.g., SEQ ID NO: 6), and (v) an intracellular signaling region comprising 4-1BB signaling sequence (e.g., SEQ ID NO: 7) and CD3-zeta signaling sequence having only ITAM motif 3 (e.g., SEQ ID NO:20); (b) the first vector operably is linked to a second nucleic acid that encodes the second polypeptide chain comprising two regions ordered from the amino terminus to the carboxyl terminus: (i) an antibody light chain variable region (VL) (e.g., kappa or lambda), and (ii) an antibody light chain constant region (CL). In one embodiment, the antibody heavy chain variable region (VH) comprises an anti-CD38 heavy chain variable region sequence (e.g., SEQ ID NO: 1) and the antibody heavy chain constant region (CH) comprises an anti-CD38 heavy chain constant region sequence (e.g., SEQ ID NO:2).

The present disclosure provides vectors operably linked to nucleic acids that encode a Version 4 (e.g., V4) dimeric antigen receptors (DAR) construct comprising a first polypeptide chain carrying heavy chain variable (VH) and heavy chain constant regions (CH), and a second polypeptide chain carrying light chain variable (VL) and light chain constant regions (CL), wherein (a) a first vector operably linked to a first nucleic acid that encodes the first polypeptide chain comprising four regions ordered from the amino terminus to the carboxyl terminus: (i) an antibody heavy chain variable region (VH), (ii) an antibody heavy chain constant region (CH), (iii) a transmembrane region (TM) comprising CD28 transmembrane sequence (e.g., SEQ ID NO: 6), and (iv) an intracellular signaling region comprising 4-1BB signaling sequence (e.g., SEQ ID NO:7) and CD3-zeta signaling sequence having only ITAM motif 3 (e.g., SEQ ID NO: 20); (b) the first vector is operably linked to a second nucleic acid that encodes the second polypeptide chain comprising two regions ordered from the amino terminus to the carboxyl terminus: (i) an antibody light chain variable region (VL) (e.g., kappa or lambda), and (ii) an antibody light chain constant region (CL). The DAR V4 construct lacks a hinge sequence. In one embodiment, the antibody heavy chain variable region (VH) comprises an anti-CD38 heavy chain variable region sequence (e.g., SEQ ID NO:1) and the antibody heavy chain constant region (CH) comprises an anti-CD38 heavy chain constant region sequence (e.g., SEQ ID NO:2).

The present disclosure provides a host cell, or a population of host cells, which harbors one or more expression vectors operably linked to a nucleic acid transgene that encodes any of the first polypeptide chains, second polypeptide chains, first and second polypeptide chains, dimeric antigen receptors or precursor polypeptides described herein.

In one embodiment, the host cell or population of host cells are introduced with one or more expression vectors, where the vectors are operably linked to a nucleic acid transgene encoding any of the dimeric antigen receptor (DAR) constructs described herein. The host cell or the population of host cells comprise T lymphocytes (e.g., T cells, regulatory T cells, gamma-delta T cells, and cytotoxic T cells), NK (natural killer) cells, macrophages, dendritic cells, mast cells, eosinophils, B lymphocytes, monocytes. In one embodiment, the NK cells comprise cord blood-derived NK cells, or placental derived NK cells.

In one embodiment, the host cell or population of host cells harbor one or more expression vectors that can direct transient introduction of the transgene into the host cells or stable insertion of the transgene into the host cells' genome. The expression vector(s) can direct transcription and/or translation of the transgene in the host cell. The expression vector can include nucleic acid backbone sequences derived from a retrovirus, lentivirus or adenovirus. The expression vectors can include one or more regulatory sequences, such as inducible and/or constitutive promoters and enhancers. The expression vectors can include ribosomal binding sites and/or polyadenylation sites.

In one embodiment, the expression vector, which is operably linked to the nucleic acid encoding the dimeric antigen receptor (DAR) construct, can direct production of the dimeric antigen receptor (DAR) construct which can be displayed on the surface of the transgenic host cell or the dimeric antigen receptor can be secreted into the cell culture medium.

In one embodiment, host cells can harbor one or more expression vectors operably linked to the nucleic acid transgene that encodes any of the dimeric antigen receptors, and the host cells can be cultured in an appropriate culture medium to transiently or stably express a dimeric antigen receptor construct.

The present disclosure provides a host cell, or a population of host cells, which harbors an expression vector operably linked to a nucleic acid that encodes a first polypeptide chain comprising: five regions ordered from the amino terminus to the carboxyl terminus: (i) an antibody heavy chain variable region, (ii) an antibody heavy chain constant region, (iii) an optional hinge region, (iv) a transmembrane region, and (v) an intracellular signaling region.

The present disclosure provides host cell, or a population of host cells, which harbors an expression vector operably linked to a nucleic acid that encodes a second polypeptide chain comprising: two regions ordered from the amino terminus to the carboxyl terminus: (i) an antibody light chain variable region, and (ii) an antibody light chain constant region.

In one embodiment, the host cell, or the population of host cells, harbors a first expression vector operably linked to a nucleic acid that encodes the first polypeptide chain and harbors a second expression vector operably linked to a nucleic acid that encodes the second polypeptide chain, wherein (a) the first polypeptide chain comprises five regions ordered from the amino terminus to the carboxyl terminus: (i) an antibody heavy chain variable region, (ii) an antibody heavy chain constant region, (iii) an optional hinge region, (iv) a transmembrane region, and (v) an intracellular signaling region having two to five intracellular signaling sequences; and wherein (b) the second polypeptide chain comprising: two regions ordered from the amino terminus to the carboxyl terminus: (i) an antibody light chain variable region, and (ii) an antibody light chain constant region.

In one embodiment, the host cell, or the population of host cells, harbors an expression vector operably linked to a nucleic acid that encodes the first and second polypeptide chains, comprising: (a) a first polypeptide chain comprising five regions ordered from the amino terminus to the carboxyl terminus: (i) an antibody heavy chain variable region, (ii) an antibody heavy chain constant region, (iii) an optional hinge region, (iv) a transmembrane region, and (v) an intracellular signaling region having two to five intracellular signaling sequences; and (b) a second polypeptide chain comprising: two regions ordered from the amino terminus to the carboxyl terminus: (i) an antibody light chain variable region, and (ii) an antibody light chain constant region.

In one embodiment, the host cell, or population of host cells, expresses the first and second polypeptide chains.

The present disclosure provides host cell, or a population of host cells, which harbors an expression vector operably linked to a nucleic acid that encodes a first polypeptide chain comprising: five regions ordered from the amino terminus to the carboxyl terminus: (i) an antibody light chain variable region, (ii) an antibody light chain constant region, (iii) an optional hinge region, (iv) a transmembrane region, and (v) an intracellular signaling region.

The present disclosure provides host cell, or a population of host cells, which harbors an expression vector operably linked to a nucleic acid that encodes a second polypeptide chain comprising: two regions ordered from the amino terminus to the carboxyl terminus: (i) an antibody heavy chain variable region, and (ii) an antibody heavy chain constant region.

In one embodiment, the host cell, or the population of host cells, harbors a first expression vector operably linked to a nucleic acid that encodes the first polypeptide chain and harbors a second expression vector operably linked to a nucleic acid that encodes the second polypeptide chain, wherein (a) the first polypeptide chain comprises five regions ordered from the amino terminus to the carboxyl terminus: (i) an antibody light chain variable region, (ii) an antibody light chain constant region, (iii) an optional hinge region, (iv) a transmembrane region, and (v) an intracellular signaling region having two to five intracellular signaling sequences; and wherein (b) the second polypeptide chain comprising: two regions ordered from the amino terminus to the carboxyl terminus: (i) an antibody heavy chain variable region, and (ii) an antibody heavy chain constant region.

In one embodiment, the host cell, or the population of host cells, harbors an expression vector operably linked to a nucleic acid that encodes the first and second polypeptide chains, comprising: (a) a first polypeptide chain comprising five regions ordered from the amino terminus to the carboxyl terminus: (i) an antibody light chain variable region, (ii) an antibody light chain constant region, (iii) an optional hinge region, (iv) a transmembrane region, and (v) an intracellular signaling region having two to five intracellular signaling sequences; and (b) a second polypeptide chain comprising: two regions ordered from the amino terminus to the carboxyl terminus: (i) an antibody heavy chain variable region, and (ii) an antibody heavy chain constant region.

In one embodiment, the host cell, or population of host cells, expresses the first and second polypeptide chains.

The present disclosure provides a host cell, or a population of host cells, which harbors an expression vector operably linked to a nucleic acid that encodes a first polypeptide chain comprising: six regions ordered from the amino terminus to the carboxyl terminus: (i) a heavy chain leader region, (ii) an antibody heavy chain variable region, (iii) an antibody heavy chain constant region, (iv) an optional hinge region, (v) a transmembrane region, and (vi) an intracellular signaling region.

The present disclosure provides a host cell, or a population of host cells, which harbors an expression vector operably linked to a nucleic acid that encodes a second polypeptide chain comprising: three regions ordered from the amino terminus to the carboxyl terminus: (i) a light chain leader region, (ii) an antibody light chain variable region, and (iii) an antibody light chain constant region.

In one embodiment, the host cell, or the population of host cells, harbors a first expression vector operably linked to a nucleic acid that encodes the first polypeptide chain and harbors a second expression vector operably linked to a nucleic acid that encodes the second polypeptide chain, wherein (a) the first polypeptide chain comprising six regions ordered from the amino terminus to the carboxyl terminus: (i) a heavy chain leader sequence, (ii) an antibody heavy chain variable region, (iii) an antibody heavy chain constant region, (iv) an optional hinge region, (v) a transmembrane region, and (vi) an intracellular signaling region having two to five intracellular signaling sequences; and wherein (b) the second polypeptide chain comprising: two regions ordered from the amino terminus to the carboxyl terminus: (i) an antibody light chain variable region, and (ii) an antibody light chain constant region.

In one embodiment, the host cell, or the population of host cells, harbors an expression vector operably linked to a nucleic acid that encodes the first and second polypeptide chains, comprising: (a) a first polypeptide chain comprising six regions ordered from the amino terminus to the carboxyl terminus: (i) a heavy chain leader sequence, (ii) an antibody heavy chain variable region, (iii) an antibody heavy chain constant region, (iv) an optional hinge region, (v) a transmembrane region, and (vi) an intracellular signaling region having two to five intracellular signaling sequences; and (b) a second polypeptide chain comprising: two regions ordered from the amino terminus to the carboxyl terminus: (i) an antibody light chain variable region, and (ii) an antibody light chain constant region.

In one embodiment, the host cell, or population of host cells, expresses the first and second polypeptide chains.

The present disclosure provides a host cell, or a population of host cells, which harbors an expression vector operably linked to a nucleic acid that encodes a first polypeptide chain comprising: six regions ordered from the amino terminus to the carboxyl terminus: (i) a light chain leader region, (ii) an antibody light chain variable region, (iii) an antibody light chain constant region, (iv) an optional hinge region, (v) a transmembrane region, and (vi) an intracellular signaling region.

The present disclosure provides a host cell, or a population of host cells, which harbors an expression vector operably linked to a nucleic acid that encodes a second polypeptide chain comprising: three regions ordered from the amino terminus to the carboxyl terminus: (i) a heavy chain leader region, (ii) an antibody heavy chain variable region, and (iii) an antibody light chain constant region.

In one embodiment, the host cell, or the population of host cells, harbors a first expression vector operably linked to a nucleic acid that encodes the first polypeptide chain and harbors a second expression vector operably linked to a nucleic acid that encodes the second polypeptide chain, wherein (a) the first polypeptide chain comprising six regions ordered from the amino terminus to the carboxyl terminus: (i) a light chain leader sequence, (ii) an antibody light chain variable region, (iii) an antibody light chain constant region, (iv) an optional hinge region, (v) a transmembrane region, and (vi) an intracellular signaling region having two to five intracellular signaling sequences; and wherein (b) the second polypeptide chain comprising: two regions ordered from the amino terminus to the carboxyl terminus: (i) an antibody heavy chain variable region, and (ii) an antibody heavy chain constant region.

In one embodiment, the host cell, or the population of host cells, harbors an expression vector operably linked to a nucleic acid that encodes the first and second polypeptide chains, comprising: (a) a first polypeptide chain comprising six regions ordered from the amino terminus to the carboxyl terminus: (i) a light chain leader sequence, (ii) an antibody light chain variable region, (iii) an antibody light chain constant region, (iv) an optional hinge region, (v) a transmembrane region, and (vi) an intracellular signaling region having two to five intracellular signaling sequences; and (b) a second polypeptide chain comprising: two regions ordered from the amino terminus to the carboxyl terminus: (i) an antibody heavy chain variable region, and (ii) an antibody heavy chain constant region.

In one embodiment, the host cell, or population of host cells, expresses the first and second polypeptide chains.

The present disclosure provides a host cell, or a population of host cells, which harbors an expression vector operably linked to a nucleic acid that encodes a precursor polypeptide comprising: ten regions ordered from the amino terminus to the carboxyl terminus: (1) a heavy chain leader region, (2) an antibody heavy chain variable region, (3) an antibody heavy chain constant region, (4) an optional hinge region, (5) a transmembrane region, (6) an intracellular signaling region having two to five intracellular signaling sequences, (7) T2A cleavable sequence region, (8) a light chain leader region, (9) an antibody light chain variable region, and (10) an antibody light chain constant region.

In one embodiment, the host cell, or population of host cells, expresses the precursor polypeptide.

The present disclosure provides a host cell, or a population of host cells, which harbors an expression vector operably linked to a nucleic acid that encodes a precursor polypeptide comprising: ten regions ordered from the amino terminus to the carboxyl terminus: (1) a light chain leader region, (2) an antibody light chain variable region, (3) an antibody light chain constant region, (4) an optional hinge region, (5) a transmembrane region, (6) an intracellular signaling region having two to five intracellular signaling sequences, (7) T2A cleavable sequence region, (8) a heavy chain leader region, (9) an antibody heavy chain variable region, and (10) an antibody heavy chain constant region.

In one embodiment, the host cell, or population of host cells, expresses the precursor polypeptide.

The present disclosure provides a host cell, or a population of host cells, which harbors an expression vector operably linked to a nucleic acid that encodes a first polypeptide chain comprising five regions ordered from the amino terminus to the carboxyl terminus: (i) a CD38 antibody heavy chain variable region comprising the amino acid sequence of SEQ ID NO: 1, (ii) a CD38 antibody heavy chain constant region comprising the amino acid sequence of SEQ ID NO:2, (iii) a CD28 hinge region comprising the amino acid sequence of SEQ ID NO:5, (iv) a CD28 transmembrane region comprising the amino acid sequence of SEQ ID NO:6, and (v) an intracellular signaling region comprising a 4-1BB intracellular signaling sequence comprising the amino acid sequence of SEQ ID NO:7 and a CD3zeta intracellular signaling sequence comprising the amino acid sequence of SEQ ID NO:9.

The present disclosure provides a host cell, or a population of host cells, which harbors an expression vector operably linked to a nucleic acid that encodes a second polypeptide chain comprising two regions ordered from the amino terminus to the carboxyl terminus: (i) a CD38 antibody light chain variable region comprising the amino acid sequence of SEQ ID NO:3, and (ii) a CD38 antibody light chain constant region comprising the amino acid sequence of SEQ ID NO: 4.

In one embodiment, the vector is operably linked to a nucleic acid that encodes the first and second polypeptide chains (SEQ ID NOS: 6 and 7).

In one embodiment, the vector is operably linked to a nucleic acid that encodes the first polypeptide chain (SEQ ID NO:6), a T2A cleavage sequence (SEQ ID NO: 12), and the second polypeptide chain (SEQ ID NO:7).

The present disclosure provides a vector operably linked to a nucleic acid that encodes a precursor polypeptide, comprising the amino acid sequence of SEQ ID NO:15.

In one embodiment, the host cell expresses the first polypeptide chain (SEQ ID NO: 13 or 16) and the second polypeptide chain (SEQ ID NOS: 14 or 17). In one embodiment, the host cell expresses the precursor polypeptide of SEQ ID NO: 15 or 18).

In one embodiment, the first polypeptide chain (SEQ ID NO: 13 or 16) includes or lacks the leader sequence underlined in FIG. 35B or C. In one embodiment, the second polypeptide chain (SEQ ID NO:14 or 17) includes or lacks the leader sequence underlined in FIG. 35B or C.

The present disclosure provides a host cell, or a population of host cells, which harbors an expression vector operably linked to a nucleic acid that encodes a Version 1 (e.g., V1) dimeric antigen receptors (DAR) construct comprising a first polypeptide chain carrying heavy chain variable (VH) and heavy chain constant regions (CH), and a second polypeptide chain carrying light chain variable (VL) and light chain constant regions (CL) (e.g., FIG. 1), wherein the host cell, or a population of host cells harbor (a) a first vector is operably linked to a first nucleic acid that encodes the first polypeptide chain comprising five regions ordered from the amino terminus to the carboxyl terminus: (i) an antibody heavy chain variable region (VH), (ii) an antibody heavy chain constant region (CH), (iii) a long hinge region comprising CD8 and CD28 hinge sequences (e.g., SEQ ID NO:19), (iv) a transmembrane region (TM) comprising CD28 transmembrane sequence (e.g., SEQ ID NO:6), and (v) an intracellular signaling region comprising CD28 signaling sequence (e.g., SEQ ID NO:8) and CD3-zeta signaling sequence having ITAM motifs 1, 2 and 3 (e.g., SEQ ID NO:9); (b) the first vector is operably linked to the second nucleic acid that encodes a second polypeptide chain comprising two regions ordered from the amino terminus to the carboxyl terminus: (i) an antibody light chain variable region (VL) (e.g., kappa or lambda), and (ii) an antibody light chain constant region (CL). In one embodiment, the antibody heavy chain variable region (VH) comprises an anti-CD38 heavy chain variable region sequence (e.g., SEQ ID NO:1) and the antibody heavy chain constant region (CH) comprises an anti-CD38 heavy chain constant region sequence (e.g., SEQ ID NO:2).

The present disclosure provides a the vector is operably linked to a nucleic acid encoding the a Version 2 (e.g., V2) dimeric antigen receptors (DAR) construct comprising a first polypeptide chain carrying heavy chain variable (VH) and heavy chain constant regions (CH), and a second polypeptide chain carrying light chain variable (VL) and light chain constant regions (CL) (e.g., FIGS. 1 and 2), wherein the host cell, or a population of host cells harbor (a) a first vector operably linked to a first nucleic acid that encodes the first polypeptide chain comprising five regions ordered from the amino terminus to the carboxyl terminus: (i) an antibody heavy chain variable region (VH), (ii) an antibody heavy chain constant region (CH), (iii) a short hinge region comprising a CD28 hinge sequence (e.g., SEQ ID NO:5), (iv) a transmembrane region (TM) comprising CD28 transmembrane sequence (e.g., SEQ ID NO:6), and (v) an intracellular signaling region comprising either (1) a 4-1BB signaling sequence (e.g., SEQ ID NO:7) and CD3-zeta having ITAM motifs 1, 2 and 3 (e.g., SEQ ID NO:9), or (2) CD28 (e.g., SEQ ID NO:8) signaling sequence and CD3-zeta having ITAM motifs 1, 2 and 3 (e.g., SEQ ID NO:9), or (3) 4-1BB (e.g., SEQ ID NO:7) signaling sequence and CD28 (e.g., SEQ ID NO: 8) signaling sequence and CD3-zeta having ITAM motifs 1, 2 and 3 (e.g., SEQ ID NO:9); (b) the first vector is operably linked to a second nucleic acid that encodes the second polypeptide chain comprising two regions ordered from the amino terminus to the carboxyl terminus: (i) an antibody light chain variable region (VL) (e.g., kappa or lambda), and (ii) an antibody light chain constant region (CL).

In one embodiment, the vector is operably linked to a nucleic acid encoding the Version 2a (V2a) DAR construct comprising the intracellular signaling region having the 4-1BB signaling sequence (e.g., SEQ ID NO:7) and CD3-zeta having ITAM motifs 1, 2 and 3 (e.g., SEQ ID NO:9).

In one embodiment, the vector is operably linked to a nucleic acid encoding the Version 2b (V2b) DAR construct comprising the intracellular signaling region having the CD28 (e.g., SEQ ID NO:8) signaling sequence and CD3-zeta having ITAM motifs 1, 2 and 3 (e.g., SEQ ID NO:9).

In one embodiment, the vector is operably linked to a nucleic acid encoding the Version 2c (V2c) DAR construct comprising the intracellular signaling region having the 4-1BB (e.g., SEQ ID NO:7) signaling sequence and CD28 (e.g., SEQ ID NO:8) signaling sequence and CD3-zeta having ITAM motifs 1, 2 and 3 (e.g., SEQ ID NO:9). In one embodiment, the DAR V2a and V2b are second generation DAR constructs, while the DAR V2c is a third generation DAR construct. In one embodiment, the antibody heavy chain variable region (VH) comprises an anti-CD38 heavy chain variable region sequence (e.g., SEQ ID NO:1) and the antibody heavy chain constant region (CH) comprises an anti-CD38 heavy chain constant region sequence (e.g., SEQ ID NO:2).

The present disclosure provides a host cell, or a population of host cells, which harbors an expression vector operably linked to a nucleic acid that encodes a Version 3 (e.g., V3) dimeric antigen receptors (DAR) construct comprising a first polypeptide chain carrying heavy chain variable (VH) and heavy chain constant regions (CH), and a second polypeptide chain carrying light chain variable (VL) and light chain constant regions (CL) (e.g., FIG. 1), wherein the host cell, or a population of host cells harbor (a) a first vector operably linked to a first nucleic acid that encodes the first polypeptide chain comprising five regions ordered from the amino terminus to the carboxyl terminus: (i) an antibody heavy chain variable region (VH), (ii) an antibody heavy chain constant region (CH), (iii) a short hinge region comprising CD28 hinge sequences (e.g., SEQ ID NO:5), (iv) a transmembrane region (TM) comprising CD28 transmembrane sequence (e.g., SEQ ID NO:6), and (v) an intracellular signaling region comprising 4-1BB signaling sequence (e.g., SEQ ID NO:7) and CD3-zeta signaling sequence having only ITAM motif 3 (e.g., SEQ ID NO:20); (b) the first vector operably is linked to a second nucleic acid that encodes the second polypeptide chain comprising two regions ordered from the amino terminus to the carboxyl terminus: (i) an antibody light chain variable region (VL) (e.g., kappa or lambda), and (ii) an antibody light chain constant region (CL). In one embodiment, the antibody heavy chain variable region (VH) comprises an anti-CD38 heavy chain variable region sequence (e.g., SEQ ID NO:1) and the antibody heavy chain constant region (CH) comprises an anti-CD38 heavy chain constant region sequence (e.g., SEQ ID NO:2).

The present disclosure provides a host cell, or a population of host cells, which harbors an expression vector operably linked to a nucleic acid that encodes a Version 4 (e.g., V4) dimeric antigen receptors (DAR) construct comprising a first polypeptide chain carrying heavy chain variable (VH) and heavy chain constant regions (CH), and a second polypeptide chain carrying light chain variable (VL) and light chain constant regions (CL), wherein the host cell, or a population of host cells harbor (a) a first vector operably linked to a first nucleic acid that encodes the first polypeptide chain comprising four regions ordered from the amino terminus to the carboxyl terminus: (i) an antibody heavy chain variable region (VH), (ii) an antibody heavy chain constant region (CH), (iii) a transmembrane region (TM) comprising CD28 transmembrane sequence (e.g., SEQ ID NO:6), and (iv) an intracellular signaling region comprising 4-1BB signaling sequence (e.g., SEQ ID NO:7) and CD3-zeta signaling sequence having only ITAM motif 3 (e.g., SEQ ID NO:20); (b) the first vector is operably linked to a second nucleic acid that encodes the second polypeptide chain comprising two regions ordered from the amino terminus to the carboxyl terminus: (i) an antibody light chain variable region (VL) (e.g., kappa or lambda), and (ii) an antibody light chain constant region (CL). The DAR V4 construct lacks a hinge sequence. In one embodiment, the antibody heavy chain variable region (VH) comprises an anti-CD38 heavy chain variable region sequence (e.g., SEQ ID NO:1) and the antibody heavy chain constant region (CH) comprises an anti-CD38 heavy chain constant region sequence (e.g., SEQ ID NO: 2).

The present disclosure further provides methods for conducting adoptive cell therapy by administering to a subject transgenic host cells that have been engineered to express the dimeric antigen receptor constructs.

The present disclosure further provides a method of treating a subject having a disease, disorder or condition associated with detrimental expression (e.g., elevated expression) of a tumor antigen. Such a method includes, for example, administering to a subject a host cell harboring an expression vector operably linked to a nucleic acid that encodes any of the first polypeptide chains or second polypeptide chains, or any of the first and second polypeptide chains, or any of the precursor polypeptide chains described herein. In one embodiment, the host cell or the population of host cells express any of the first and second polypeptide chains, or any of the precursor polypeptide chains described herein.

In one embodiment, the host cell or population of host cells used to treat a subject are introduced with one or more expression vectors, where the vectors are operably linked to a nucleic acid transgene encoding any of the dimeric antigen receptor (DAR) constructs described herein. The host cell or the population of host cells comprise T lymphocytes (e.g., T cells, regulatory T cells, gamma-delta T cells, and cytotoxic T cells), NK (natural killer) cells, macrophages, dendritic cells, mast cells, eosinophils, B lymphocytes, monocytes. In one embodiment, the NK cells comprise cord blood-derived NK cells, or placental derived NK cells.

In one embodiment, the host cell or population of host cells that are used to treat a subject harbor one or more expression vectors that can direct transient introduction of the transgene into the host cells or stable insertion of the transgene into the host cells' genome. The expression vector(s) can direct transcription and/or translation of the transgene in the host cell. In one embodiment, the transgene comprises a nucleic acid that encodes any of the first polypeptide chains or second polypeptide chains, or any of the first and second polypeptide chains, or any of the precursor polypeptide chains described herein. The expression vector can include nucleic acid backbone sequences derived from a retrovirus, lentivirus or adenovirus. The expression vectors can include one or more regulatory sequences, such as inducible and/or constitutive promoters and enhancers. The expression vectors can include ribosomal binding sites and/or polyadenylation sites.

In one embodiment, the expression vector, which is operably linked to the nucleic acid encoding the dimeric antigen receptor (DAR) construct, can direct production of the dimeric antigen receptor (DAR) construct which can be displayed on the surface of the transgenic host cell or the dimeric antigen receptor can be secreted into the cell culture medium.

In one embodiment, host cells can harbor one or more expression vectors operably linked to the nucleic acid transgene that encodes any of the dimeric antigen receptors, and the host cell can be cultured in an appropriate culture medium to transiently or stably express a dimeric antigen receptor construct.

In one embodiment, the host cell or population of host cells used to treat the subject are autologous and are derived from the subject receiving the treatment. In one embodiment, whole blood can be obtained from the subject and the desired cells (e.g., T lymphocytes, NK cells or macrophages) can be recovered from the whole blood.

In one embodiment, the host cell or population of host cells used to treat the subject are allogenic and are derived from a different subject. Allogenic cells can be obtained from whole blood from a different subject in the same manner employed for the autologous cells. In one embodiment, the allogenic cells are derived from placenta or chord tissue after pregnancy.

In one embodiment, the desired cells are obtained from the subject to receive treatment, or from a different subject, and are engineered to harbor one or more expression vectors that direct expression of any of the first or second polypeptides, or the precursor polypeptides, thereby generating transgenic host cells. The transgenic host cells can express the first or second polypeptides, or the precursor polypeptide. The host cells can express the first and second polypeptide chains which dimerize to form a dimeric antigen receptor that binds specifically to the tumor antigen in the subject. The host cells can express the precursor polypeptide chain which can be cleaved to form first and second polypeptide chains that dimerize to form a dimeric antigen receptor that binds specifically to the tumor antigen in the subject. The transgenic host cells (e.g., harboring the expression vector(s) or expressing the polypeptide chains) can be administered to the subject to treat the disease, disorder or condition associated with detrimental expression of a tumor antigen.

The present disclosure provides a method of treating a subject having a disease, disorder or condition associated with detrimental expression of a tumor antigen, wherein the disorder is cancer, including, but not limited to hematologic breast cancer, ovarian cancer, prostate cancer, head and neck cancer, lung cancer, bladder cancer, melanoma, colorectal cancer, pancreatic cancer, lung cancer, liver cancer, renal cancer, esophageal cancer, leiomyoma, leiomyosarcoma, glioma, and glioblastoma.

In one embodiment, the cancer is a hematologic cancer selected from the group consisting of non-Hodgkin's lymphoma (NHL), Burkitt's lymphoma (BL), B chronic lymphocytic leukemia (B-CLL), B and T acute lymphocytic leukemia (ALL), T cell lymphoma (TCL), acute myeloid leukemia (AML), hairy cell leukemia (HCL), Hodgkin's Lymphoma (HL), chronic myeloid leukemia (CML) and multiple myeloma (MM).

The present disclosure further provides a method for treating a subject having a disease, disorder or condition associated with detrimental expression of a tumor antigen, comprises: administering to the subject a host cell, or a population of host cells, which harbors an expression vector operably linked to a nucleic acid that encodes a first polypeptide chain comprising: five regions ordered from the amino terminus to the carboxyl terminus: (i) an antibody heavy chain variable region, (ii) an antibody heavy chain constant region, (iii) an optional hinge region, (iv) a transmembrane region, and (v) an intracellular signaling region (e.g., FIGS. 1 and 2).

The present disclosure further provides a method for treating a subject having a disease, disorder or condition associated with detrimental expression of a tumor antigen, comprises: administering to the subject a host cell, or a population of host cells, which harbors an expression vector operably linked to a nucleic acid that encodes a second polypeptide chain comprising: two regions ordered from the amino terminus to the carboxyl terminus: (i) an antibody light chain variable region, and (ii) an antibody light chain constant region (e.g., FIGS. 1 and 2).

The present disclosure further provides a method for treating a subject having a disease, disorder or condition associated with detrimental expression of a tumor antigen, comprises: administering to the subject a host cell, or a population of host cells, which harbors a first and second expression vector, wherein the first expression vector is operably linked to a nucleic acid that encodes the first polypeptide chain and the second expression vector is operably linked to a nucleic acid that encodes the second polypeptide chain, wherein (a) the first polypeptide chain comprises five regions ordered from the amino terminus to the carboxyl terminus: (i) an antibody heavy chain variable region, (ii) an antibody heavy chain constant region, (iii) an optional hinge region, (iv) a transmembrane region, and (v) an intracellular signaling region having two to five intracellular signaling sequences; and wherein (b) the second polypeptide chain comprising: two regions ordered from the amino terminus to the carboxyl terminus: (i) an antibody light chain variable region, and (ii) an antibody light chain constant region (e.g., FIGS. 1 and 2).

The present disclosure further provides a method for treating a subject having a disease, disorder or condition associated with detrimental expression of a tumor antigen, comprises: administering to the subject a host cell, or a population of host cells, which harbors an expression vector operably linked to a nucleic acid that encodes the first and second polypeptide chains, comprising: (a) a first polypeptide chain comprising five regions ordered from the amino terminus to the carboxyl terminus: (i) an antibody heavy chain variable region, (ii) an antibody heavy chain constant region, (iii) an optional hinge region, (iv) a transmembrane region, and (v) an intracellular signaling region having two to five intracellular signaling sequences; and (b) a second polypeptide chain comprising: two regions ordered from the amino terminus to the carboxyl terminus: (i) an antibody light chain variable region, and (ii) an antibody light chain constant region (e.g., FIGS. 1 and 2).

In one embodiment, a method for treating a subject having a disease, disorder or condition associated with detrimental expression of a tumor antigen, comprises: administering to the subject a host cell, or a population of host cells, which expresses the first polypeptide chains, the second polypeptide chains, or the first and second polypeptide chains (e.g., FIGS. 1 and 2). In one embodiment, the first and second polypeptide chains dimerize to form a dimeric antigen receptor that binds specifically to the tumor antigen in the subject.

The present disclosure further provides a method for treating a subject having a disease, disorder or condition associated with detrimental expression of a tumor antigen, comprises: administering to the subject a host cell, or a population of host cells, which harbors an expression vector operably linked to a nucleic acid that encodes a first polypeptide chain comprising: five regions ordered from the amino terminus to the carboxyl terminus: (i) an antibody light chain variable region, (ii) an antibody light chain constant region, (iii) an optional hinge region, (iv) a transmembrane region, and (v) an intracellular signaling region (e.g., FIGS. 3 and 4).

The present disclosure further provides a method for treating a subject having a disease, disorder or condition associated with detrimental expression of a tumor antigen, comprises: administering to the subject a host cell, or a population of host cells, which harbors an expression vector operably linked to a nucleic acid that encodes a second polypeptide chain comprising: two regions ordered from the amino terminus to the carboxyl terminus: (i) an antibody heavy chain variable region, and (ii) an antibody heavy chain constant region (e.g., FIGS. 3 and 4).

The present disclosure further provides a method for treating a subject having a disease, disorder or condition associated with detrimental expression of a tumor antigen, comprises: administering to the subject a host cell, or a population of host cells, which harbors a first and second expression vector, wherein the first expression vector is operably linked to a nucleic acid that encodes the first polypeptide chain and the second expression vector is operably linked to a nucleic acid that encodes the second polypeptide chain, wherein (a) the first polypeptide chain comprises five regions ordered from the amino terminus to the carboxyl terminus: (i) an antibody light chain variable region, (ii) an antibody light chain constant region, (iii) an optional hinge region, (iv) a transmembrane region, and (v) an intracellular signaling region having two to five intracellular signaling sequences; and wherein (b) the second polypeptide chain comprising: two regions ordered from the amino terminus to the carboxyl terminus: (i) an antibody heavy chain variable region, and (ii) an antibody heavy chain constant region (e.g., FIGS. 3 and 4).

The present disclosure further provides a method for treating a subject having a disease, disorder or condition associated with detrimental expression of a tumor antigen, comprises: administering to the subject a host cell, or a population of host cells, which harbors an expression vector operably linked to a nucleic acid that encodes the first and second polypeptide chains, comprising: (a) a first polypeptide chain comprising five regions ordered from the amino terminus to the carboxyl terminus: (i) an antibody light chain variable region, (ii) an antibody light chain constant region, (iii) an optional hinge region, (iv) a transmembrane region, and (v) an intracellular signaling region having two to five intracellular signaling sequences; and (b) a second polypeptide chain comprising: two regions ordered from the amino terminus to the carboxyl terminus: (i) an antibody heavy chain variable region, and (ii) an antibody heavy chain constant region (e.g., FIGS. 3 and 4).

In one embodiment, a method for treating a subject having a disease, disorder or condition associated with detrimental expression of a tumor antigen, comprises: administering to the subject a host cell, or a population of host cells, which expresses the first polypeptide chains, the second polypeptide chains, or the first and second polypeptide chains (e.g., FIGS. 3 and 4). In one embodiment, the first and second polypeptide chains dimerize to form a dimeric antigen receptor that binds specifically to the tumor antigen in the subject.

The present disclosure further provides a method for treating a subject having a disease, disorder or condition associated with detrimental expression of a tumor antigen, comprises: administering to the subject a host cell, or a population of host cells, which harbors an expression vector operably linked to a nucleic acid that encodes a first polypeptide chain comprising: six regions ordered from the amino terminus to the carboxyl terminus: (i) a heavy chain leader region, (ii) an antibody heavy chain variable region, (iii) an antibody heavy chain constant region, (iv) an optional hinge region, (v) a transmembrane region, and (vi) an intracellular signaling region (e.g., FIGS. 1 and 2).

The present disclosure further provides a method for treating a subject having a disease, disorder or condition associated with detrimental expression of a tumor antigen, comprises: administering to the subject a host cell, or a population of host cells, which harbors an expression vector operably linked to a nucleic acid that encodes a second polypeptide chain comprising: three regions ordered from the amino terminus to the carboxyl terminus: (i) a light chain leader region, (ii) an antibody light chain variable region, and (iii) an antibody light chain constant region (e.g., FIGS. 1 and 2).

The present disclosure further provides a method for treating a subject having a disease, disorder or condition associated with detrimental expression of a tumor antigen, comprises: administering to the subject a host cell, or a population of host cells, which harbors a first and second expression vector, wherein the first expression vector is operably linked to a nucleic acid that encodes the first polypeptide chain and the second expression vector is operably linked to a nucleic acid that encodes the second polypeptide chain, wherein (a) the first polypeptide chain comprising six regions ordered from the amino terminus to the carboxyl terminus: (i) a heavy chain leader sequence, (ii) an antibody heavy chain variable region, (iii) an antibody heavy chain constant region, (iv) an optional hinge region, (v) a transmembrane region, and (vi) an intracellular signaling region having two to five intracellular signaling sequences; and wherein (b) the second polypeptide chain comprising: two regions ordered from the amino terminus to the carboxyl terminus: (i) an antibody light chain variable region, and (ii) an antibody light chain constant region (e.g., FIGS. 1 and 2).

The present disclosure further provides a method for treating a subject having a disease, disorder or condition associated with detrimental expression of a tumor antigen, comprises: administering to the subject a host cell, or a population of host cells, which harbors an expression vector operably linked to a nucleic acid that encodes the first and second polypeptide chains, comprising: (a) a first polypeptide chain comprising six regions ordered from the amino terminus to the carboxyl terminus: (i) a heavy chain leader sequence, (ii) an antibody heavy chain variable region, (iii) an antibody heavy chain constant region, (iv) an optional hinge region, (v) a transmembrane region, and (vi) an intracellular signaling region having two to five intracellular signaling sequences; and (b) a second polypeptide chain comprising: two regions ordered from the amino terminus to the carboxyl terminus: (i) an antibody light chain variable region, and (ii) an antibody light chain constant region (e.g., FIGS. 1 and 2).

In one embodiment, a method for treating a subject having a disease, disorder or condition associated with detrimental expression of a tumor antigen, comprises: administering to the subject a host cell, or a population of host cells, which expresses the first polypeptide chains, the second polypeptide chains, or the first and second polypeptide chains (e.g., FIGS. 1 and 2). In one embodiment, the first and second polypeptide chains dimerize to form a dimeric antigen receptor that binds specifically to the tumor antigen in the subject.

The present disclosure further provides a method for treating a subject having a disease, disorder or condition associated with detrimental expression of a tumor antigen, comprises: administering to the subject a host cell, or a population of host cells, which harbors an expression vector operably linked to a nucleic acid that encodes a first polypeptide chain comprising: six regions ordered from the amino terminus to the carboxyl terminus: (i) a light chain leader region, (ii) an antibody light chain variable region, (iii) an antibody light chain constant region, (iv) an optional hinge region, (v) a transmembrane region, and (vi) an intracellular signaling region (FIGS. 3 and 4).

The present disclosure further provides a method for treating a subject having a disease, disorder or condition associated with detrimental expression of a tumor antigen, comprises: administering to the subject a host cell, or a population of host cells, which harbors an expression vector operably linked to a nucleic acid that encodes a second polypeptide chain comprising: three regions ordered from the amino terminus to the carboxyl terminus: (i) a heavy chain leader region, (ii) an antibody heavy chain variable region, and (iii) an antibody light chain constant region (FIGS. 3 and 4).

The present disclosure further provides a method for treating a subject having a disease, disorder or condition associated with detrimental expression of a tumor antigen, comprises: administering to the subject a host cell, or a population of host cells, which harbors a first and second expression vector, wherein the first expression vector is operably linked to a nucleic acid that encodes the first polypeptide chain and the second expression vector is operably linked to a nucleic acid that encodes the second polypeptide chain, wherein (a) the first polypeptide chain comprising six regions ordered from the amino terminus to the carboxyl terminus: (i) a light chain leader sequence, (ii) an antibody light chain variable region, (iii) an antibody light chain constant region, (iv) an optional hinge region, (v) a transmembrane region, and (vi) an intracellular signaling region having two to five intracellular signaling sequences; and wherein (b) the second polypeptide chain comprising: two regions ordered from the amino terminus to the carboxyl terminus: (i) an antibody heavy chain variable region, and (ii) an antibody heavy chain constant region (FIGS. 3 and 4).

The present disclosure further provides a method for treating a subject having a disease, disorder or condition associated with detrimental expression of a tumor antigen, comprises: administering to the subject a host cell, or a population of host cells, which harbors an expression vector operably linked to a nucleic acid that encodes the first and second polypeptide chains, comprising: (a) a first polypeptide chain comprising six regions ordered from the amino terminus to the carboxyl terminus: (i) a light chain leader sequence, (ii) an antibody light chain variable region, (iii) an antibody light chain constant region, (iv) an optional hinge region, (v) a transmembrane region, and (vi) an intracellular signaling region having two to five intracellular signaling sequences; and (b) a second polypeptide chain comprising: two regions ordered from the amino terminus to the carboxyl terminus: (i) an antibody heavy chain variable region, and (ii) an antibody heavy chain constant region (FIGS. 3 and 4).

In one embodiment, a method for treating a subject having a disease, disorder or condition associated with detrimental expression of a tumor antigen, comprises: administering to the subject a host cell, or a population of host cells, which expresses the first polypeptide chains, the second polypeptide chains, or the first and second polypeptide chains (FIGS. 3 and 4). In one embodiment, the first and second polypeptide chains dimerize to form a dimeric antigen receptor that binds specifically to the tumor antigen in the subject.

The present disclosure further provides a method for treating a subject having a disease, disorder or condition associated with detrimental expression of a tumor antigen, comprises: administering to the subject a host cell, or a population of host cells, which harbors an expression vector operably linked to a nucleic acid that encodes a precursor polypeptide comprising: ten regions ordered from the amino terminus to the carboxyl terminus: (1) a heavy chain leader region, (2) an antibody heavy chain variable region, (3) an antibody heavy chain constant region, (4) an optional hinge region, (5) a transmembrane region, (6) an intracellular signaling region having two to five intracellular signaling sequences, (7) T2A cleavable sequence region, (8) a light chain leader region, (9) an antibody light chain variable region, and (10) an antibody light chain constant region (e.g., FIGS. 5 and 6). In one embodiment, the precursor polypeptide is cleaved to form first and second polypeptide chains that dimerize to form a dimeric antigen receptor that binds specifically to the tumor antigen in the subject.

The present disclosure further provides a method for treating a subject having a disease, disorder or condition associated with detrimental expression of a tumor antigen, comprises: administering to the subject a host cell, or a population of host cells, which harbors an expression vector operably linked to a nucleic acid that encodes a precursor polypeptide comprising: ten regions ordered from the amino terminus to the carboxyl terminus: (1) a light chain leader region, (2) an antibody light chain variable region, (3) an antibody light chain constant region, (4) an optional hinge region, (5) a transmembrane region, (6) an intracellular signaling region having two to five intracellular signaling sequences, (7) T2A cleavable sequence region, (8) a heavy chain leader region, (9) an antibody heavy chain variable region, and (10) an antibody heavy chain constant region (FIGS. 7 and 8). In one embodiment, the precursor polypeptide is cleaved to form first and second polypeptide chains that dimerize to form a dimeric antigen receptor that binds specifically to the tumor antigen in the subject.

In one embodiment, a method for treating a subject having a disease, disorder or condition associated with detrimental expression of a tumor antigen, comprises: administering to the subject a host cell, or a population of host cells, which harbors an expression vector operably linked to a nucleic acid that encodes a first polypeptide chain comprising five regions ordered from the amino terminus to the carboxyl terminus: (i) a CD38 antibody heavy chain variable region comprising the amino acid sequence of SEQ ID NO:1, (ii) a CD38 antibody heavy chain constant region comprising the amino acid sequence of SEQ ID NO:2, (iii) a CD28 hinge region comprising the amino acid sequence of SEQ ID NO:5, (iv) a CD28 transmembrane region comprising the amino acid sequence of SEQ ID NO:6, and (v) an intracellular signaling region comprising a 4-1BB intracellular signaling sequence comprising the amino acid sequence of SEQ ID NO:7 and a CD3zeta intracellular signaling sequence comprising the amino acid sequence of SEQ ID NO:9.

In one embodiment, a method for treating a subject having a disease, disorder or condition associated with detrimental expression of a tumor antigen, comprises: administering to the subject a host cell, or a population of host cells, which harbors an expression vector operably linked to a nucleic acid that encodes a second polypeptide chain comprising two regions ordered from the amino terminus to the carboxyl terminus: (i) a CD38 antibody light chain variable region comprising the amino acid sequence of SEQ ID NO:3, and (ii) a CD38 antibody light chain constant region comprising the amino acid sequence of SEQ ID NO:4.

In one embodiment, a method for treating a subject having a disease, disorder or condition associated with detrimental expression of a tumor antigen, comprises: administering to the subject a host cell, or a population of host cells, which harbors a first and second expression vector, wherein the first expression vector is operably linked to a nucleic acid that encodes the amino acid sequence of SEQ ID NO:13 or 16 and the second expression vector is operably linked to a nucleic acid that encode the amino acid sequence of SEQ ID NO: 14 or 17.

In one embodiment, a method for treating a subject having a disease, disorder or condition associated with detrimental expression of a tumor antigen, comprises: administering to the subject a host cell, or a population of host cells, which harbors a vector that is operably linked to a nucleic acid that encode the first and second polypeptide chains wherein the vector comprises the amino acid sequences of SEQ ID NOS: 13 and 14, or SEQ ID NOS: 16 and 17.

In one embodiment, a method for treating a subject having a disease, disorder or condition associated with detrimental expression of a tumor antigen, comprises: administering to the subject a host cell, or a population of host cells, which harbors an expression vector encoding a precursor polypeptide comprising the amino acid sequence of SEQ ID NO:15 or 18 (e.g., CD38 precursor, 2$^{nd}$ generation).

In one embodiment, a method for treating a subject having a disease, disorder or condition associated with detrimental expression of a tumor antigen, comprises: administering to the subject a host cell, or a population of host cells, which expresses the first polypeptide chains (SEQ ID NO: 13 or 16), the second polypeptide chains (SEQ ID NO: 14 or 17), the first and second polypeptide chains (SEQ ID NOS: 13 and 14, or SEQ ID NO:16 and 17) or the precursor polypeptide (SEQ ID NO:15 or 18). In one embodiment, the first polypeptide chain (SEQ ID NO: 13 or 16) includes or lacks the leader sequence underlined in FIG. 35B or C. In one embodiment, the second polypeptide chain (SEQ ID NO:14 or 17) includes or lacks the leader sequence underlined in FIG. 35B or C. In one embodiment, the first and second polypeptide chains dimerize to form a dimeric antigen receptor that binds specifically to the tumor antigen in the subject. In one embodiment, the precursor polypeptide is cleaved to form first and second polypeptide chains that dimerize to form a dimeric antigen receptor that binds specifically to the tumor antigen (e.g., CD38) in the subject.

The present disclosure provides a method of treating a subject having a disease, disorder or condition associated with detrimental expression of a tumor antigen, wherein the disorder is cancer, including, but not limited to hematologic breast cancer, ovarian cancer, prostate cancer, head and neck cancer, lung cancer, bladder cancer, melanoma, colorectal cancer, pancreatic cancer, lung cancer, liver cancer, renal cancer, esophageal cancer, leiomyoma, leiomyosarcoma, glioma, and glioblastoma.

In one embodiment, the cancer is a hematologic cancer selected from the group consisting of non-Hodgkin's lymphoma (NHL), Burkitt's lymphoma (BL), B chronic lymphocytic leukemia (B-CLL), B and T acute lymphocytic leukemia (ALL), T cell lymphoma (TCL), acute myeloid leukemia (AML), hairy cell leukemia (HCL), Hodgkin's Lymphoma (HL), chronic myeloid leukemia (CML) and multiple myeloma (MM).

The present disclosure provides a method for treating a subject having a disease, disorder or condition associated with detrimental expression of a tumor antigen, the method comprising: administering to the subject a host cell, or a population of host cells, which harbors an expression vector operably linked to a nucleic acid that encodes a Version 1 (e.g., V1) dimeric antigen receptors (DAR) construct comprising a first polypeptide chain carrying heavy chain variable (VH) and heavy chain constant regions (CH), and a second polypeptide chain carrying light chain variable (VL) and light chain constant regions (CL) (e.g., FIG. 1), wherein the host cell, or a population of host cells harbor (a) a first vector is operably linked to a first nucleic acid that encodes the first polypeptide chain comprising five regions ordered from the amino terminus to the carboxyl terminus: (i) an antibody heavy chain variable region (VH), (ii) an antibody heavy chain constant region (CH), (iii) a long hinge region comprising CD8 and CD28 hinge sequences (e.g., SEQ ID NO:19), (iv) a transmembrane region (TM) comprising CD28 transmembrane sequence (e.g., SEQ ID NO:6), and (v) an intracellular signaling region comprising CD28 signaling sequence (e.g., SEQ ID NO:8) and CD3-zeta signaling sequence having ITAM motifs 1, 2 and 3 (e.g., SEQ ID NO:9); (b) the first vector is operably linked to the second nucleic acid that encodes a second polypeptide chain comprising two regions ordered from the amino terminus to the carboxyl terminus: (i) an antibody light chain variable region (VL) (e.g., kappa or lambda), and (ii) an antibody light chain constant region (CL). In one embodiment, the antibody heavy chain variable region (VH) comprises an anti-CD38 heavy chain variable region sequence (e.g., SEQ ID NO: 1) and the antibody heavy chain constant region (CH) comprises an anti-CD38 heavy chain constant region sequence (e.g., SEQ ID NO:2).

The present disclosure provides a method for treating a subject having a disease, disorder or condition associated with detrimental expression of a tumor antigen, the method comprising: administering to the subject a host cell, or a population of host cells, which harbors an expression vector operably linked to a nucleic acid that encodes a Version 2 (e.g., V2) dimeric antigen receptors (DAR) construct comprising a first polypeptide chain carrying heavy chain variable (VH) and heavy chain constant regions (CH), and a second polypeptide chain carrying light chain variable (VL) and light chain constant regions (CL) (e.g., FIGS. 1 and 2), wherein the host cell, or a population of host cells harbor (a) a first vector operably linked to a first nucleic acid that encodes the first polypeptide chain comprising five regions ordered from the amino terminus to the carboxyl terminus: (i) an antibody heavy chain variable region (VH), (ii) an antibody heavy chain constant region (CH), (iii) a short hinge region comprising a CD28 hinge sequence (e.g., SEQ ID NO:5), (iv) a transmembrane region (TM) comprising CD28 transmembrane sequence (e.g., SEQ ID NO:6), and (v) an intracellular signaling region comprising either (1) a 4-1BB signaling sequence (e.g., SEQ ID NO:7) and CD3-zeta having ITAM motifs 1, 2 and 3 (e.g., SEQ ID NO:9), or (2) CD28 (e.g., SEQ ID NO:8) signaling sequence and CD3-zeta having ITAM motifs 1, 2 and 3 (e.g., SEQ ID NO:9), or (3) 4-1BB (e.g., SEQ ID NO:7) signaling sequence and CD28 (e.g., SEQ ID NO:8) signaling sequence and CD3-zeta having ITAM motifs 1, 2 and 3 (e.g., SEQ ID NO:9); (b) the first vector is operably linked to a second nucleic acid that encodes the second polypeptide chain comprising two regions ordered from the amino terminus to the carboxyl terminus: (i) an antibody light chain variable region (VL) (e.g., kappa or lambda), and (ii) an antibody light chain constant region (CL). In one embodiment, the Version 2a (V2a) DAR construct comprises the intracellular signaling region having the 4-1BB signaling sequence (e.g., SEQ ID NO:7) and CD3-zeta having ITAM motifs 1, 2 and 3 (e.g., SEQ ID NO:9). In one embodiment, the Version 2b (V2b) DAR construct comprises the intracellular signaling region having the CD28 (e.g., SEQ ID NO:8) signaling sequence and CD3-zeta having ITAM motifs 1, 2 and 3 (e.g., SEQ ID NO:9). In one embodiment, the Version 2c (V2c) DAR construct comprises the intracellular signaling region having the 4-1BB (e.g., SEQ ID NO:7) signaling sequence and CD28 (e.g., SEQ ID NO:8) signaling sequence and CD3-zeta having ITAM motifs 1, 2 and 3 (e.g., SEQ ID NO:9). In one embodiment, the DAR V2a and V2b are second generation DAR constructs, while the DAR V2c is a third generation DAR construct. In one embodiment, the antibody heavy chain variable region (VH) comprises an anti-CD38 heavy chain variable region sequence (e.g., SEQ ID NO:1) and the antibody heavy chain constant region (CH) comprises an anti-CD38 heavy chain constant region sequence (e.g., SEQ ID NO:2).

The present disclosure provides a method for treating a subject having a disease, disorder or condition associated with detrimental expression of a tumor antigen, the method comprising: administering to the subject a host cell, or a population of host cells, which harbors an expression vector operably linked to a nucleic acid that encodes a Version 3

(e.g., V3) dimeric antigen receptors (DAR) construct comprising a first polypeptide chain carrying heavy chain variable (VH) and heavy chain constant regions (CH), and a second polypeptide chain carrying light chain variable (VL) and light chain constant regions (CL) (e.g., FIG. 1), wherein the host cell, or a population of host cells harbor (a) a first vector operably linked to a first nucleic acid that encodes the first polypeptide chain comprising five regions ordered from the amino terminus to the carboxyl terminus: (i) an antibody heavy chain variable region (VH), (ii) an antibody heavy chain constant region (CH), (iii) a short hinge region comprising CD28 hinge sequences (e.g., SEQ ID NO:5), (iv) a transmembrane region (TM) comprising CD28 transmembrane sequence (e.g., SEQ ID NO:6), and (v) an intracellular signaling region comprising 4-1BB signaling sequence (e.g., SEQ ID NO:7) and CD3-zeta signaling sequence having only ITAM motif 3 (e.g., SEQ ID NO:20); (b) the first vector operably is linked to a second nucleic acid that encodes the second polypeptide chain comprising two regions ordered from the amino terminus to the carboxyl terminus: (i) an antibody light chain variable region (VL) (e.g., kappa or lambda), and (ii) an antibody light chain constant region (CL). In one embodiment, the antibody heavy chain variable region (VH) comprises an anti-CD38 heavy chain variable region sequence (e.g., SEQ ID NO:1) and the antibody heavy chain constant region (CH) comprises an anti-CD38 heavy chain constant region sequence (e.g., SEQ ID NO:2).

The present disclosure provides a method for treating a subject having a disease, disorder or condition associated with detrimental expression of a tumor antigen, the method comprising: administering to the subject a host cell, or a population of host cells, which harbors an expression vector operably linked to a nucleic acid that encodes a Version 4 (e.g., V4) dimeric antigen receptors (DAR) construct comprising a first polypeptide chain carrying heavy chain variable (VH) and heavy chain constant regions (CH), and a second polypeptide chain carrying light chain variable (VL) and light chain constant regions (CL), wherein the host cell, or a population of host cells harbor (a) a first vector operably linked to a first nucleic acid that encodes the first polypeptide chain comprising four regions ordered from the amino terminus to the carboxyl terminus: (i) an antibody heavy chain variable region (VH), (ii) an antibody heavy chain constant region (CH), (iii) a transmembrane region (TM) comprising CD28 transmembrane sequence (e.g., SEQ ID NO:6), and (iv) an intracellular signaling region comprising 4-1BB signaling sequence (e.g., SEQ ID NO:7) and CD3-zeta signaling sequence having only ITAM motif 3 (e.g., SEQ ID NO:20); (b) the first vector is operably linked to a second nucleic acid that encodes the second polypeptide chain comprising two regions ordered from the amino terminus to the carboxyl terminus: (i) an antibody light chain variable region (VL) (e.g., kappa or lambda), and (ii) an antibody light chain constant region (CL). The DAR V4 construct lacks a hinge sequence. In one embodiment, the antibody heavy chain variable region (VH) comprises an anti-CD38 heavy chain variable region sequence (e.g., SEQ ID NO: 1) and the antibody heavy chain constant region (CH) comprises an anti-CD38 heavy chain constant region sequence (e.g., SEQ ID NO: 2).

The present disclosure provides a method of treating a subject having a disease, disorder or condition associated with detrimental expression of a tumor antigen, wherein the disorder is cancer, including, but not limited to hematologic breast cancer, ovarian cancer, prostate cancer, head and neck cancer, lung cancer, bladder cancer, melanoma, colorectal cancer, pancreatic cancer, lung cancer, liver cancer, renal cancer, esophageal cancer, leiomyoma, leiomyosarcoma, glioma, and glioblastoma.

In one embodiment, the cancer is a hematologic cancer selected from the group consisting of non-Hodgkin's lymphoma (NHL), Burkitt's lymphoma (BL), B chronic lymphocytic leukemia (B-CLL), B and T acute lymphocytic leukemia (ALL), T cell lymphoma (TCL), acute myeloid leukemia (AML), hairy cell leukemia (HCL), Hodgkin's Lymphoma (HL), chronic myeloid leukemia (CML) and multiple myeloma (MM).

EXAMPLES

The following examples are meant to be illustrative and can be used to further understand embodiments of the present disclosure and should not be construed as limiting the scope of the present teachings in any way.

Example 1: Isolation of Human PBMC Cells and Primary T Cells

Primary human T cells were isolated from healthy human donors either from buffy coats (San Diego blood bank), fresh blood or leukapheresis products (StemCell). Peripheral blood mononuclear cells were isolated by density gradient centrifugation. T cells were isolated from PBMCs by magnetic negative selection using EasySep™ Human T Cell Isolation Kit (STEMCELL) according to manufacturer's instructions.

Example 2: Primary T Cell Culture

Primary T cells were cultured in CTS™ OpTmizer™ T Cell Expansion SFM supplemented with 5% CTS™ Immune Cell SR (Thermo Fisher Scientific) with 300 U/mL IL-2 (Proleukin) at a density of $10^6$ cells per mL. Isolated T cells were stimulated freshly or from the frozen tank. Cells were activated with T Cell TransAct (Miltenyi) 3 uL/$10^6$ cells per mL for two to three days. Following transfection, T cells were cultured in media with IL-2 at 300 U/mL.

Example 3: Tumor Cell Lines

Multiple myeloma cell line RPMI 8226 was obtained from ATCC and were transduced using a lentivirus carrying luciferase and GFP genes. A single cell clone with luciferase and GFP expression was selected (RPMI8226-FLuc). K562/RPE cells were made similarly by transducing the K562 cells with lentivirus carrying RPE genes. Both cell lines were cultured in RPMI1640 medium (ATCC) supplemented with 10% fetal bovine serum (Sigma).

Example 4: Preparation of CAR and DAR T Cells

Activated T cells were introduced with nucleic acids encoding either a CAR or DAR construct.

The nucleic acid encoding the anti-CD38 CAR polypeptide included a heavy chain signal peptide (SEQ ID NO:10) followed by 2 additional amino acid residues Asp and Ile, a myc tag EQKLISEEDL (SEQ ID NO: 24), the anti-CD38 heavy chain variable region (SEQ ID NO: 1), 15 amino acid linker GGGGSGGGGSGGGGS (SEQ ID NO:23), the anti-CD38 light chain variable region (SEQ ID NO:3), CD8 hinge region (SEQ ID NO:21), CD28 hinge region (SEQ ID NO:5), CD28 transmembrane region (SEQ ID NO:6), CD28 intracellular signaling region (SEQ ID NO:8), and CD3-zeta intracellular signaling region (SEQ ID NO:9). The full-length anti-CD38 CAR construct has the amino acid sequence of SEQ ID NO:22.

Examples of the nucleic acids encoding the anti-CD38 DAR precursor polypeptides (e.g., V2a or V3) comprise the amino acid sequence of SEQ ID NO:15 or 18.

Example 5: Cytotoxicity Assays

Two to three weeks after electroporation, the CAR, DAR and control T cells were subjected to nutrient starvation overnight with IL-2. The cells were co-cultured with the target cell mixture of CD38 positive RPMI-8226/GFP cells or CD38 negative K562/RPE cells. The ratio of effector to target cell ranged from 5:1 to 0.08:1. After overnight incubation, the cells were subjected to flow cytometry to measure the GFP cell population to determine the specific target cell killing by anti-CD38A2 CAR and DAR T cells.

Example 6: Cytokine Secretion Assays

Two to three weeks after electroporation, the CAR, DAR and control T cells were subjected to nutrient starvation overnight with IL-2. The cells were co-cultured with CD38 negative K562 or CD38 positive RPMI 8226 cells. The ratio of the effector to target cell was 2:1. After overnight incubation, the cells were centrifuged to collect the supernatant for detecting cytokine IL-2, IFN-gamma and TNF alpha (Affymetrix eBioscience) according to the manufacturer's instructions.

Example 7: Detecting Effector Memory T Cells

The DAR T cells were washed with DPBS 5% human serum albumin, then stained with anti-CD3-BV421 antibody (SK7, BioLegend) and PE or APC conjugated CD38-Fc protein (Chimerigen Laboratories) for 30-60 minutes at 4° C. The CD3 and CD38 were detected using iQue Screener Plus (Intellicyte Co). Markers for identifying effector memory T cells and central memory fraction of T cells were CD45RO (BioLegend) and CCR7 (BioLegend).

Example 8: In Vivo Tumor Killing

Tumoricidal activity of the anti-CD38A2 CART or DART cells was tested in a RPMI8226 xenograft mouse model. Multiple myeloma cell line RPMI8226 obtained from ATCC were transfected by a lentiviral vector with luciferase and GFP genes. A single clone with luciferase and GFP expression was selected (RPMI8226-FLuc). A total $7 \times 10^6$ cells of RPMI8226-Fluc were suspended in 200 μL PBS, and then injected intravenously into the tail vein of each mouse. The animals with very small or very large tumor burden were excluded based on the bioluminescence from IVIS imaging. The animals selected in study were randomized in different groups.

A single treatment of about 10 million engineered CAR or DAR T cells was administered via the tail vein in 200 μL of PBS at three weeks after tumor inoculation. The same amount of ATC or TRAC KO T cells, or 200 μL of PBS, were administered intravenously as the treatment control groups.

Tumor growth was monitored by measuring total photon flux with an IVIS Lumina III In Vivo Imaging System (Perkin Elmer Health Sciences, Inc) on the dorsal side of each mouse weekly after tumor cell inoculation until 4 or 5 weeks post treatment. The images were taken about 10 to 20 minutes after 150 mg/kg luciferin intraperitoneal administration.

Example 9: Results of T Cells Expressing DAR V1 Constructs

Figure 9:
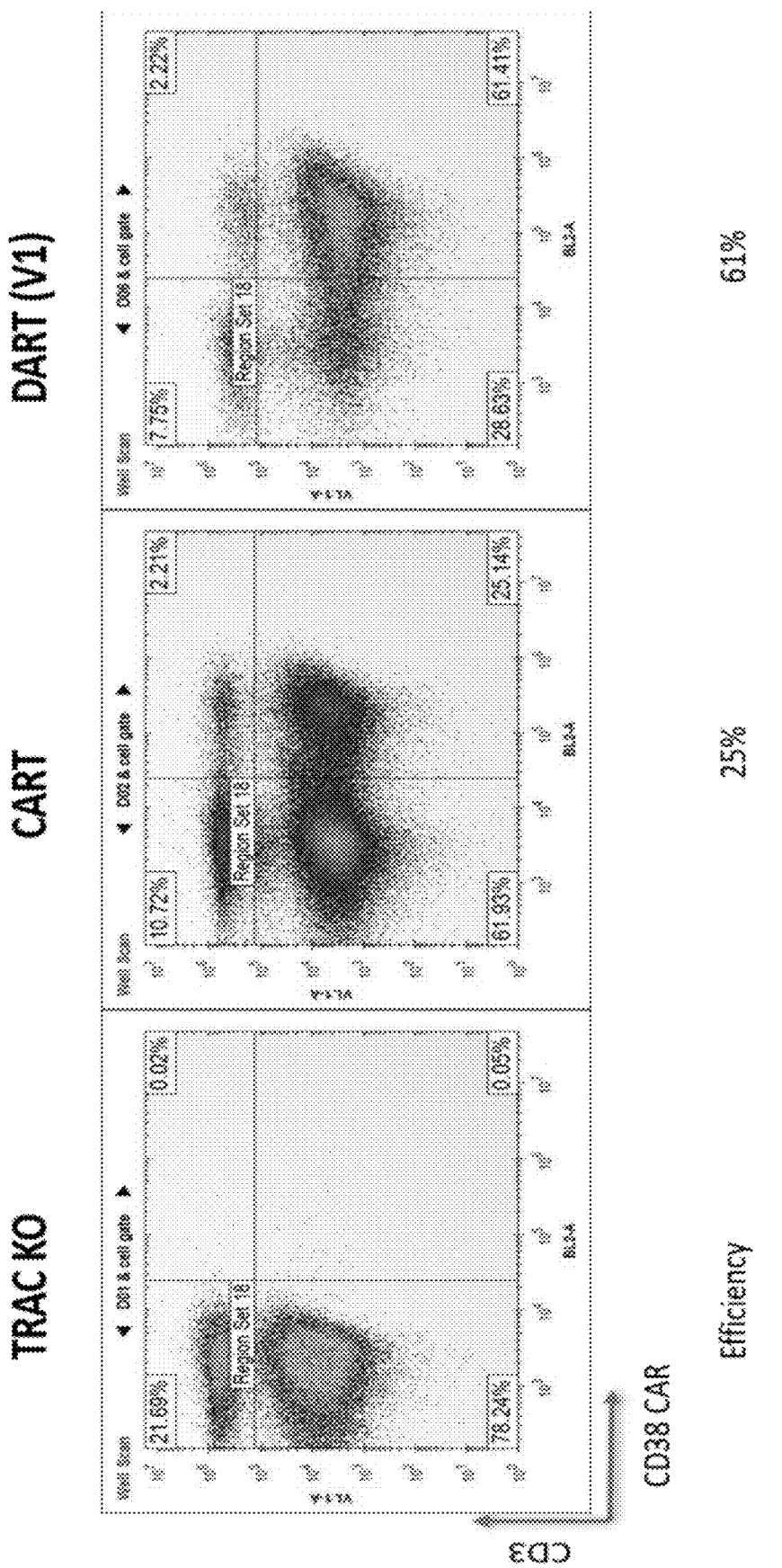
FIG. 9 shows the results of a flow cytometry study comparing T cells expressing a CD38 chimeric antigen receptor (CAR) construct compared to T cells expressing a CD38 dimeric antigen receptor (DAR) construct. The negative control is a cell line carrying a knocked-out TRAC (T-cell receptor alpha constant) gene. The DAR (V1) construct includes a long hinge sequence having CD8 and CD28 hinge sequences, and signaling regions include CD28 and long CD3zeta intracellular signaling sequences.

Expression levels of transgenic T cells expressing either anti-CD38 chimeric antigen receptor (CAR) or anti-CD38 dimeric antigen receptor (DAR) Version 1 were compared using flow cytometry. Transgenic T cells express a higher level of the Version 1 DAR construct compared to transgenic T cells expressing the CAR construct (FIG. 9).

Figure 10:
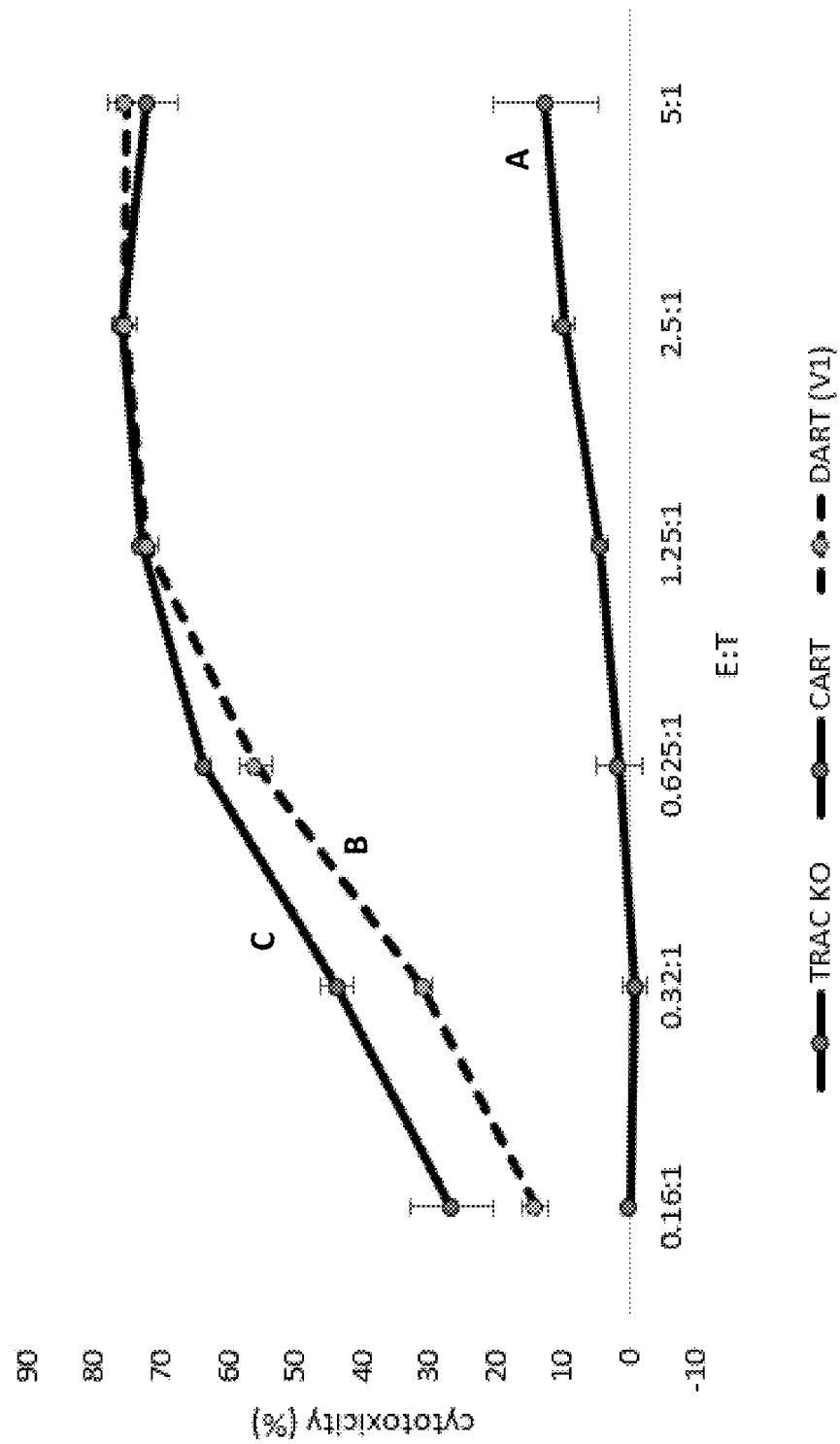
FIG. 10 is a graph showing the percent cytotoxicity of T cells expressing CD38 CAR, or CD38 DAR, on RPMI 8226 target cells. The negative control (line A) is a cell line carrying a knocked-out TRAC gene. The CD38 DAR (V1) construct (B dotted line) includes a long hinge sequence having CD8 and CD28 hinge sequences, and signaling regions include CD28 and long CD3zeta intracellular signaling sequences. The CD38 CAR construct is designated (line C).

Cell killing capability of T cells expressing either anti-CD38 chimeric antigen receptor (CAR) or anti-CD38 dimeric antigen receptor (DAR) Version 1 were compared in an in vitro cytotoxicity assay. Transgenic T cells expressing the Version 1 DAR construct (B dotted line) were comparable, but not better, at in vitro cell killing compared to transgenic T cells expressing the CAR construct (line C) (FIG. 10).

Figure 13:
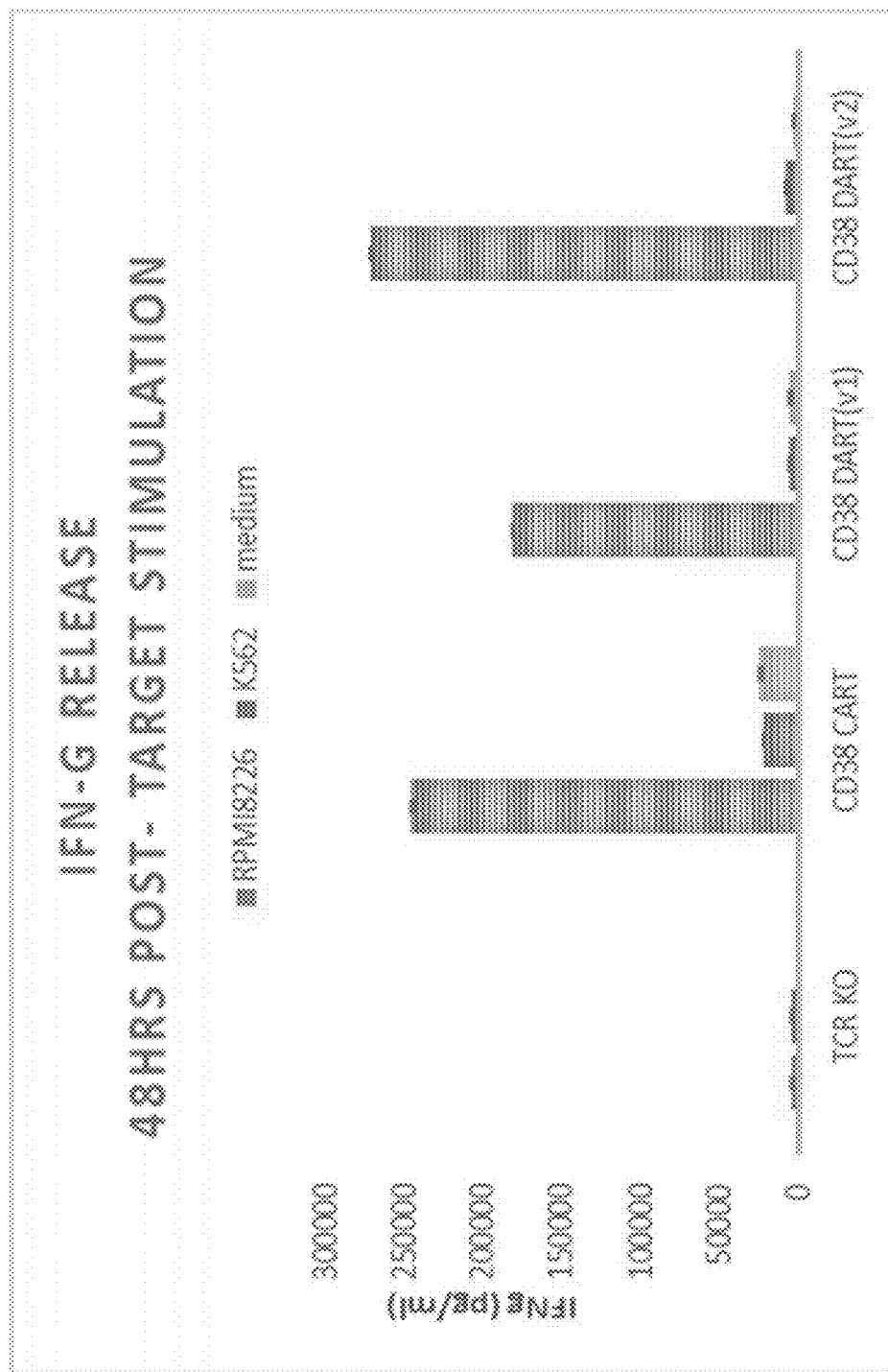
FIG. 13 is a bar graph showing the level of IFN-gamma release from T cells expressing CD38 CAR, CD38 DAR (V1) or CD38 DAR (V2b) constructs. Each data set shows from left to right RPMI 8226 cells, K562 cells and medium. The negative control is a cell line carrying a knocked-out TRAC (T-cell receptor alpha constant) gene. The CD38 DAR (V1) construct includes a long hinge sequence having CD8 and CD28 hinge sequences, and signaling regions include CD28 and long CD3zeta intracellular signaling sequences. The CD38 DAR (V2b) construct includes a short hinge sequence, and the signaling regions include CD28 and long CD3zeta intracellular signaling sequences.

Cytokine secretion capability of T cells expressing either anti-CD38 chimeric antigen receptor (CAR) or anti-CD38 dimeric antigen receptor (DAR) Version 1 were compared in an in vitro cytokine secretion assay. Transgenic T cells expressing the Version 1 DAR construct exhibited a higher level of tumor necrosis factor alpha (TNFα) secretion (FIG. 14) and IL-2 secretion (FIG. 15), but lower levels of interferon-gamma (IFNγ) (FIG. 13), compared to transgenic T cells expressing the CAR construct.

Figure 16:
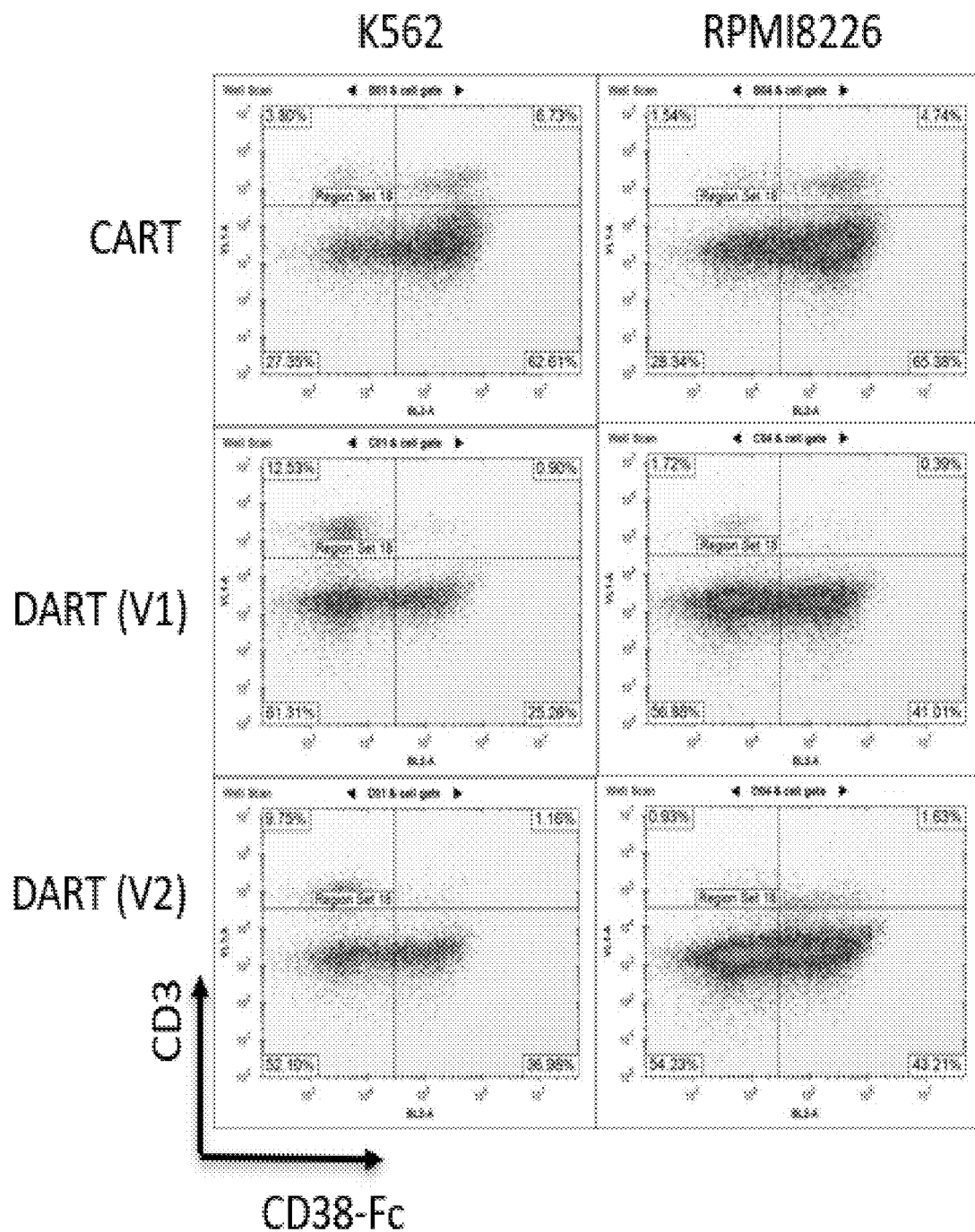
FIG. 16 shows the results of a flow cytometry study comparing expansion capability of T cells expressing a CAR, or a DAR (V1) or (V2b) construct, when co-cultured with K562 or RPMI 8226 cells. The negative control is a cell line carrying a knocked-out TRAC (T-cell receptor alpha constant) gene. The CD38 DAR (V1) construct includes a long hinge sequence having CD8 and CD28 hinge sequences, and signaling regions include CD28 and long CD3zeta intracellular signaling sequences. The CD38 DAR (V2b) construct includes a short hinge sequence, and the signaling regions include CD28 and long CD3zeta intracellular signaling sequences.
Figure 17:
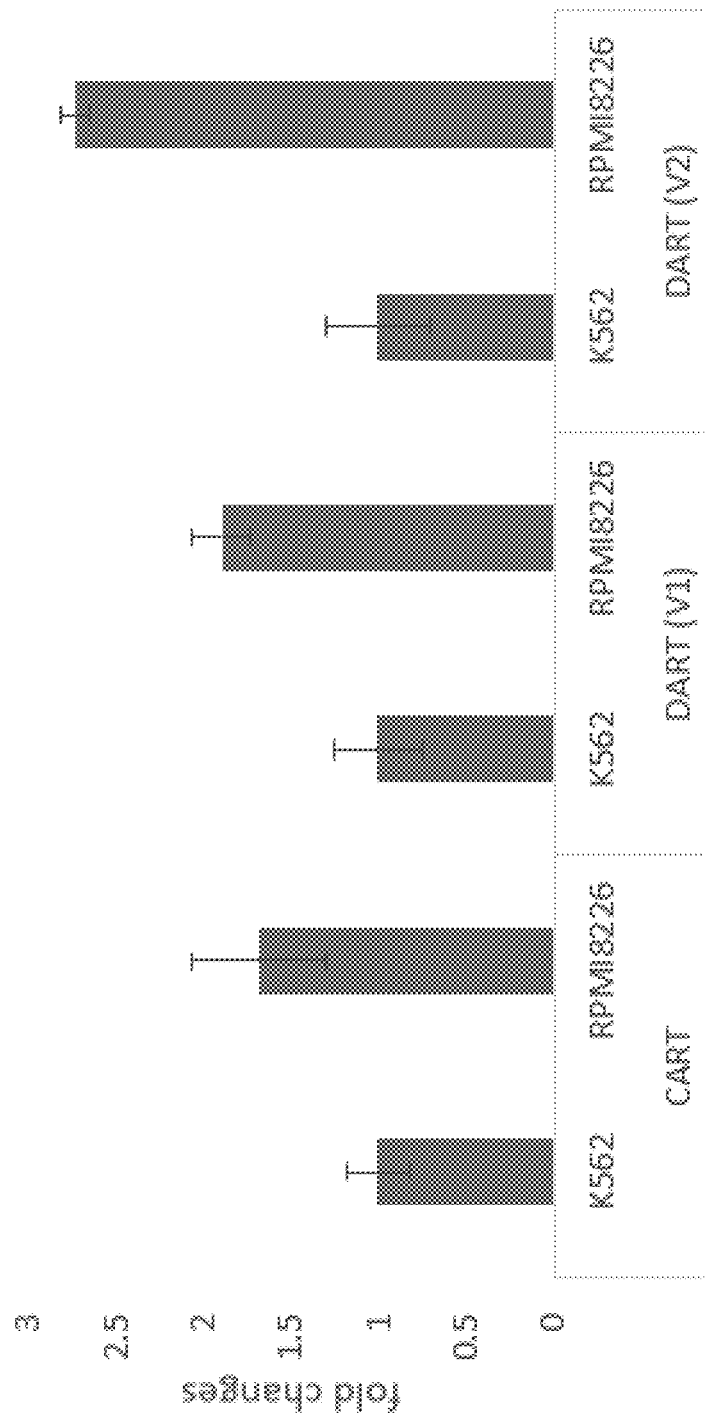
FIG. 17 is a bar graph showing the fold-change in expansion of T cells expressing a CAR, or a DAR (V1) or (V2b) construct, when co-cultured with K562 or RPMI 8226 cells. The negative control is a cell line carrying a knocked-out TRAC (T-cell receptor alpha constant) gene. The CD38 DAR (V1) construct includes a long hinge sequence having CD8 and CD28 hinge sequences, and signaling regions include CD28 and long CD3zeta intracellular signaling sequences. The CD38 DAR (V2b) construct includes a short hinge sequence, and the signaling regions include CD28 and long CD3zeta intracellular signaling sequences.

The capability for in vitro clonal expansion of T cells expressing either anti-CD38 chimeric antigen receptor (CAR) or anti-CD38 dimeric antigen receptor (DAR) Version 1, which were co-cultured with either RPMI 8226 or K562 tumor target cells, were compared using flow cytometry. Transgenic T cells expressing the Version 1 DAR construct exhibited a fold-change expansion that is comparable to T cells expressing the CAR construct (FIGS. 16 and 17).

Example 10: Results of T Cells Expressing DAR V2b Constructs

Figure 11:
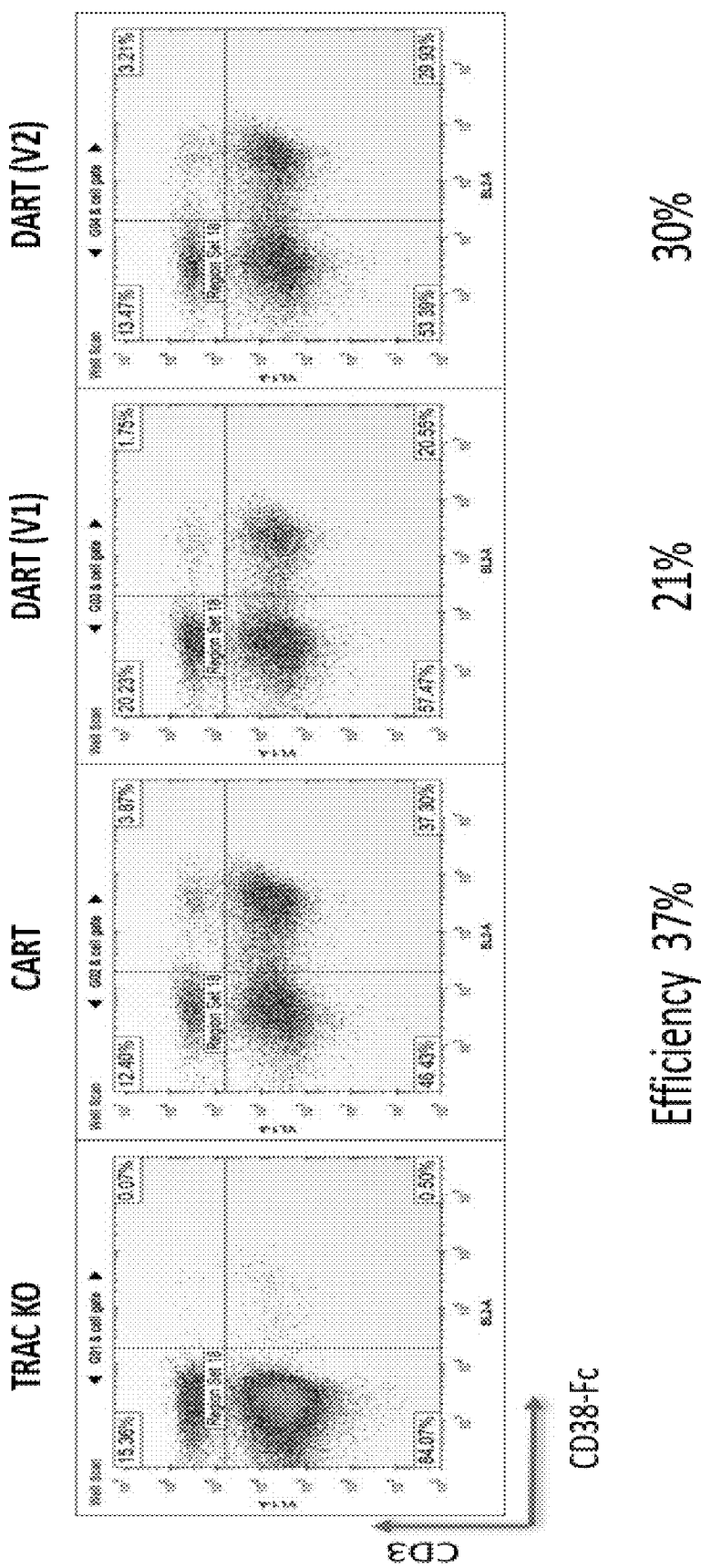
FIG. 11 shows the results of a flow cytometry study comparing T cells expressing CD38 CAR V1 or V2 constructs. The negative control is a cell line (TRAC KO) is the same that is described in FIG. 1. The CD38 DAR (V1) construct includes a long hinge sequence having CD8 and CD28 hinge sequences, and signaling regions include CD28 and long CD3zeta intracellular signaling sequences. The CD38 DAR (V2b) construct includes a short hinge sequence, and the signaling regions include CD28 and long CD3zeta intracellular signaling sequences.

Expression levels of transgenic T cells expressing either anti-CD38 chimeric antigen receptor (CAR) or anti-CD38 dimeric antigen receptor (DAR) V1 or V2b were compared using flow cytometry. Transgenic T cells express a higher level of the DAR V2b construct compared to transgenic T cells expressing the DAR V1 or CAR construct (FIG. 11).

Figure 12:
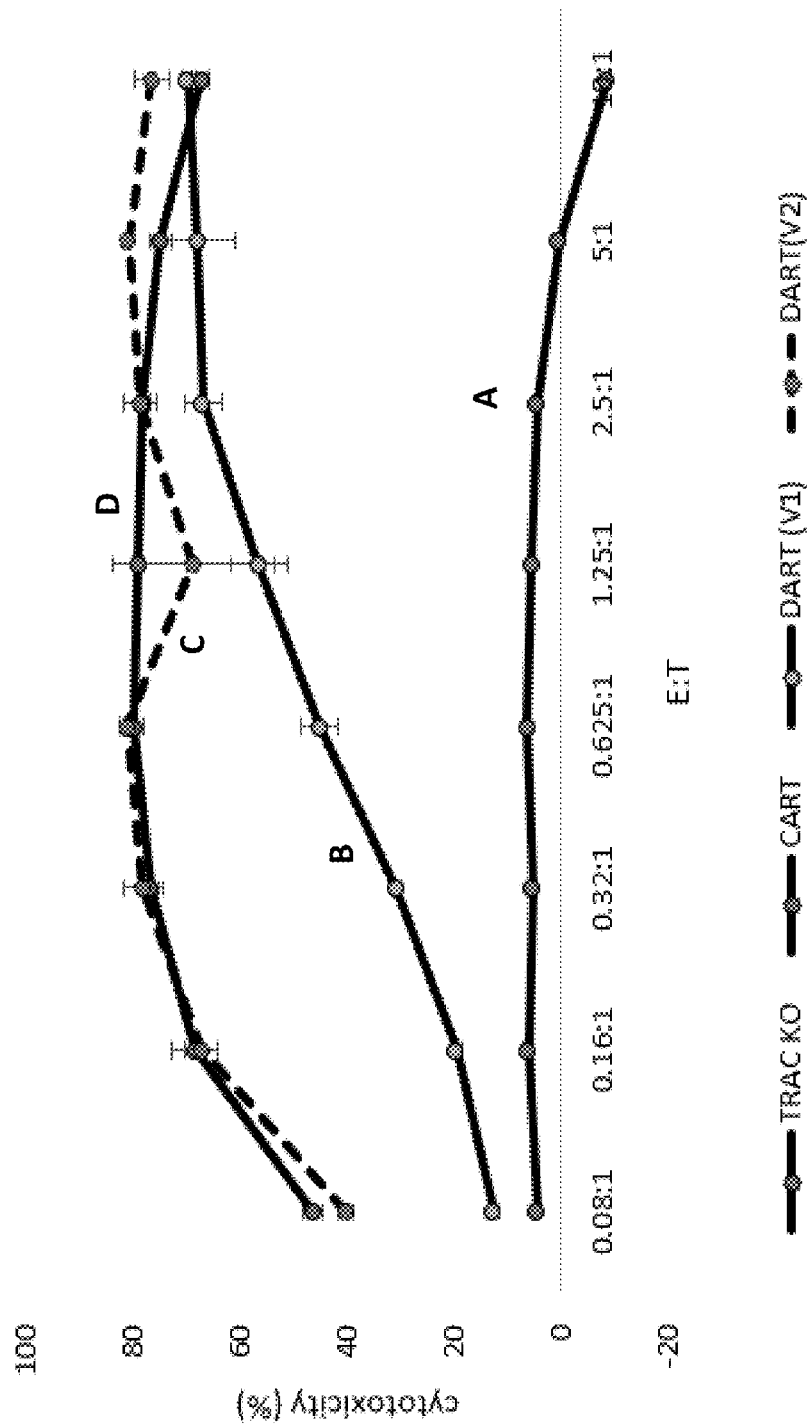
FIG. 12 is a graph showing the percent cytotoxicity of T cells expressing CD38 CAR, CD38 DAR (V1) or CD38 DAR (V2b) constructs, on RPMI 8226 target cells. The negative control (line A) is a cell line carrying a knocked-out TRAC gene. The CD38 DAR (V1) construct (line B) includes a long hinge sequence having CD8 and CD28 hinge sequences, and signaling regions include CD28 and long CD3zeta intracellular signaling sequences. The CD38 DAR (V2b) construct (C dotted line) includes a short hinge sequence, and the signaling regions include CD28 and long CD3zeta intracellular signaling sequences. The CD38 CAR is designated (line D).

Cell killing capability of T cells expressing either anti-CD38 chimeric antigen receptor (CAR) or anti-CD38 dimeric antigen receptor (DAR) V1 or V2b were compared in an in vitro cytotoxicity assay. Transgenic T cells expressing the DAR V2b construct (C dotted line) exhibited better in vitro cell killing compared to transgenic T cells expressing the DAR V1 construct (line B), and the DAR V2b expressing T cells were similar at in vitro cell killing compared to transgenic T cells expressing the CAR construct (line D) (FIG. 12).

Figure 26:
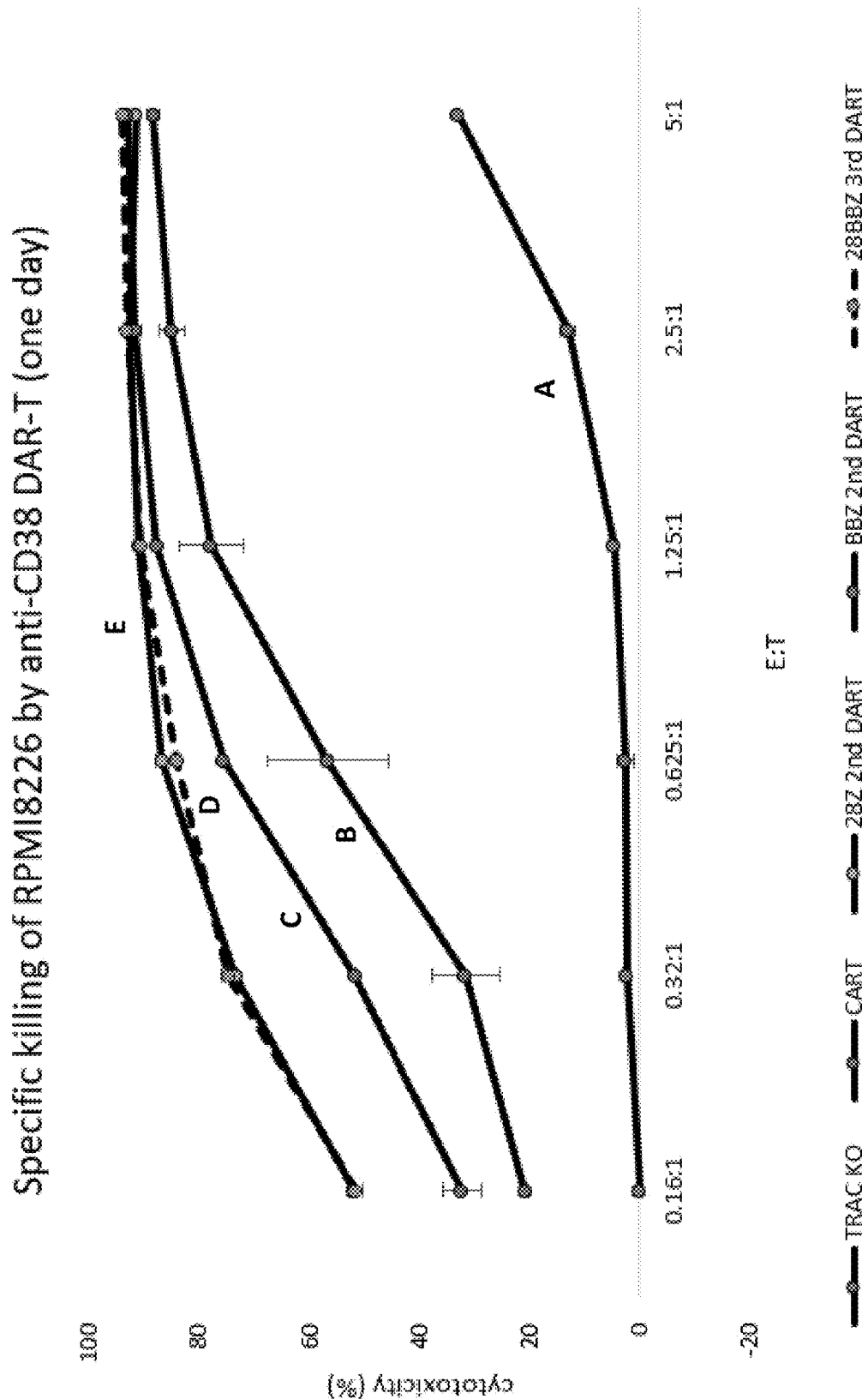
FIG. 26 is a graph showing the percent cytotoxicity of T cells expressing CD38 CAR, one of two different CD38 second generation DAR, or a CD38 third generation DAR construct, on RPMI 8226 target cells. The negative control (line A) is a cell line carrying a knocked-out TRAC gene. The 28Z second generation construct (line E) includes a short hinge sequence, and the signaling region includes CD28 and CD3zeta signaling sequences (e.g., a DAR (V2b construct). The BBZ second generation construct (line C) includes a short hinge sequence, and the signaling region includes 4-1BB and CD3zeta signaling sequences (e.g., a DAR (V2a) construct). The 28BBZ third generation construct (line D dotted line) includes a short hinge, and the signaling region includes CD28, 4-1BB and CD3zeta signaling sequences (e.g., a DAR (V2c) construct). The cells expressing CD38 CAR are designated (line B).

Cell killing capability of T cells expressing either anti-CD38 chimeric antigen receptor (CAR) or anti-CD38 dimeric antigen receptor (DAR) V2a, V2b or V2c construct were compared in an in vitro cytotoxicity assay. Transgenic T cells expressing the DAR V2b construct ("28Z" line E) exhibited markedly better in vitro cell killing compared to transgenic T cells expressing the CAR construct (line B) and T cells expressing DAR V2a ("BBZ" line C), and a similar killing capability compared to T cells expressing the DAR V2c ("28BBZ" dotted line D) (FIG. 26).

Figure 14:
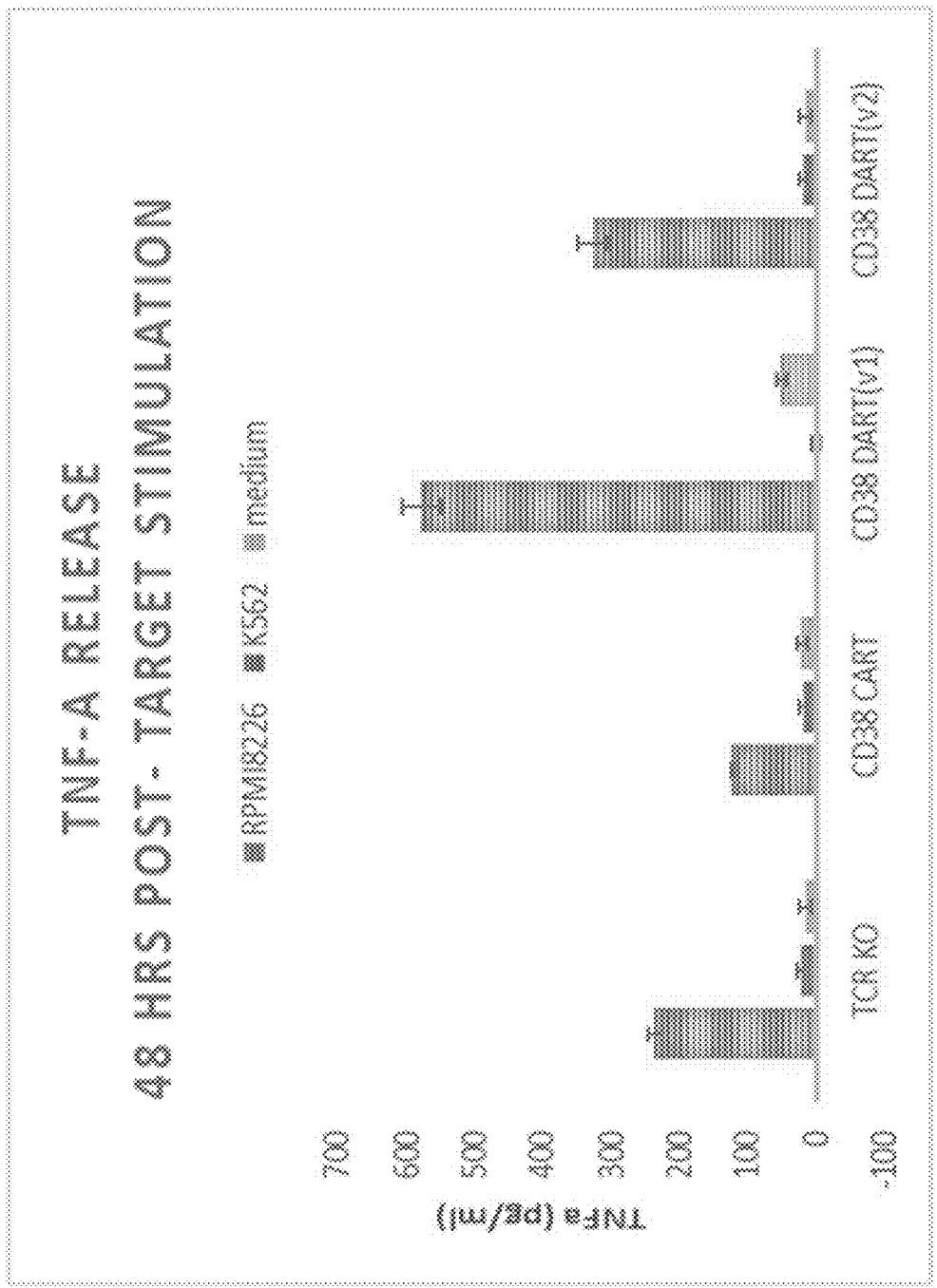
FIG. 14 is a bar graph showing the level of TNF-alpha release from T cells expressing CD38 CAR, CD38 DAR (V1) or CD38 DAR (V2b) constructs. Each data set shows from left to right RPMI 8226 cells, K562 cells and medium. The negative control is a cell line carrying a knocked-out TRAC (T-cell receptor alpha constant) gene. The CD38 DAR (V1) construct includes a long hinge sequence having CD8 and CD28 hinge sequences, and signaling regions include CD28 and long CD3zeta intracellular signaling sequences. The CD38 DAR (V2b) construct includes a short hinge sequence, and the signaling regions include CD28 and long CD3zeta intracellular signaling sequences.
Figure 15:
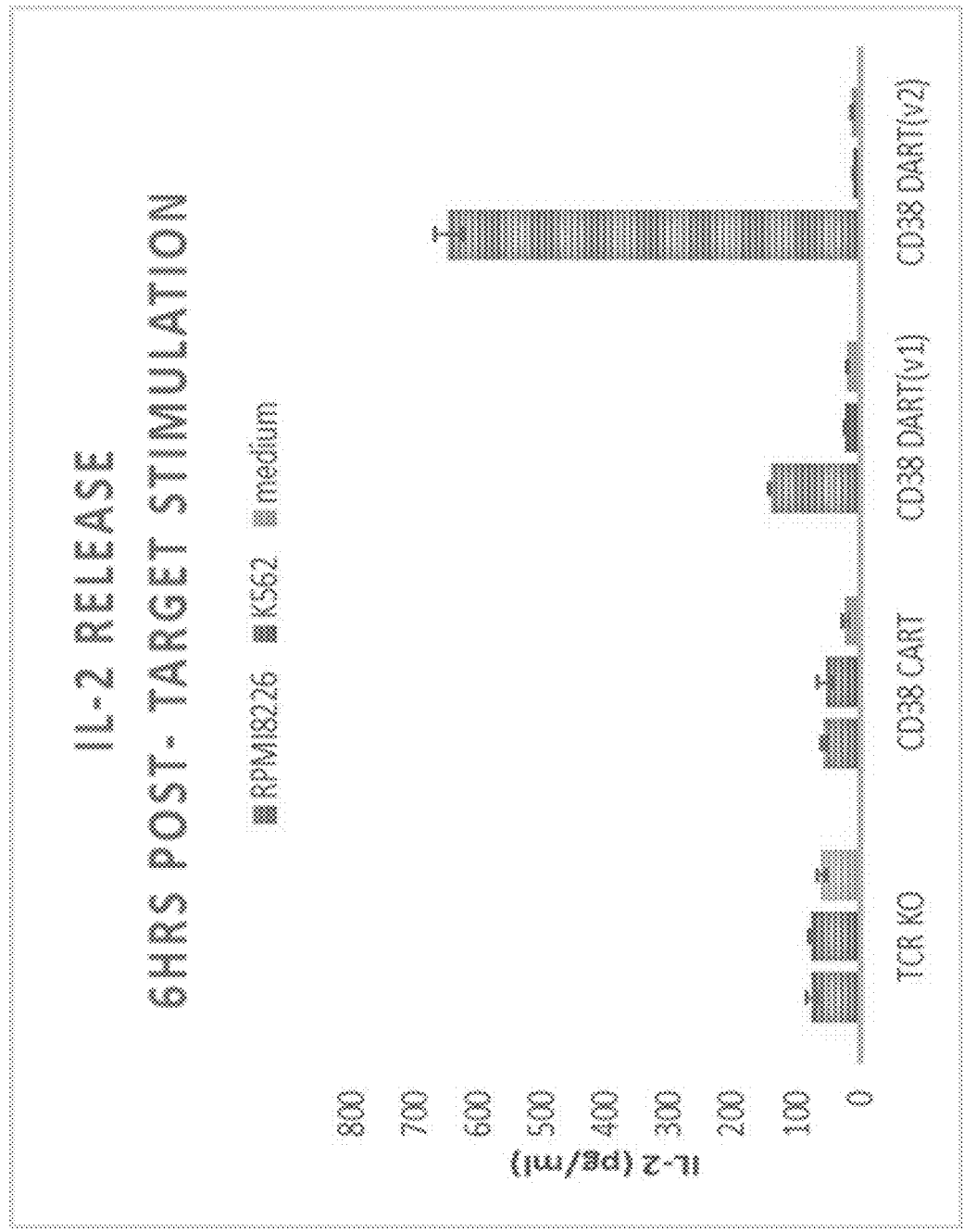
FIG. 15 is a bar graph showing the level of IL-2 release from T cells expressing CD38 CAR, CD38 DAR (V1) or CD38 DAR (V2b) constructs. Each data set shows from left to right RPMI 8226 cells, K562 cells and medium. The negative control is a cell line carrying a knocked-out TRAC gene. The CD38 DAR (V1) construct includes a long hinge sequence having CD8 and CD28 hinge sequences, and signaling regions include CD28 and long CD3zeta intracellular signaling sequences. The CD38 DAR (V2b) construct includes a short hinge sequence, and the signaling regions include CD28 and long CD3zeta intracellular signaling sequences.

Cytokine secretion capability of T cells expressing either anti-CD38 chimeric antigen receptor (CAR) or anti-CD38 dimeric antigen receptor (DAR) V1 or V2b were compared in an in vitro cytokine secretion assay. Transgenic T cells expressing the DAR V2b construct exhibited a higher level of IL-2 secretion compared to transgenic T cells expressing CAR or DAR V1 constructs (FIG. 15). Transgenic T cells expressing the DAR V2b construct exhibited a slightly higher level of interferon-gamma (IFNγ) secretion compared to transgenic T cells expressing the CAR construct (FIG. 13) and higher levels compared to transgenic T cells expressing the DAR V1 construct. Transgenic T cells expressing the DAR V2b construct exhibited a lower level of tumor necrosis factor alpha (TNFα) secretion compared to transgenic T cells expressing the CAR or DAR V1 construct (FIG. 14).

Flow cytometry was used to measure the capability for in vitro clonal expansion of T cells expressing either anti-CD38 chimeric antigen receptor (CAR) or anti-CD38 dimeric antigen receptor (DAR) V1 or V2b, which were co-cultured with either RPMI 8226 or K562 cells. Transgenic T cells expressing the DAR V2b construct exhibited a higher level of fold-change expansion compared to T cells expressing the CAR or DAR V1 construct, when co-cultured with RPMI 8226 cells (FIGS. 16 and 17).

Figure 18:
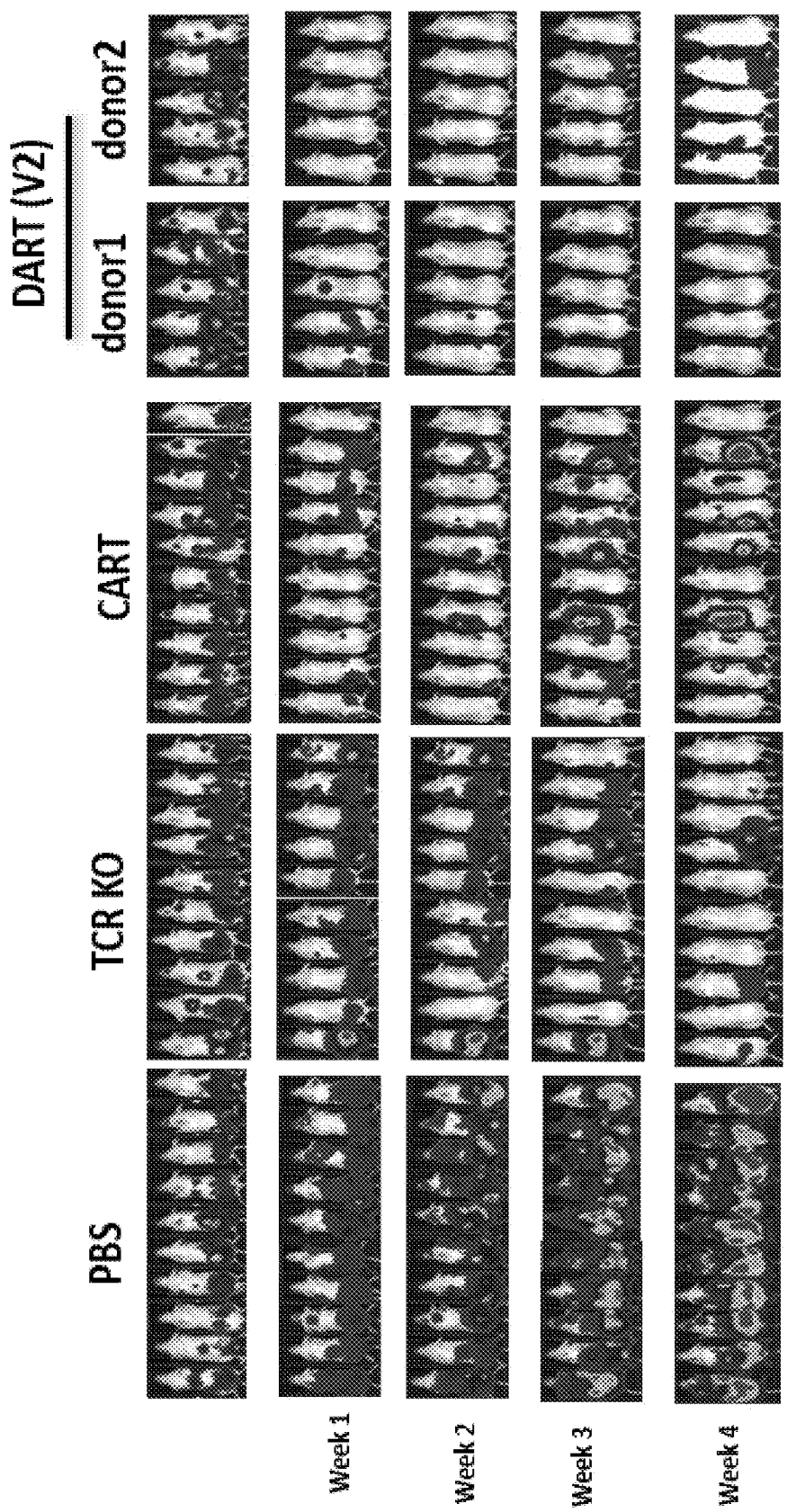
FIG. 18 shows tumoricidal activity of the CD38 DAR T cells assessed in a xenograft animal model. The negative control mice were administered phosphate-buffered saline or a cell line carrying a knocked-out TRAC gene. The test mice were administered T cells expressing CD38 DAR (V2b) construct which include a short hinge sequence, and the signaling regions include CD28 and long CD3zeta intracellular signaling sequences.

An in vivo xenograft animal model was used to measure the tumoricidal activity of the CD38 DAR T cells in a xenograft animal model. The negative control mice were administered phosphate-buffered saline or a cell line carrying a knocked-out TRAC gene. The test mice were administered transgenic T cells expressing either CD38 CAR or CD38 DAR (V2b) construct. At week 4, the mice that were treated with T cells expressing the CD38 DAR (V2b) constructs exhibited significantly less tumor burden compared to mice treated with T cells expressing a CD38 CAR construct (FIG. 18).

Example 11: Results of T Cells Expressing DAR V2c Constructs

Figure 25:
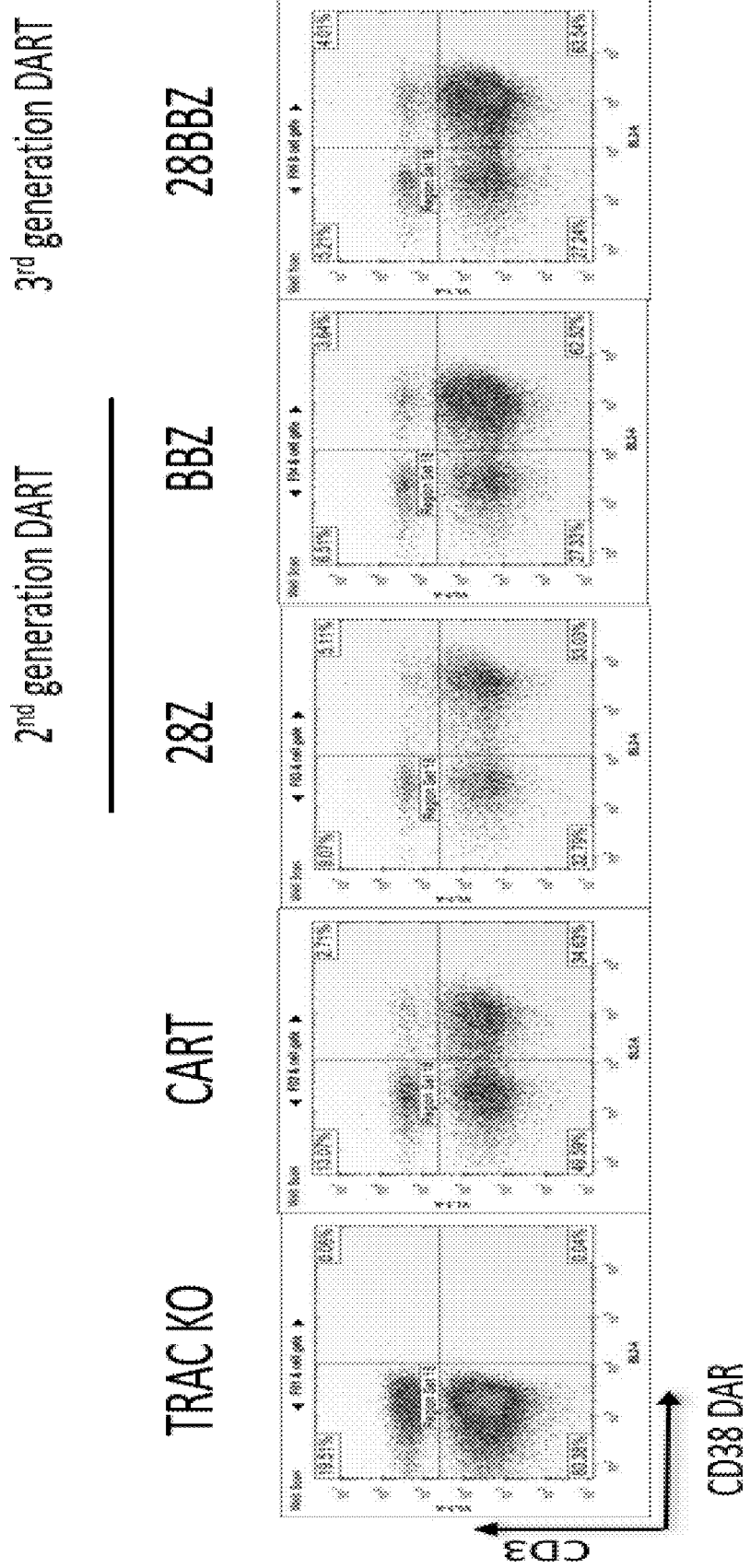
FIG. 25 shows the results of a flow cytometry study comparing T cells expressing a CD38 CAR, CD38 DAR second generation and CD38 DAR third generation constructs. The negative control is a cell line carrying a knocked-out TRAC gene. The 28Z second generation construct includes a short hinge sequence, and the signaling region includes CD28 and CD3zeta signaling sequences (e.g., a DAR (V2b) construct). The BBZ second generation construct includes a short hinge sequence, and the signaling region includes 4-1BB and CD3zeta signaling sequences (e.g., a DAR (V2a) construct). The 28BBZ third generation construct includes a short hinge, and the signaling region includes CD28, 4-1BB and CD3zeta signaling sequences (e.g., a DAR (V2c) construct).

Expression levels of transgenic T cells expressing either anti-CD38 chimeric antigen receptor (CAR) or anti-CD38 dimeric antigen receptor (DAR) V2a, V2b or V2c construct were compared using flow cytometry. Transgenic T cells express a similar level of the DAR V2c (e.g., "28BBZ") construct compared to transgenic T cells expressing the DAR V2a (e.g., "BBZ"), and a slightly higher level of DAR V2c ("28BBZ") is expressed compared to T cells expressing DAR V2b ("28Z") construct (FIG. 25).

Cell killing capability of T cells expressing either anti-CD38 chimeric antigen receptor (CAR) or anti-CD38 dimeric antigen receptor (DAR) V2a, V2b or V2c construct were compared in an in vitro cytotoxicity assay. Transgenic T cells expressing the DAR V2c construct ("28BBZ" dotted line D) exhibited a markedly higher level of in vitro cell killing compared to transgenic T cells expressing the CAR construct (line B) and DAR V2a construct (line C), but a similar level of cell killing compared to T cells expressing the DAR V2b ("28Z" line E) (FIG. 26).

Figure 27:
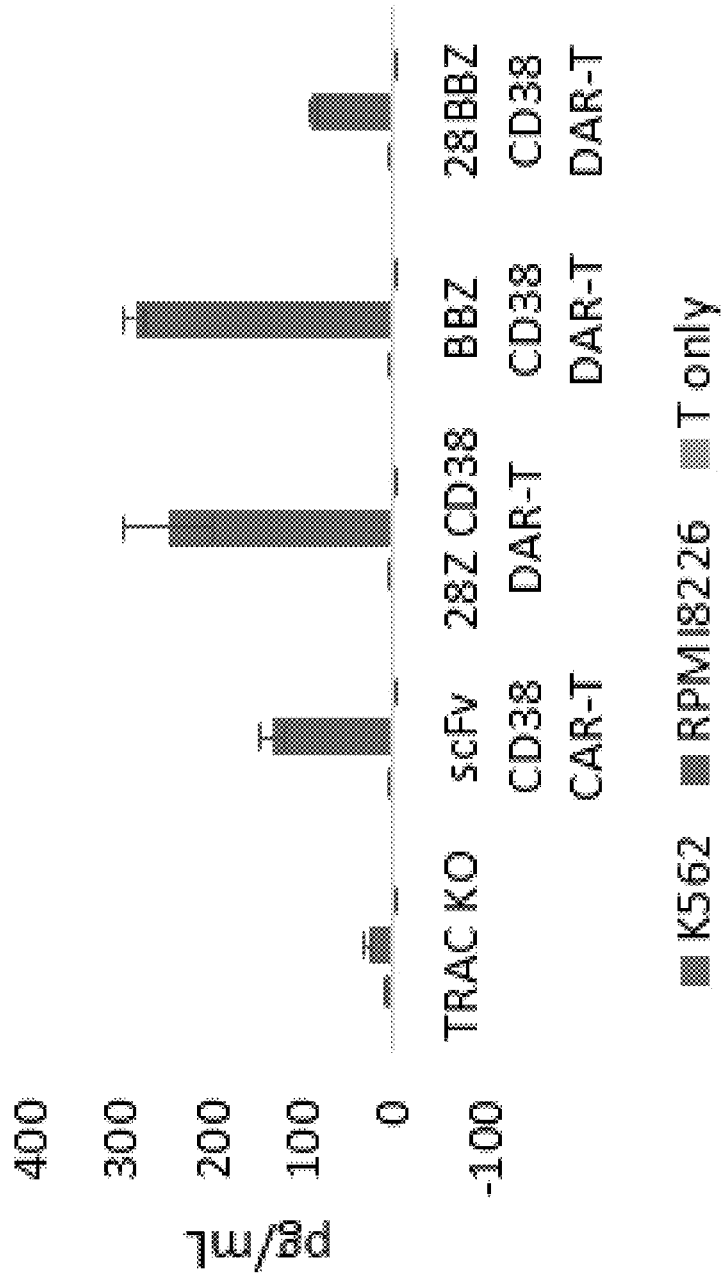
FIG. 27 is a bar graph showing the level of IL-2 secretion from T cells expressing CD38 CAR, one of two different CD38 second generation DAR, or a CD38 third generation DAR. Each data set shows from left to right K562 cells, RPMI 8226 cells and T cells only. The negative control is a cell line carrying a knocked-out TRAC gene. The 28Z second generation construct includes a short hinge sequence, and the signaling region includes CD28 and CD3zeta signaling sequences (e.g., a DAR (V2b) construct). The BBZ second generation construct includes a short hinge sequence, and the signaling region includes 4-1BB and CD3zeta signaling sequences (e.g., a DAR (V2a) construct). The 28BBZ third generation construct includes a short hinge, and the signaling region includes CD28, 4-1BB and CD3zeta signaling sequences (e.g., a DAR (V2c) construct).
Figure 28:
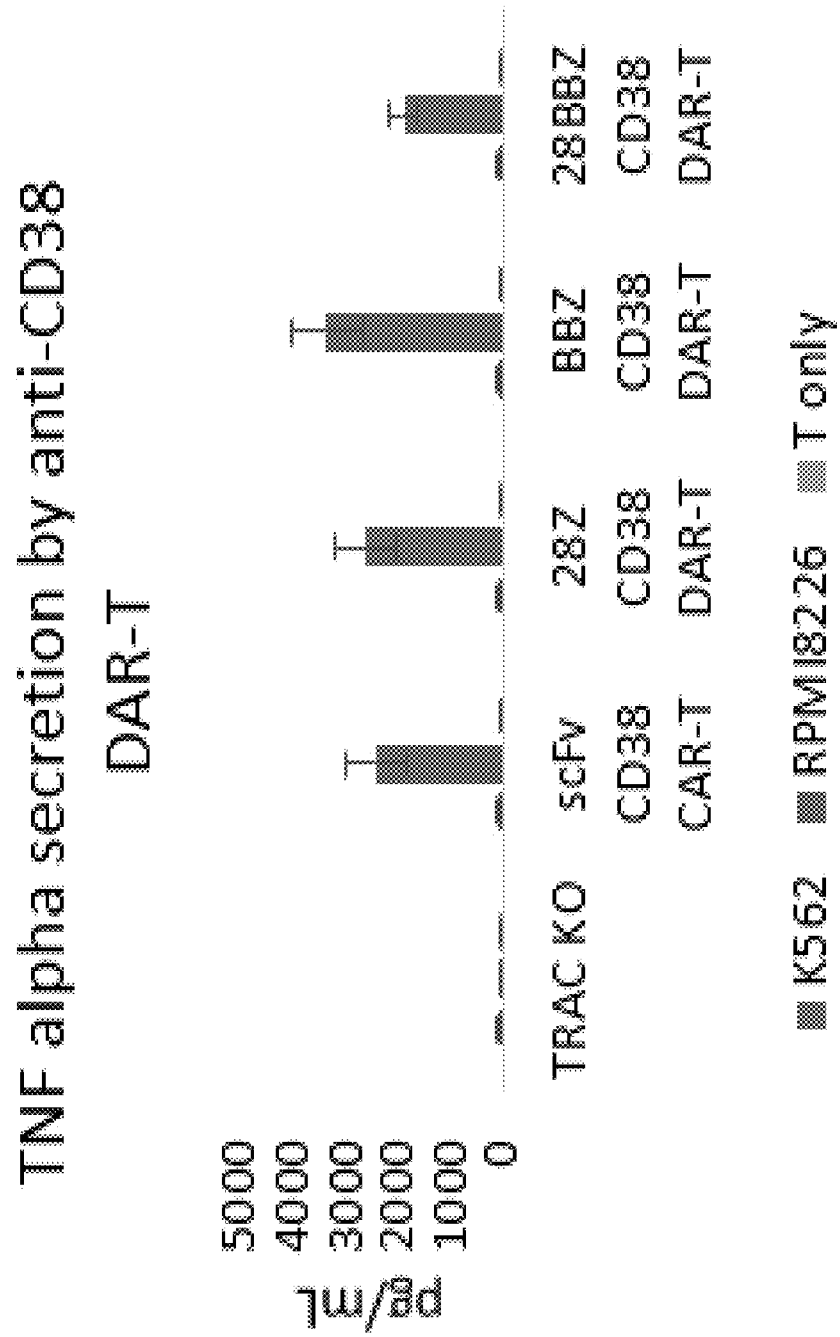
FIG. 28 is a bar graph showing the level of TNF-alpha secretion from T cells expressing CD38 CAR, one of two different CD38 second generation DAR, or a CD38 third generation DAR. Each data set shows from left to right K562 cells, RPMI 8226 cells and T cells only. The negative control is a cell line carrying a knocked-out TRAC gene. The 28Z second generation construct includes a short hinge sequence, and the signaling region includes CD28 and CD3zeta signaling sequences (e.g., a DAR (V2b) construct). The BBZ second generation construct includes a short hinge sequence, and the signaling region includes 4-1BB and CD3zeta signaling sequences (e.g., a DAR (V2a) construct). The 28BBZ third generation construct includes a short hinge, and the signaling region includes CD28, 4-1BB and CD3zeta signaling sequences (e.g., a DAR (V2c) construct).
Figure 29:
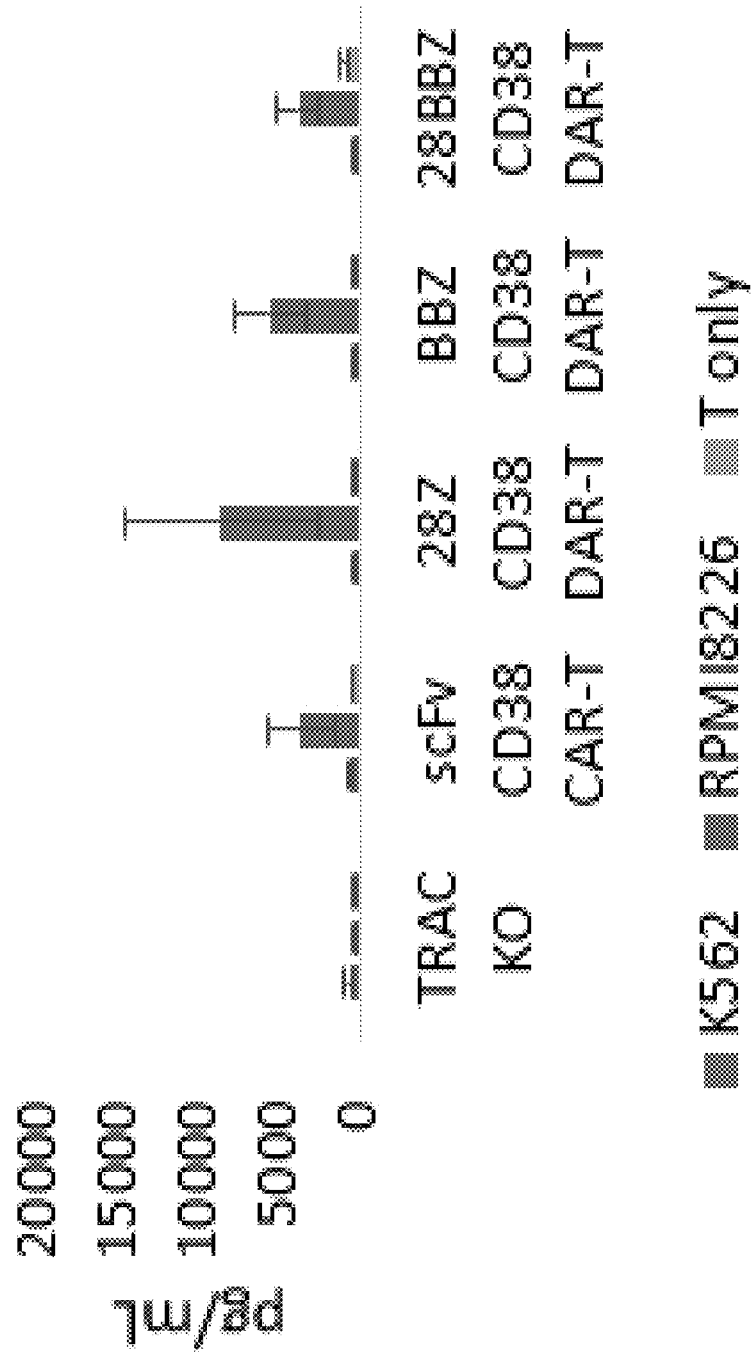
FIG. 29 is a bar graph showing the level of IFN-gamma secretion from T cells expressing CD38 CAR, one of two different CD38 second generation DAR, or a CD38 third generation DAR. Each data set shows from left to right K562 cells, RPMI 8226 cells and T cells only. The negative control is a cell line carrying a knocked-out TRAC gene. The 28Z second generation construct includes a short hinge sequence, and the signaling region includes CD28 and CD3zeta signaling sequences (e.g., a DAR (V2b) construct). The BBZ second generation construct includes a short hinge sequence, and the signaling region includes 4-1BB and CD3zeta signaling sequences (e.g., a DAR (V2a) construct). The 28BBZ third generation construct includes a short hinge, and the signaling region includes CD28, 4-1BB and CD3zeta signaling sequences (e.g., a DAR (V2c) construct).

Cytokine secretion capability of T cells expressing either anti-CD38 chimeric antigen receptor (CAR) or anti-CD38 dimeric antigen receptor (DAR) V2a or V2b construct were compared in an in vitro cytokine secretion assay. Transgenic T cells expressing the DAR V2a ("BBZ") exhibited a slightly higher level of IL-2 secretion compared to T cells expressing the DAR V2b ("28Z") construct, and a higher level compared to transgenic T cells expressing CAR construct (FIG. 27). Transgenic T cells expressing the DAR V2a ("BBZ") construct exhibited a slightly higher level of tumor necrosis factor alpha (TNFα) secretion compared to transgenic T cells expressing the CAR or DAR V2b ("28Z") construct (FIG. 28). Transgenic T cells expressing the DAR V2a ("BBZ") construct exhibited a slightly higher level of interferon-gamma (IFNγ) secretion compared to transgenic T cells expressing the CAR construct, but the cell expressing the DAR V2a ("BBZ") exhibited a slightly lower level of IFNγ secretion compared to transgenic T cells expressing the DAR V2b ("28Z") construct (FIG. 29).

Figure 19:
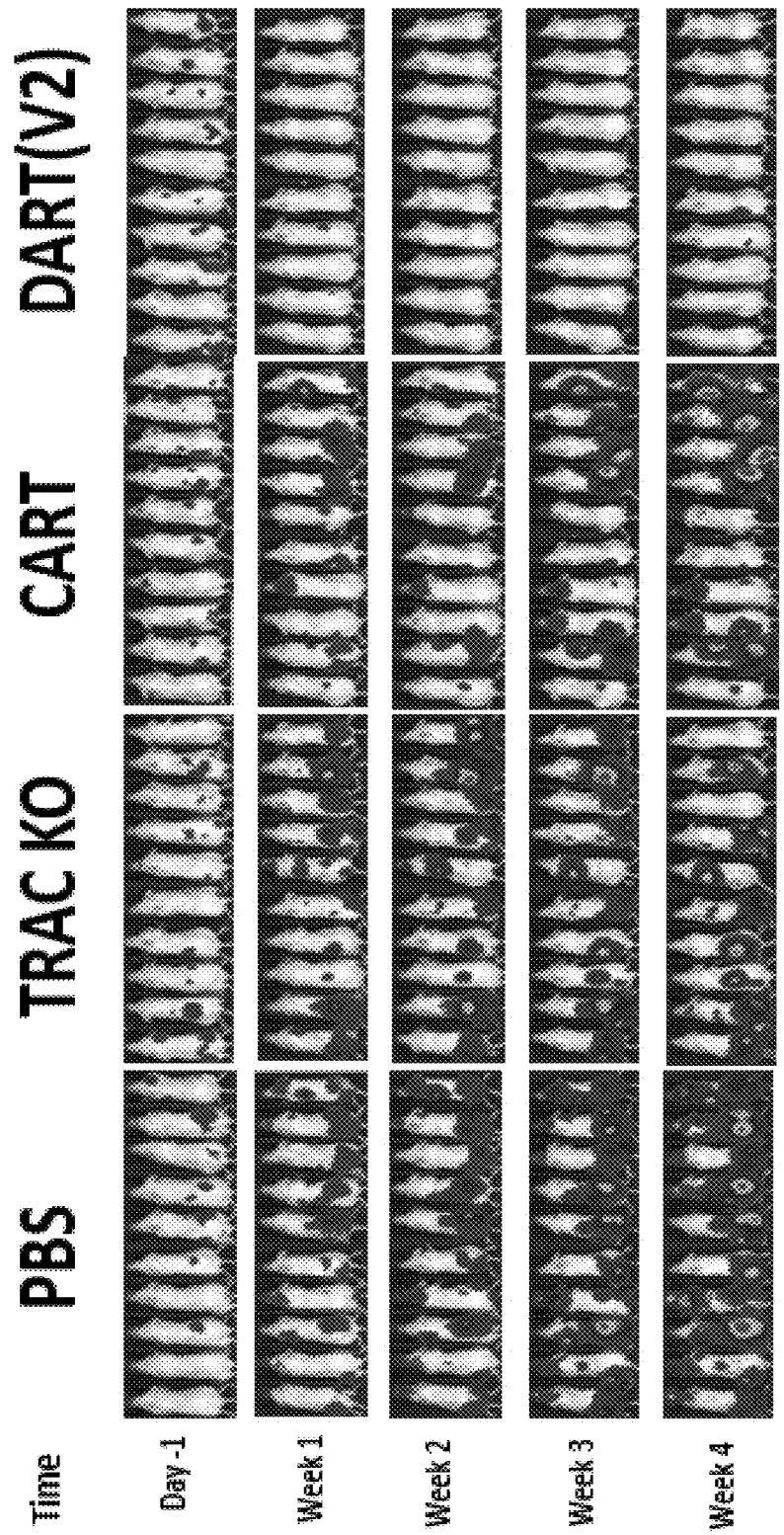
FIG. 19 shows tumoricidal activity of the CD38 DAR (V2a) T cells assessed in a xenograft animal model. The negative control mice were administered phosphate-buffered saline or a cell line carrying a knocked-out TRAC gene. The test mice were administered T cells expressing CD38 DAR (V2a) construct which include a short hinge sequence, and the signaling regions include 4-1BB and long CD3zeta intracellular signaling sequences.

An in vivo xenograft animal model was used to measure the tumoricidal activity of the CD38 DAR T cells in a xenograft animal model. The negative control mice were administered phosphate-buffered saline ("PBS") or a cell line carrying a knocked-out TRAC gene ("TRAC KO"). The test mice were administered transgenic T cells expressing either CD38 CAR or CD38 DAR (V2a) construct. At week 4, the mice that were treated with T cells expressing the CD38 DAR (V2a) constructs exhibited significantly less tumor burden compared to mice treated with T cells expressing a CD38 CAR construct (FIG. 19).

Figure 30:
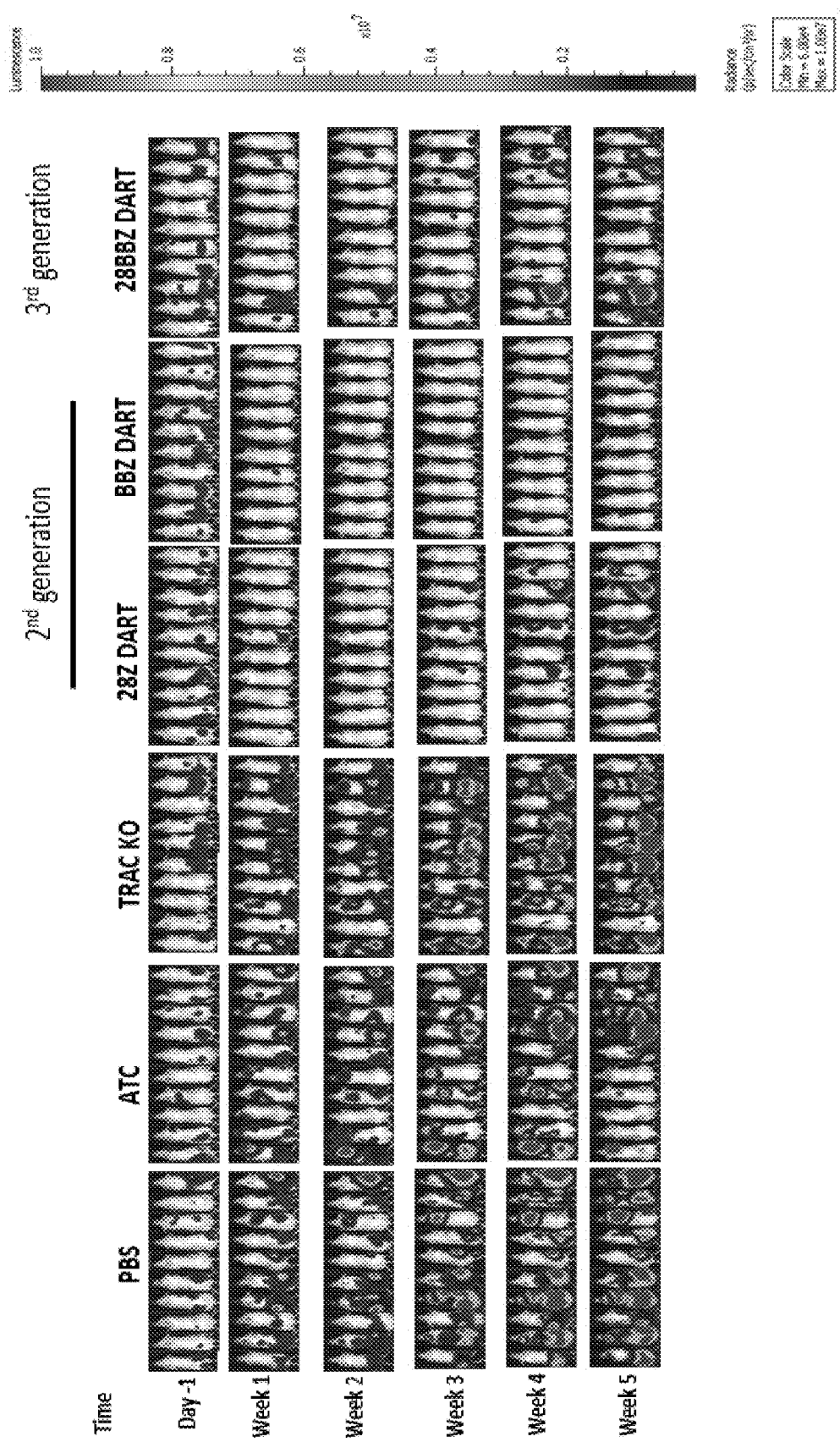
FIG. 30 shows tumoricidal activity of the CD38 CAR T cells assessed in a xenograft animal model. The negative control mice were administered phosphate-buffered saline, activated T-cells or a cell line carrying a knocked-out TRAC gene. Test mice were administered T cells expressing either 28Z or BBZ second generation construct, or third generation 28BBZ DAR construct. The 28Z DAR second generation construct includes a short hinge sequence, and the signaling region includes CD28 and CD3zeta signaling sequences (e.g., a DAR (V2b) construct). The BBZ second generation construct includes a short hinge sequence, and the signaling region includes 4-1BB and CD3zeta signaling sequences (e.g., a DAR (V2a) construct). The 28BBZ third generation construct includes a short hinge, and the signaling region includes CD28, 4-1BB and CD3zeta signaling sequences (e.g., a DAR (V2c) construct).

The tumoricidal activity of the T cells expressing CD38 DAR V2a construct were compared directly against T cells expressing either DAR V2b or DAR V2c in another in vivo xenograft animal model. The negative control mice were administered phosphate-buffered saline ("PBS") or activated T-cells ("ATC") or a cell line carrying a knocked-out TRAC gene ("TRAC KO"). The test mice were administered transgenic T cells expressing either CD38 DAR V2a, V2b or V2c construct. At week 5, the mice that were treated with T cells expressing the CD38 DAR V2a constructs ("BBZ") exhibited measurably less tumor burden compared to mice treated with T cells expressing either CD38 CAR V2b ("28Z") or V2c ("28BBZ") construct (FIG. 30).

Example 12: Results of T Cells Expressing DAR V2a Constructs

Expression levels of transgenic T cells expressing either anti-CD38 chimeric antigen receptor (CAR) or anti-CD38 dimeric antigen receptor (DAR) V2a or V2b construct were compared using flow cytometry. Transgenic T cells express a higher level of the DAR V2a (e.g., "BBZ") construct compared to transgenic T cells expressing the DAR V2b (e.g., "28Z") or CAR construct (FIG. 25).

Cell killing capability of T cells expressing either anti-CD38 chimeric antigen receptor (CAR) or anti-CD38 dimeric antigen receptor (DAR) V2a, V2b or V2c construct were compared in an in vitro cytotoxicity assay. Transgenic T cells expressing the DAR V2a construct ("BBZ" line C) exhibited better in vitro cell killing compared to transgenic T cells expressing the CAR construct (line B), but a lower cell killing level compared to T cells expressing DAR V2b ("28Z" line E) or T cells expressing the DAR V2c ("28BBZ" dotted line D) (FIG. 26).

Cytokine secretion capability of T cells expressing either anti-CD38 chimeric antigen receptor (CAR) or anti-CD38 dimeric antigen receptor (DAR) V2a or V2b construct were compared in an in vitro cytokine secretion assay. Transgenic T cells expressing the DAR V2a ("BBZ") exhibited a slightly higher level of IL-2 secretion compared to T cells expressing the DAR V2b ("28Z") construct, and a higher level compared to transgenic T cells expressing CAR construct (FIG. 27). Transgenic T cells expressing the DAR V2a ("BBZ") construct exhibited a slightly higher level of tumor necrosis factor alpha (TNFα) secretion compared to transgenic T cells expressing the CAR or DAR V2b ("28Z") construct (FIG. 28). Transgenic T cells expressing the DAR V2a ("BBZ") construct exhibited a slightly higher level of interferon-gamma (IFNγ) secretion compared to transgenic T cells expressing the CAR construct, but the cell expressing the DAR V2a ("BBZ") exhibited a slightly lower level of IFNγ secretion compared to transgenic T cells expressing the DAR V2b ("28Z") construct (FIG. 29).

An in vivo xenograft animal model was used to measure the tumoricidal activity of the CD38 DAR T cells in a xenograft animal model. The negative control mice were administered phosphate-buffered saline ("PBS") or a cell line carrying a knocked-out TRAC gene ("TRAC KO"). The test mice were administered transgenic T cells expressing either CD38 CAR or CD38 DAR (V2a) construct. At week 4, the mice that were treated with T cells expressing the CD38 DAR (V2a) constructs exhibited significantly less tumor burden compared to mice treated with T cells expressing a CD38 CAR construct (FIG. 19).

The tumoricidal activity of the T cells expressing CD38 DAR V2a construct were compared directly against T cells expressing either DAR V2b or DAR V2c in another in vivo xenograft animal model. The negative control mice were administered phosphate-buffered saline ("PBS") or activated T-cells ("ATC") or a cell line carrying a knocked-out TRAC gene ("TRAC KO"). The test mice were administered transgenic T cells expressing either CD38 DAR V2a, V2B or V2c construct. At week 5, the mice that were treated with T cells expressing the CD38 DAR V2a constructs ("BBZ") exhibited measurably less tumor burden compared to mice treated with T cells expressing either CD38 CAR V2b ("28Z") or V2c ("28BBZ") construct (FIG. 30).

Example 13: Results of T Cells Expressing DAR V3 Construct

Figure 20:
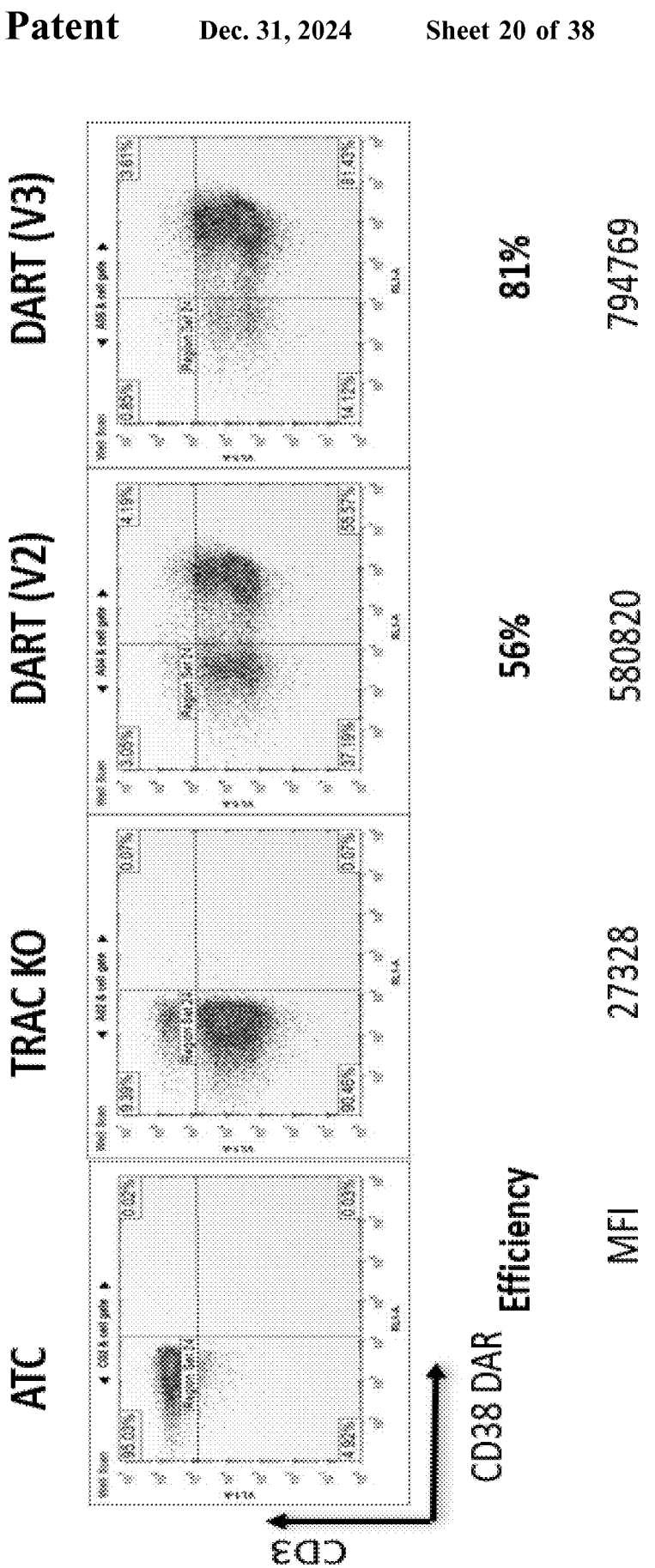
FIG. 20 shows the results of a flow cytometry study comparing T cells expressing a CD38 DAR (V2a) or (V3) construct. The negative controls include activated T cells, and a cell line carrying a knocked-out TRAC gene. The CD38 DAR (V2a) construct includes a short hinge sequence, and the signaling regions include 4-1BB and long CD3zeta intracellular signaling sequences. The CD38 DAR (V3) construct includes a short hinge sequence, and the signaling region includes 4-1BB and CD3zeta having a shortened ITAM region.
Figure 31:
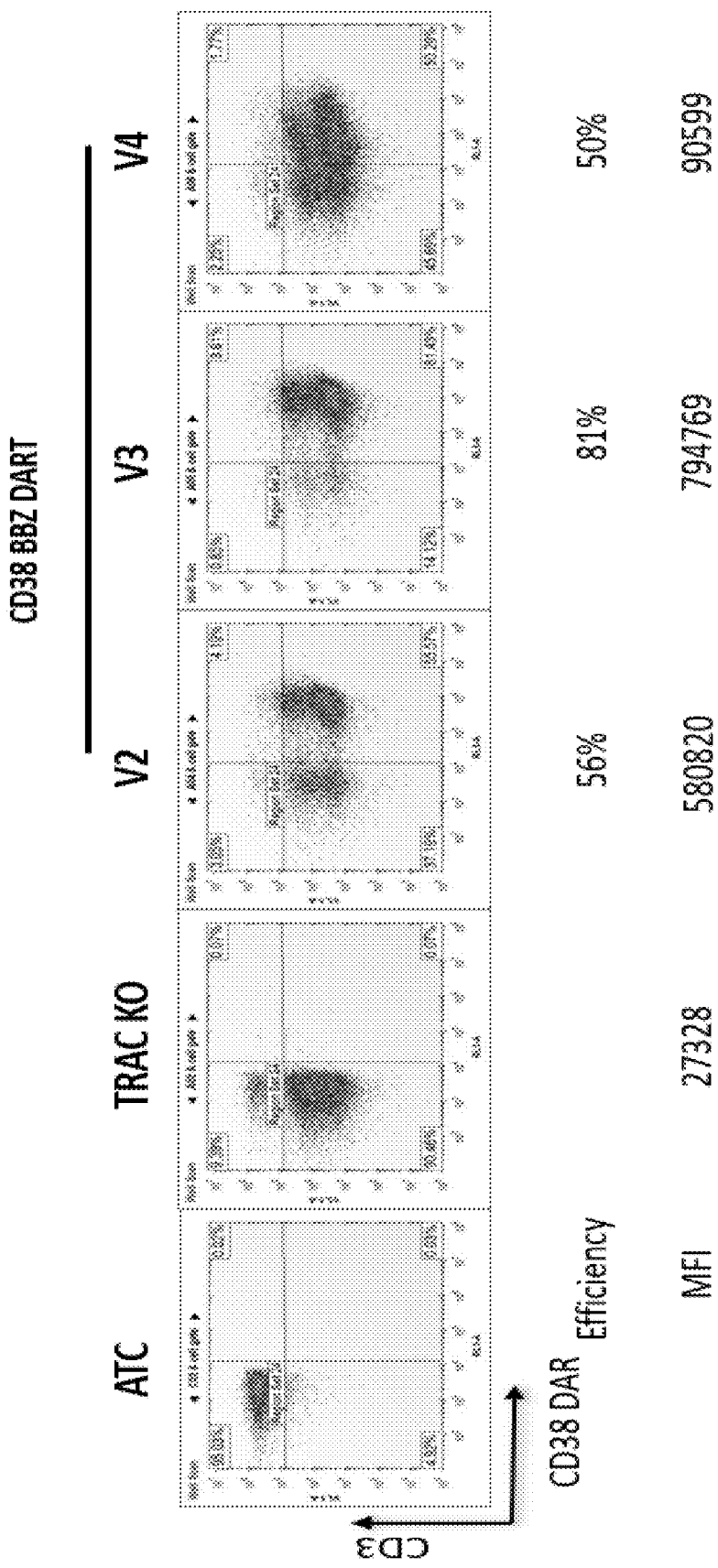
FIG. 31 shows the results of a flow cytometry study comparing T cells expressing a CD38 DAR V2, V3 or V4 constructs. The negative controls include activated T cells, and a cell line carrying a knocked-out TRAC gene. The CD38 V2 DAR construct includes a short hinge, and the signaling region includes 4-1BB and CD3zeta signaling sequences (e.g., a DAR (V2a) construct). The CD38 V3 DAR construct includes a short hinge sequence, and the signaling region includes 4-1BB and CD3-zeta (with only ITAM 3 motif) signaling sequences (e.g, a DAR (V3) construct). The CD38 DAR V4 construct lacks a hinge sequence, and the signaling region includes 4-1BB and CD3-zeta (with only ITAM 3 motif) signaling sequences (e.g., a DAR (V4) construct).

Expression levels of transgenic T cells expressing anti-CD38 dimeric antigen receptor (DAR) V2a or V3 construct were compared using flow cytometry. Transgenic T cells express a higher level of the DAR V3 construct compared to transgenic T cells expressing the DAR V2a (FIGS. 20 and 31).

Figure 21:
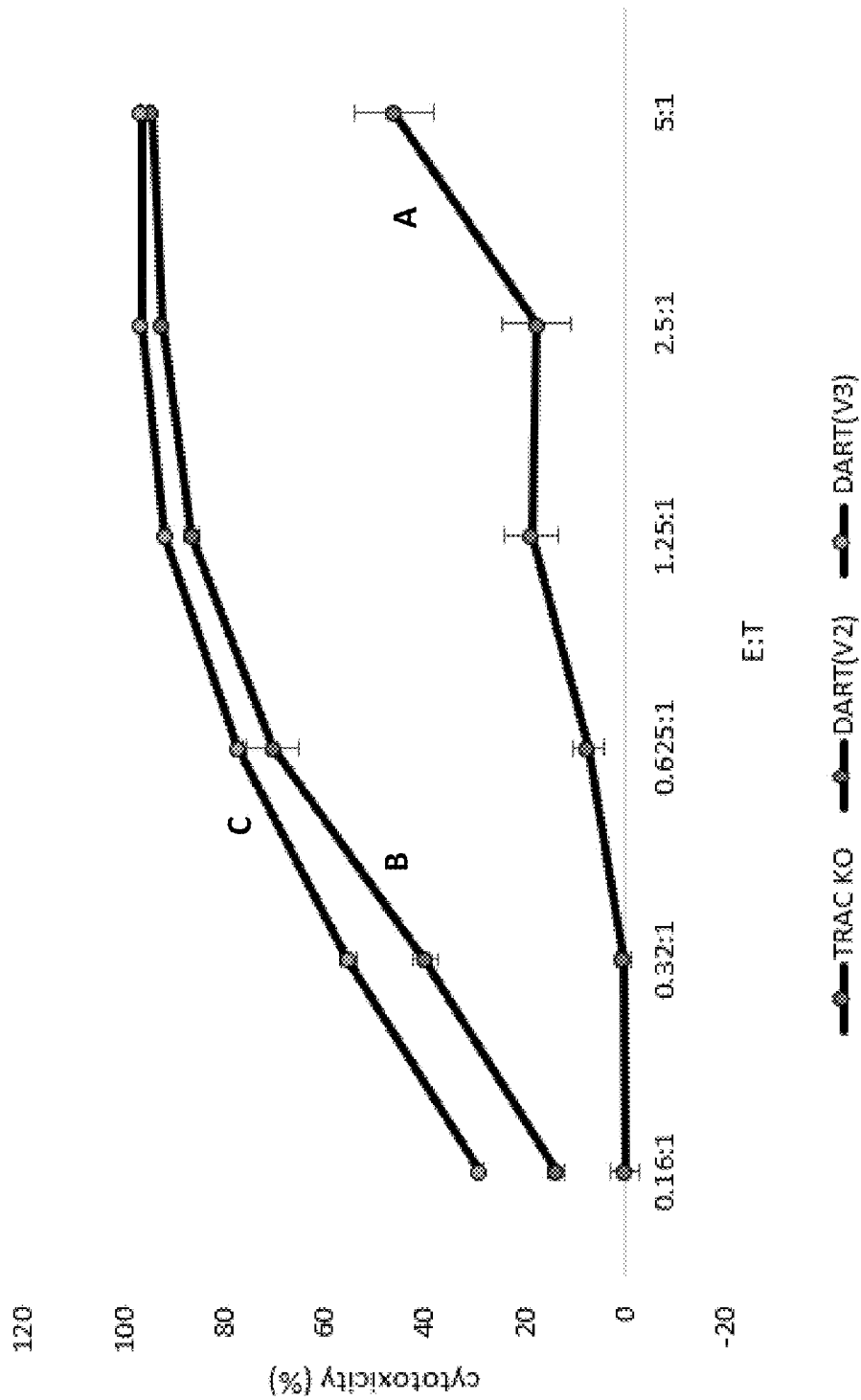
FIG. 21 is a graph showing the percent cytotoxicity of T cells expressing CD38 DAR (V2a) compared to (V3), on RPMI 8226 target cells. The negative control is a cell line (line A) carrying a knocked-out TRAC gene. The CD38 DAR (V2a) construct (line B) includes a short hinge sequence, and the signaling regions include 4-1BB and long CD3zeta intracellular signaling sequences. The CD38 DAR (V3) construct (line C) includes a short hinge sequence, and the signaling region includes 4-1BB and CD3zeta having a shortened ITAM region.

Cell killing capability of T cells expressing anti-CD38 dimeric antigen receptor (DAR) V2a or V3 construct were compared in an in vitro cytotoxicity assay. Transgenic T cells expressing the DAR V3 (line C) exhibited a higher level of in vitro cell killing compared to transgenic T cells expressing the DAR V2a construct (line B) (FIG. 21).

Figure 22:
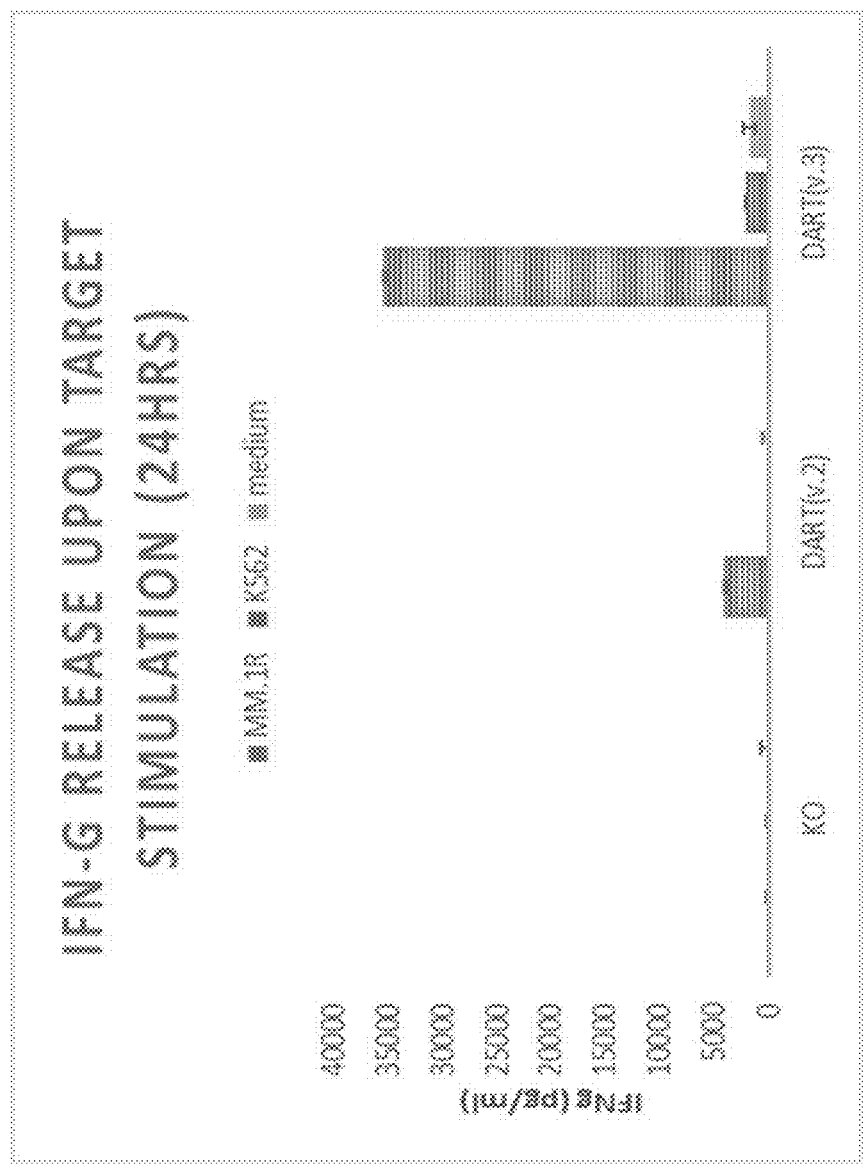
FIG. 22 is a bar graph showing the level of IFN-gamma release from T cells expressing CD38 DAR (V2a) compared to DAR (V3) constructs. Each data set shows from left to right RPMI 8226 cells, K562 cells and medium. The negative control is a cell line carrying a knocked-out TRAC gene. The CD38 DAR (V2a) construct includes a short hinge sequence, and the signaling regions include 4-1BB and long CD3zeta intracellular signaling sequences. The CD38 DAR (V3) construct includes a short hinge sequence, and the signaling region includes 4-1BB and CD3zeta having a shortened ITAM region.
Figure 23:
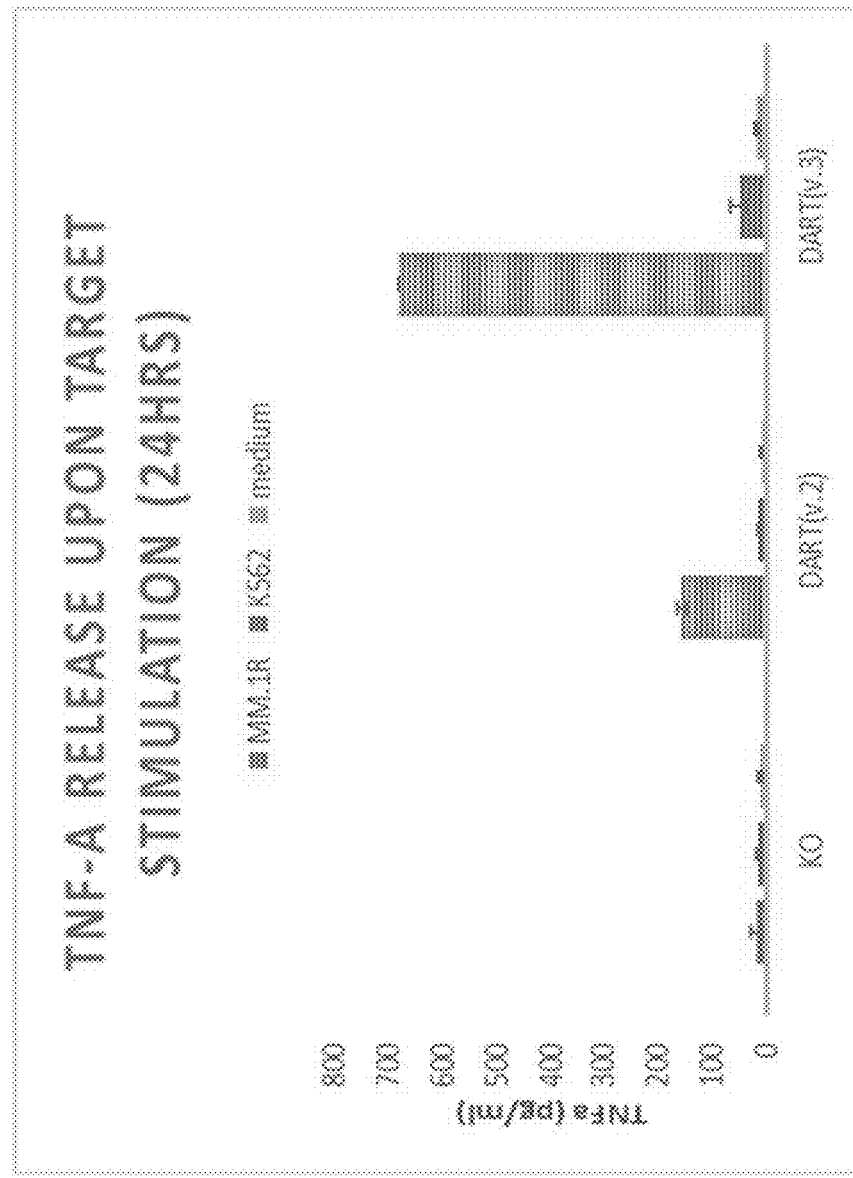
FIG. 23 is a bar graph showing the level of TNF-alpha release from T cells expressing CD38 DAR (V2a) compared to DAR (V3) constructs. Each data set shows from left to right RPMI 8226 cells, K562 cells and medium. The negative control is a cell line carrying a knocked-out TRAC gene. The CD38 DAR (V2a) construct includes a short hinge sequence, and the signaling regions include 4-1BB and long CD3zeta intracellular signaling sequences. The CD38 DAR (V3) construct includes a short hinge sequence, and the signaling region includes 4-1BB and CD3zeta having a shortened ITAM region.

Cytokine secretion capability of T cells expressing anti-CD38 dimeric antigen receptor (DAR) V2a or V3 construct were compared in an in vitro cytokine secretion assay. Transgenic T cells expressing the DAR V3 exhibited a markedly higher level of interferon-gamma (IFNγ) secretion compared to T cells expressing the DAR V2a (FIG. 22). Transgenic T cells expressing the DAR V3 exhibited a markedly higher level of tumor necrosis factor alpha (TNFα) secretion compared to transgenic T cells expressing the DAR V2a construct (FIG. 23).

Figure 33:
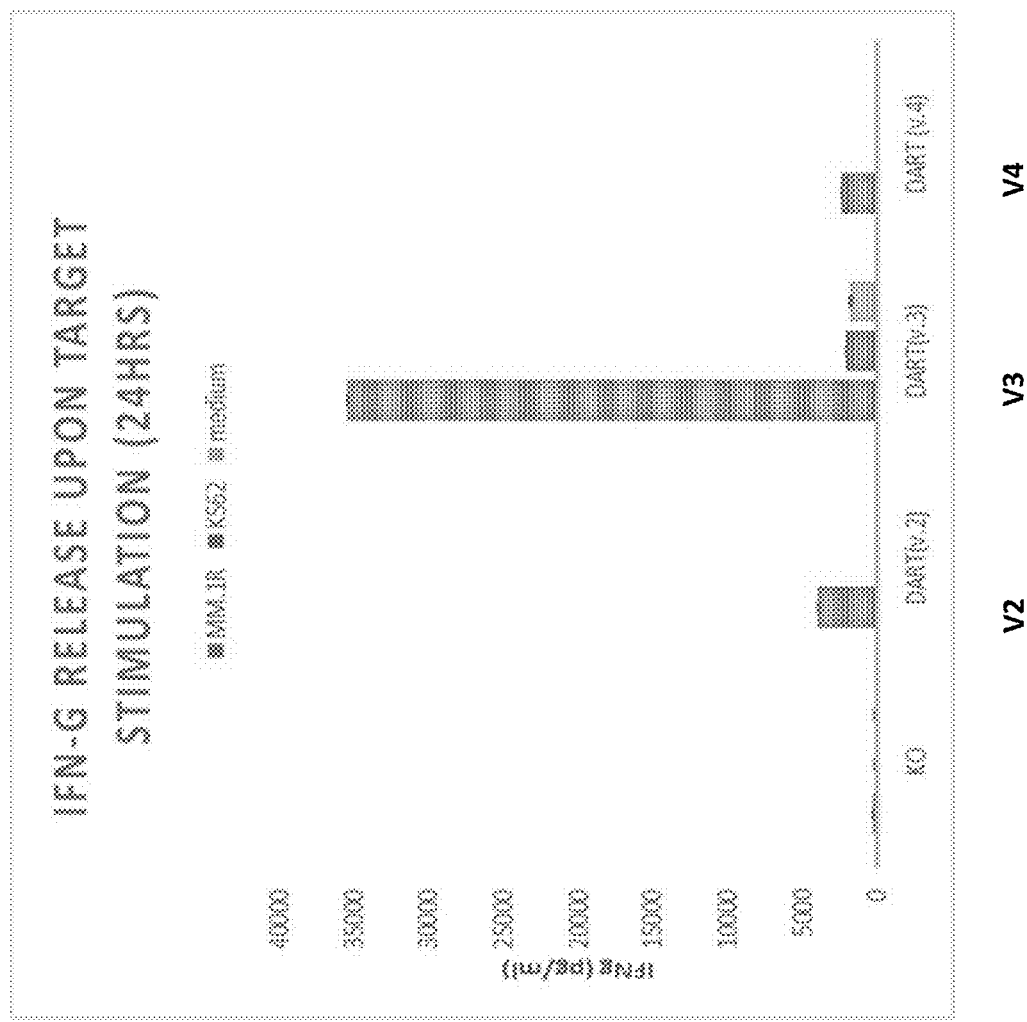
FIG. 33 is a bar graph showing the level of IFN-gamma release from T cells expressing CD38 DAR V2, V3 or V4 constructs. Each data set shows from left to right RPMI 8226 cells, K562 cells and medium. The negative control is a cell line carrying a knocked-out TRAC gene. The CD38 V2 DAR construct includes a short hinge, and the signaling region includes 4-1BB and CD3zeta signaling sequences (e.g., DAR (V2a) construct). The CD38 V3 DAR construct includes a short hinge sequence, and the signaling region includes 4-1BB and CD3-zeta (with only ITAM 3 motif) signaling sequences (e.g., DAR (V3) construct). The CD38 DAR V4 construct lacks a hinge sequence, and the signaling region includes 4-1BB and CD3-zeta (with only ITAM 3 motif) signaling sequences (e.g., DAR (V4) construct).
Figure 34:
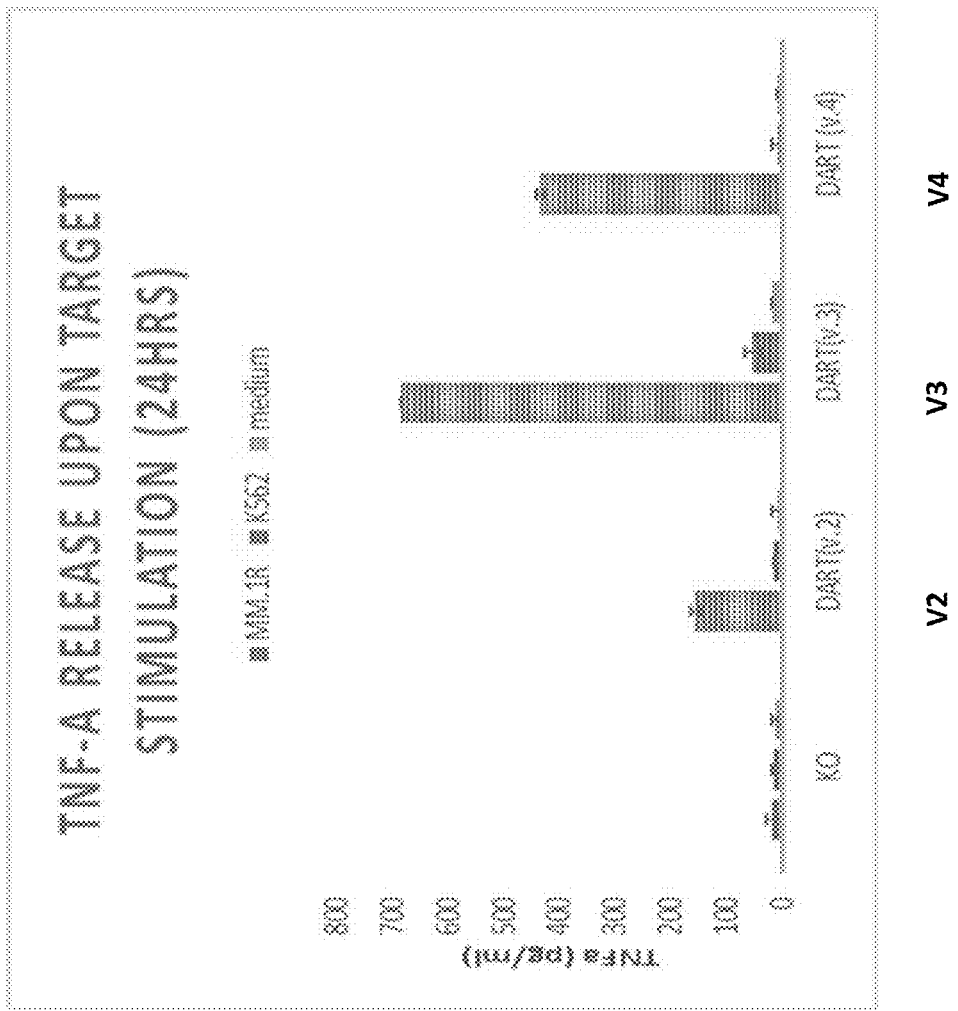
FIG. 34 is a bar graph showing the level of TNF-alpha release from T cells expressing CD38 DAR V2, V3 or V4 constructs. Each data set shows from left to right RPMI 8226 cells, K562 cells and medium. The negative control is a cell line carrying a knocked-out TRAC gene. The CD38 V2 DAR construct includes a short hinge, and the signaling region includes 4-1BB and CD3zeta signaling sequences (e.g., DAR (V2a) construct). The CD38 V3 DAR construct includes a short hinge sequence, and the signaling region includes 4-1BB and CD3-zeta (with only ITAM 3 motif) signaling sequences (e.g., DAR (V3) construct). The CD38 DAR V4 construct lacks a hinge sequence, and the signaling region includes 4-1BB and CD3-zeta (with only ITAM 3 motif) signaling sequences (e.g., DAR (V4) construct).

Cytokine secretion capability of T cells expressing anti-CD38 dimeric antigen receptor (DAR) V2a or V3 were compared in an in vitro cytokine secretion assay. Transgenic T cells expressing the DAR V3 construct exhibited a markedly higher level of interferon-gamma (IFNγ) secretion compared to transgenic T cells expressing the V2a construct (FIG. 33). Transgenic T cells expressing the DAR V3 construct exhibited a lower level of tumor necrosis factor alpha (TNFα) secretion compared to transgenic T cells expressing the DAR V2a construct (FIG. 34).

Figure 24:
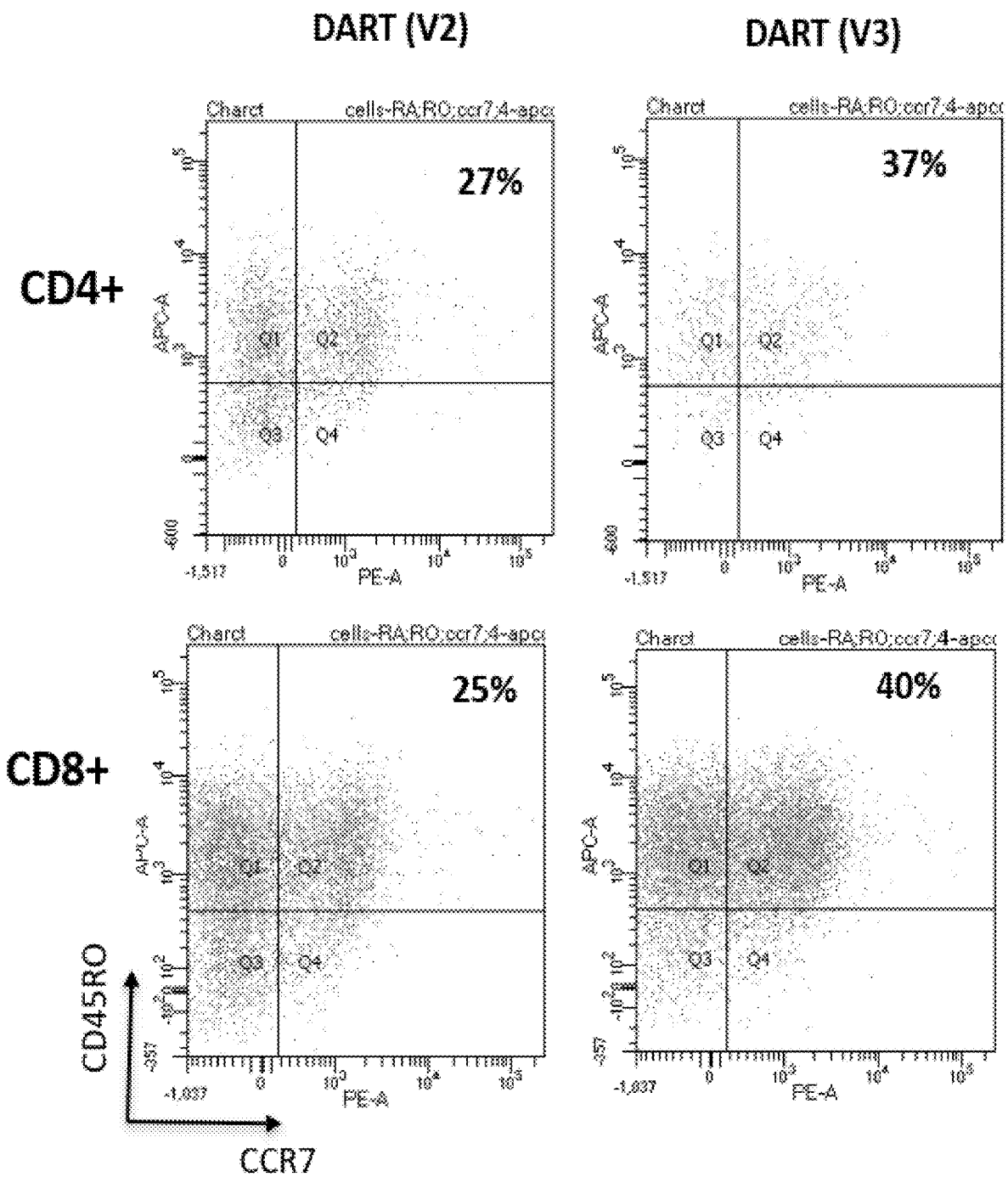
FIG. 24 shows the results of a flow cytometry study to measure the fraction of memory T cells in CD38 DAR (V2a) and DAR (V3) T cells. The CD38 DAR (V2a) construct includes a short hinge sequence, and the signaling regions include 4-1BB and long CD3zeta intracellular signaling sequences. The CD38 DAR (V3) construct includes a short hinge sequence, and the signaling region includes 4-1BB and CD3zeta having a shortened ITAM region.

Flow cytometry was used to detect the presence of central memory T cells (TCM) in a population of T cells expressing either DAR V2a or V3 construct. T cells expressing DAR V3 construct exhibited a higher percentage of central memory T cells (TCM) compared to T cells expressing DAR V2a (FIG. 24).

Figure 32:
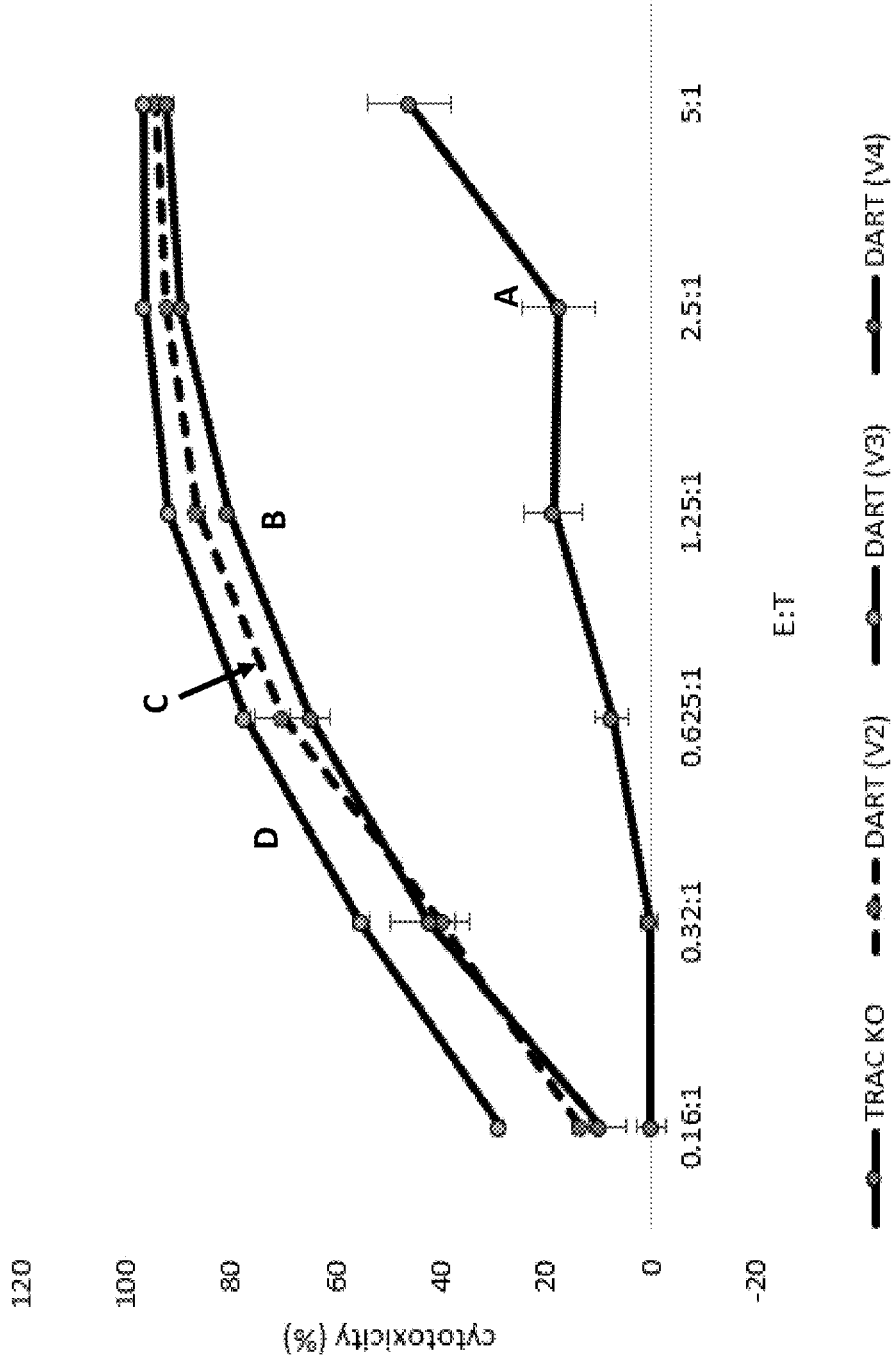
FIG. 32 is a graph showing the percent cytotoxicity of T cells expressing CD38 DAR V2, V3 or V4 construct, on RPMI 8226 target cells. The negative control (line A) is a cell line carrying a knocked-out TRAC gene. The CD38 DAR V4 construct (line B) lacks a hinge sequence, and the signaling region includes 4-1BB and CD3-zeta (with only ITAM 3 motif) signaling sequences (e.g., DAR (V4) construct). The CD38 V2 DAR construct (C dotted line) includes a short hinge, and the signaling region includes 4-1BB and CD3zeta signaling sequences (e.g., DAR (V2a) construct). The CD38 V3 DAR construct (line D) includes a short hinge sequence, and the signaling region includes 4-1BB and CD3-zeta (with only ITAM 3 motif) signaling sequences (e.g., DAR (V3) construct).

Cell killing capability of T cells expressing anti-CD38 dimeric antigen receptor (DAR) V2a or V3 construct were compared in an in vitro cytotoxicity assay. Transgenic T cells expressing the DAR V2a construct (dotted line C) exhibited a similar level of in vitro cell killing compared to transgenic T cells expressing the DAR V3 (line D) (FIG. 32).

Example 14: Results of T Cells Expressing DAR V4 Constructs

Expression levels of transgenic T cells expressing anti-CD38 dimeric antigen receptor (DAR) V2a, V3 or V4 construct were compared using flow cytometry. Transgenic T cells express a higher level of the DAR V3 construct compared to transgenic T cells expressing the DAR V2a or V4 construct (FIG. 31).

Cell killing capability of T cells expressing anti-CD38 dimeric antigen receptor (DAR) V2a, V3 or V4 construct were compared in an in vitro cytotoxicity assay. Transgenic T cells expressing the DAR V4 construct (line B) exhibited a similar level of in vitro cell killing compared to transgenic T cells expressing the DAR V2a construct (dotted line C) or DAR V3 (line D) (FIG. 32). The DAR V4 construct lacks a hinge region, and the cell killing results indicate that a DAR construct devoid of a hinge region does not improve the cell killing capability of T cells expressing the DAR V4 construct compared to T cells expressing the V2a or V3 constructs, both of which include a short hinge region (e.g., only CD28 hinge sequence).

Cytokine secretion capability of T cells expressing anti-CD38 dimeric antigen receptor (DAR) V2a, V3 or V4 construct were compared in an in vitro cytokine secretion assay. Transgenic T cells expressing the DAR V4 construct exhibited a markedly reduced level of interferon-gamma (IFNγ) secretion compared to T cells expressing DAR V3 construct (FIG. 33). Transgenic T cells expressing the DAR V4 construct exhibited a lower level of tumor necrosis factor alpha (TNFα) secretion compared to transgenic T cells expressing the DAR V3 construct (FIG. 34).

What is claimed:

1. A nucleic acid encoding a precursor polypeptide comprising ten regions ordered from the amino terminus to the carboxyl terminus: (1) a heavy chain leader sequence, (2) an antibody heavy chain variable region comprising a CD38 antibody heavy chain variable region which comprises the amino acid sequence of SEQ ID NO:1, (3) an antibody heavy chain constant region, (4) an optional hinge region, (5) a transmembrane region, (6) an intracellular signaling region, (7) a T2A cleavage sequence, (8) a light chain leader sequence, (9) an antibody light chain variable region comprising a CD38 antibody light chain variable region which comprises the amino acid sequence of SEQ ID NO:3, and (10) an antibody light chain constant region.

2. The nucleic acid of claim 1, comprising (4) the hinge region.

3. The nucleic acid of claim 1, wherein (1) the heavy chain leader sequence comprises the amino acid sequence of SEQ ID NO: 10; (3) the antibody heavy chain constant region comprises a CD38 antibody heavy chain constant region which comprises the amino acid sequence of SEQ ID NO:2; (4) the hinge region is selected from a group consisting of a CD28 hinge region comprising the amino acid sequence of SEQ ID NO:5, a CD8 hinge region comprising the amino acid sequence of SEQ ID NO:21, and a hinge region comprising a CD28 hinge region comprising the amino acid sequence of SEQ ID NO:5 and a CD8 hinge region comprising the amino acid sequence of SEQ ID NO:21; (5) the transmembrane region comprises a CD28 transmembrane region which comprises the amino acid sequence of SEQ ID NO:6; (6) the intracellular signaling region comprises any one or any combination of two or more signaling sequences selected from a group consisting of 4-1BB signaling sequence comprising the amino acid sequence of SEQ ID NO:7, CD28 signaling sequence comprising the amino acid sequence of SEQ ID NO:8, CD3zeta (long) signaling sequence comprising the amino acid sequence of SEQ ID NO:9 and/or CD3zeta (short) signaling sequence having an ITAM 3 motif and comprising the amino acid sequence of SEQ ID NO:20; (7) the T2A cleavage sequence comprises the amino acid sequence of SEQ ID NO:12; (8) the light chain leader sequence comprises the amino acid sequence of SEQ ID NO: 11; and (10) the antibody light chain constant region comprises a CD38 antibody light chain constant region which comprises the amino acid sequence of SEQ ID NO:4.

4. A vector operably linked to the nucleic acid of claim 1.

5. A host cell or a population of host cells harboring the vector of claim 4.

6. The host cell of claim 5, wherein the vector is an expression vector, and wherein the expression vector directs transcription and/or translation (expression) of the nucleic acid.

7. The host cell or the population of host cells of claim 5, wherein the host cell or the population of host cells comprise T lymphocytes (T cells, regulatory T cells, gamma-delta T cells or cytotoxic T cells), NK (natural killer) cells, macrophages, dendritic cells, mast cells, eosinophils, B lymphocytes or monocytes.

8. A method for treating a subject having a disease, disorder or condition associated with detrimental expression of a tumor antigen in the subject, comprising: administering to the subject the host cell or the population of host cells of claim 5.

9. The method of claim 8, wherein the disease is a hematologic cancer selected from the group consisting of non-Hodgkin's lymphoma (NHL), Burkitt's lymphoma (BL), B chronic lymphocytic leukemia (B-CLL), B and T acute lymphocytic leukemia (ALL), T cell lymphoma (TCL), acute myeloid leukemia (AML), hairy cell leukemia (HCL), Hodgkin's Lymphoma (HL), chronic myeloid leukemia (CML) and multiple myeloma (MM).

10. A method for treating a subject having a disease, disorder or condition associated with detrimental expression of a tumor antigen in the subject, comprising: administering to the subject the host cell or the population of host cells of claim 6.

* * * * *